United States Patent
Hawkins et al.

(10) Patent No.: US 11,299,534 B2
(45) Date of Patent: *Apr. 12, 2022

(54) CD8A-BINDING FIBRONECTIN TYPE III DOMAINS

(71) Applicant: Janssen Biotech, Inc., Horsham, PA (US)

(72) Inventors: Rebecca Hawkins, Harleysville, PA (US); Steven Jacobs, North Wales, PA (US); Manuel Sepulveda, Princeton Junction, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/821,064

(22) Filed: Mar. 17, 2020

(65) Prior Publication Data

US 2021/0032312 A1 Feb. 4, 2021

Related U.S. Application Data

(63) Continuation of application No. 15/839,915, filed on Dec. 13, 2017, now Pat. No. 10,626,165.

(60) Provisional application No. 62/434,017, filed on Dec. 14, 2016.

(51) Int. Cl.
| | | |
|---|---|---|
| C07K 14/00 | (2006.01) | |
| C07K 14/52 | (2006.01) | |
| C07K 14/78 | (2006.01) | |
| G01N 33/569 | (2006.01) | |
| G01N 33/68 | (2006.01) | |
| G01N 33/566 | (2006.01) | |
| A61K 51/08 | (2006.01) | |
| G01N 33/53 | (2006.01) | |
| A61K 49/00 | (2006.01) | |
| G01N 33/574 | (2006.01) | |

(52) U.S. Cl.
CPC .......... *C07K 14/78* (2013.01); *A61K 49/0002* (2013.01); *A61K 51/088* (2013.01); *G01N 33/53* (2013.01); *G01N 33/566* (2013.01); *G01N 33/569* (2013.01); *G01N 33/56966* (2013.01); *G01N 33/574* (2013.01); *G01N 33/57492* (2013.01); *G01N 33/68* (2013.01); *G01N 33/6887* (2013.01); *G01N 2333/70517* (2013.01); *G01N 2333/78* (2013.01)

(58) Field of Classification Search
None
See application file for complete search history.

(56) References Cited

U.S. PATENT DOCUMENTS

| | | |
|---|---|---|
| 4,281,061 A | 7/1981 | Zuk et al. |
| 5,223,409 A | 6/1993 | Ladner et al. |
| 5,643,763 A | 7/1997 | Dunn et al. |
| 5,643,768 A | 7/1997 | Kawasaki |
| 5,658,727 A | 8/1997 | Barbas et al. |
| 5,691,157 A | 11/1997 | Gong et al. |
| 5,846,456 A | 12/1998 | Liu |
| 5,856,456 A | 1/1999 | Whitlow et al. |
| 6,018,030 A | 1/2000 | Ferrari et al. |
| 6,162,903 A | 12/2000 | Trowern et al. |
| 6,172,197 B1 | 1/2001 | McCafferty et al. |
| 6,355,776 B1 | 3/2002 | Ferrari et al. |
| 6,462,189 B1 | 10/2002 | Koide |
| 6,472,147 B1 | 10/2002 | Janda et al. |
| 6,521,427 B1 | 2/2003 | Evans |
| 6,582,915 B1 | 6/2003 | Griffiths et al. |
| 6,670,127 B2 | 12/2003 | Evans |
| 6,673,901 B2 | 1/2004 | Koide |
| 6,703,199 B1 | 3/2004 | Koide |
| 6,818,418 B1 | 11/2004 | Lipovsek et al. |
| 6,846,655 B1 | 1/2005 | Wagner et al. |
| 6,969,108 B2 | 11/2005 | Fukumoto et al. |
| 7,078,490 B2 | 7/2006 | Koide |
| 7,115,396 B2 | 10/2006 | Lipovsek et al. |
| 7,119,171 B2 | 10/2006 | Koide |
| 7,153,661 B2 | 12/2006 | Koide |
| 7,288,638 B2 | 10/2007 | Jure-Kunkel et al. |
| 7,427,672 B2 | 9/2008 | Imanishi et al. |
| 7,709,214 B2 | 5/2010 | Freeman et al. |
| 7,794,710 B2 | 9/2010 | Chen et al. |
| 7,842,476 B2 | 11/2010 | McGregor et al. |
| 7,943,743 B2 | 5/2011 | Korman et al. |

(Continued)

FOREIGN PATENT DOCUMENTS

| | | |
|---|---|---|
| CN | 102076713 A | 5/2011 |
| CN | 103827361 A | 5/2014 |

(Continued)

OTHER PUBLICATIONS

Burgess et al. Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138, 1990 (Year: 1990).*

(Continued)

*Primary Examiner* — Maher M Haddad
(74) *Attorney, Agent, or Firm* — Troutman Pepper Hamilton Sanders LLP

(57) ABSTRACT

Fibronectin type III domains (FN3) that specifically bind to CD8A, related polynucleotides capable of encoding CD8A-specific FN3 domains, cells expressing the FN3 domains, as well as associated vectors, and detectably labeled FN3 domains are useful in therapeutic and diagnostic applications.

20 Claims, 20 Drawing Sheets

Specification includes a Sequence Listing.

(56) References Cited

U.S. PATENT DOCUMENTS

| | | |
|---|---|---|
| 8,217,149 B2 | 7/2012 | Irving et al. |
| 8,278,419 B2 | 10/2012 | Jacobs et al. |
| 8,293,482 B2 | 10/2012 | Jacobs et al. |
| 8,552,154 B2 | 10/2013 | Freeman et al. |
| 8,569,227 B2 | 10/2013 | Jacobs |
| 8,741,295 B2 | 6/2014 | Olive |
| 8,779,108 B2 | 7/2014 | Queva et al. |
| 8,981,063 B2 | 3/2015 | Chen |
| 9,156,887 B2 | 10/2015 | Jacobs |
| 9,175,082 B2 | 11/2015 | Zhou et al. |
| 9,200,273 B2 | 12/2015 | Diem et al. |
| 9,212,224 B2 | 12/2015 | Cogswell et al. |
| 9,326,941 B2 | 5/2016 | Chae et al. |
| 9,546,368 B2 | 1/2017 | Bennett et al. |
| 9,644,023 B2 * | 5/2017 | Torres .................... A61P 31/04 |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 | 4/2020 | Diem et al. |
| 10,626,165 B2 * | 4/2020 | Hawkins ................ G01N 33/53 |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0144601 A1 | 6/2010 | Jacobs et al. |
| 2010/0179094 A1 | 7/2010 | Emanuel et al. |
| 2010/0216708 A1 | 8/2010 | Jacobs et al. |
| 2010/0254989 A1 | 10/2010 | Bossenmaier et al. |
| 2010/0255056 A1 | 10/2010 | Jacobs et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0184212 A1 | 7/2013 | Camphausen et al. |
| 2013/0226834 A1 | 8/2013 | Gannalo, II |
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0197571 A1 | 7/2015 | Freeman et al. |
| 2015/0203580 A1 | 7/2015 | Papadopoulos et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0348397 A1 | 12/2017 | Diem et al. |
| 2017/0362301 A1 | 12/2017 | Anderson et al. |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1 | 6/2019 | Dudkin et al. |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |

FOREIGN PATENT DOCUMENTS

| | | |
|---|---|---|
| CN | 105907719 A | 8/2016 |
| EP | 0985039 A2 | 3/2000 |
| EP | 1137941 A1 | 10/2001 |
| EP | 1210428 A1 | 6/2002 |
| EP | 1266025 A1 | 12/2002 |
| EP | 2935329 A1 | 10/2015 |
| JP | 2011507543 A | 3/2011 |
| JP | 2011517314 A | 6/2011 |
| JP | 2011520961 A | 7/2011 |
| JP | 2011522517 A | 8/2011 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007085815 A2 | 8/2007 |
| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |
| WO | 2009102421 A2 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2010039248 A1 | 4/2010 |
| WO | 2010051274 A2 | 5/2010 |
| WO | 2010051310 A2 | 5/2010 |
| WO | 2010060095 A1 | 5/2010 |
| WO | 2010093627 A3 | 10/2010 |
| WO | 2010115202 A2 | 10/2010 |
| WO | 2010115551 A1 | 10/2010 |
| WO | 2011005133 A1 | 1/2011 |
| WO | 2011110642 A2 | 9/2011 |
| WO | 2011130324 A1 | 10/2011 |
| WO | 2011131746 A2 | 10/2011 |
| WO | 2011137319 A2 | 11/2011 |
| WO | 2011151412 A1 | 12/2011 |
| WO | 2012016245 A2 | 2/2012 |
| WO | 2013049275 A1 | 4/2013 |
| WO | 2014081944 A2 | 5/2014 |
| WO | 2014081954 A1 | 5/2014 |
| WO | 2014100079 A1 | 6/2014 |
| WO | 2014165082 A2 | 10/2014 |

(56) References Cited

FOREIGN PATENT DOCUMENTS

| | | |
|---|---|---|
| WO | 2014165093 A2 | 10/2014 |
| WO | 2014189973 A2 | 11/2014 |
| WO | 2014209804 A1 | 12/2014 |
| WO | 2015061668 A1 | 4/2015 |
| WO | 2015092393 A2 | 6/2015 |
| WO | 2015109124 A2 | 7/2015 |
| WO | 2015195163 A1 | 12/2015 |
| WO | 2016000619 A1 | 1/2016 |
| WO | 2016004043 A1 | 1/2016 |
| WO | 2016086021 A1 | 6/2016 |
| WO | 2016086036 | 6/2016 |
| WO | 2016179534 | 11/2016 |
| WO | 2016197071 A1 | 12/2016 |
| WO | 2017011618 A1 | 1/2017 |

OTHER PUBLICATIONS

Lazar et al. Transforming growth factor alpha: mutation of aspartic acid 47 and leucine 48 results in different biological activities. Mol Cell Biol. 8:1247-1252, 1988. (Year: 1988).*

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*

Rudikoff, et al. Single amino acid substitution altering antigen-binding specificity. Proc Natl Acad Sci U S A. Mar. 1982; 79(6): 1979-1983. (Year: 1983).*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

Skerra, et al., "Engineered protein scaffolds for molecular recognition," Journal of Molecular Recognition, 13: 167-187 (2000).

Koide, et al., "The Fibronectin Type III Domain as a Scaffold for Novel Binding Proteins," Journal of Molecular Biology, 284: 1141-1151 (1998).

Karatan, et al., "Molecular Recognition Properties of FN3 Monobodies that Bind the Src SH3 Domain," Chemistry & Biology, 11: 835-844 (2004).

Parker, et al., "Antibody mimics based on human fibronectin type three domain engineered for thermostability and high-affinity binding to vascular endothelial growth factor receptor two," Protein Engineering, Design & Selection, 18(9): 435-444 (2005).

Siggers et al. Conformational dynamics in loop swap mutants of homologous fibronectin type III domains. Biophys J. Oct. 1, 2007 ;93(7):2447-56.

Skolnick et al. From genes to protein structure and function: novel applications of computational approaches in the genomic era. Trends Biotechnol. 18(1 ):34-9, 2000.

Attwood TK. Genomics. The Babel of bioinformatics. Science. 290(5491 ):471-473, 2000.

Miller et al Ligand binding to proteins: the binding landscape model. Protein Sci. Oct. 1997;6(10):2166-79.

Kuntz. Structure-based strategies for drug design and discovery. Science. 1992 257(5073):1078-1082.

Koivunen et al. Identification of Receptor Ligands with Phage Display Peptide Libraries J Nucl Med; 40:883-888, 1999.

Reiss et al. Inhibition of platelet aggregation by grafting RGD and KGD sequences on the structural scaffold of small disulfide-rich proteins. Platelets 17(3):153-157, 2006.

Helms et al. Destabilizing loop swaps in the CDRs of an immunoglobulin VL domain. Protein Science 4:2073-2081, 1995.

Bass, et al., "Hormone Phage: An Enrichment Method for Variant Proteins with Altered Binding Properties," Proteins: Structure, Function, and Genetics, 8: 309-314 (1990).

Clarke, et al., "Folding and Stability of a Fibronectin Type III Domain of Human Tenascin," Journal of Molecular Biology, 270: 771-778 (1997).

Dehouck, et al., "Fast and accurate predictions of protein stability changes upon mutations using statistical potentials and neural networks: PoPMuSiC-2.0," Bioinformatics, 25(19): 2537-2543 (2009).

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Dutta, et al., "High-affinity fragment complementation of a fibronectin type III domain and its application to stability enhancement," Protein Science, 14: 2838-2848 (2005).

Garrard, et al., "Selection of an anti-IGF-1 Fab from a Fab phage library created by mutagenesis of multiple CDR loops," Gene, 128: 103-109 (1993).

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Hackel, et al., "Stability and CDR Composition Biases Enrich Binder Functionality Landscapes," Journal of Molecular Biology, 401: 84-96 (2010).

Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide, et al., Teaching an Old Scaffold New Tricks: Monobodies Constructed Using Alternative Surfaces of the FN3 Scaffold, Journal of Molecular Biology, 415: 393-405 (2012).

Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).

C.N. Pace, "Determination and Analysis of Urea and Guanidine Hydrochloride Denaturation Curves," Methods in Enzymology, 131: 266-280 (1986).

Steiner, et al., "Efficient Selection of DARPins with Sub-nonomolar Affinities using SRP Phage Display," Journal of Molecular Biology, 382: 1211-1227 (2008).

Xu, et al., "Directed Evolution of High-Affinity Antibody Mimics Using mRNA Display," Chemistry & Biology, 9: 933-942 (2002).

Cota, et al., "Two Proteins with the Same Structure Respond very Differently to Mutation: The Role of Plasticity in Protein Stability", Journal of Molecular Biology, 302, 713-725 (2000).

Hamill et al., "The Effect of Boundary Selection on the Stability and Folding of the Third Fibronectin Type III Domain from Human Tenascin", Biochemistry, 37: 8071-8079 (1998).

Garcia-Ibilcieta, et al., "Simple method for production of randomized human tenth fibronectin domain III libraries for use in combinatorial screening procedures," Bio Technologies, 44: 559-562 (2008).

Van den Burg et al., "Selection of mutations for increased protein stability", Curr. Opin. Biotech. 13:333-337 (2002).

GenBank Accession No. NP_002151.

Slonomics® Technology Website "https://www.morphosys.com/science/drug-development-capabilities/slonomics".

UniProt Accession No. P10039.

SwissProt Accession No. P00533.2, "Epidermal Growth Factor Receptor," pp. 1-49 (Jun. 11, 2014).

Turke et al., "Preexistence and Clonal Selection of MET Amplification in EGFR Mutant NSCLC," Cancer Cell, vol. 17, pp. 77-88 (2010).

Ullrich et al., "Human epidermal growth factor receptor cDNA sequence and aberrant expression of the amplified Jene in A431 epidermoid carcinoma cells," Nature, vol. 309, pp. 418-425 (1984).

Zhang et al., "Complete disulfide bond assignment of a recombinant immunoglobulin G4 monoclonal antibody," Analytical Biochemistry, vol. 311, pp. 1-9 (2002).

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).

(56) References Cited

OTHER PUBLICATIONS

Basel GA et al., "Critical Update and Emerging Trends in Epidermal Growth Factor Receptor Targeting in Cancer," Journal of Clinical Oncology, vol. 23, No. 11, pp. 2445-2459 (2005).
Batley et al., "Inhibition of FGF-1 Receptor Tyrosine Kinase Activity by PD 161570, a New Protein-Tyrosine Kinase nhibitor," Life Sciences, vol. 62, No. 20, pp. 143-150 (1998).
Bean et al., "MET amplification occurs with or without T790M mutations in EGFR mutant lung tumors with acquired esistance to gefilinib or erlotinib," Proceedings of the National Academy of Science, vol. 104, No. 52, pp. ) 0932-20937 (2007).
Cappuzzo et al., "Epidermal Growth Factor Receptor Gene and Protein and Gefilinib Sensitivity in Non-small-Cell ung Cancer," Journal of the National Cancer Institute, vol. 97, pp. 643-655 (2005).
Christensen et al., "c-Met as a target for human cancer and characterization of inhibitors for therapeutic ntervention," Cancer Letters, vol. 225, pp. 1-26 (2005).
Cooper et al., "Molecular cloning of a new transforming gene from a chemically transformed human cell line," Nature, vol. 311, pp. 29-33 (1984).
DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).
Downward et al., "Autophosphorylation sites on the epidermal growth factor receptor," Nature, vol. 311, pp. 183-485 ( 1984).
Engelman et al., "MET Amplification Leads to Gefitinib Resistance in Lung Cancer by Activating ERBB3 Signaling," Science, vol. 316, pp. 1039-1043 (2007).
Ferguson, Kathryn M., "Structure-Based View of Epidermal Growth Factor Receptor Regulation," Annual Review of Biophysics, vol. 37, pp. 535-373 (2008).
GenBank Accession No. NP 001120972.
Alfthan et al., "Properties of a single-chain antibody containing different linker peptides," Protein Engineering, vol. B, No. 7, pp. 725-731 (1995).
Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).
Bork et al., "Proposed acquisition of an animal protein domain by bacteria," Proceedings of the National Academy of Science, USA, vol. 89, pp. 8990-8994 (1992).
Hallewell et al., "Genetically Engineered Polymers of Human CuZN Superoxide Dismutase," The Journal of Biological Chemistry, vol. 264, No. 9, pp. 5260-5268 (1989).
Hanes et al, "In vitro selection and evolution of functional proteins by using ribosome display," Proceedings of the National Academy of Sciences USA, vol. 94, pp. 4937-4942 (1997).
Jacobs et al., "Design of novel FN3 domains with high stability by a consensus sequence approach," Protein Engineering, Design & Selection, vol. 25, No. 3, pp. 107-117 (2012).
Diem et al., "Selection of high-affinity Centyrin FN3 domains from a simply library diversified at a combination of strand and loop positions." Protein Engin Design (2014) Selection 27(10): 419-429.
Tannock and Hill. The Basic Science of Oncology. 1998. New York: McGraw-Hill;; pp. 357-358.
Song et al. Cancer stem cells—an old idea that's new again: implications for the diagnosis and treatment of breast cancer. Expert Opin Biol Ther 7:4):431-438, 2007.
Binz et al., "High-affinity binders selected from designed ankyrin repeat protein libraries," Nature Biotechnology, vol. e2, No. 5, pp. 575-582 (May 2004).
Garon et al., "Pembrolizumab for the Treatment of Non-Small-Cell Lung Cancer," The New England Journal of Medicine, vol. 372, No. 21, pp. 2018-2028 (May 21, 2015).
Koide et al., "High-affinity single-domain binding proteins with a binary-code interface," PNAS, vol. 104, No. 16, pp. 6632-6637(Apr. 17, 2017).
Lepenies et al., "The Role of Negative Costimulators Dunng Parasitic Infections," Endocrine, Metabolic & Immune Disorders—Drug Targets, vol. 8, pp. 279-288 (2008).
McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).
Meinke et al., "Cellulose-Binding Polypeptides from Cellulomonas fimi: Endoglucanase D (CenD), a Family A b-1,4-Glucanase," Journal of Bacteriology, vol. 175, No. 7, pp. 1910-1918 (1993).
Odegrip et al., "CIS display: In vitro selection of peptides from libraries of protein-DNA complexes," Proceedings of he National Academy of Science USA, vol. 101, No. 9, pp. 2806-2810 (2004).
Olson et al., "Design, expression, and stability of a diverse protein library based on the human fibronectin type III ô €,?omain," Protein Science, vol. 16, pp. 476-484 (2007).
Roberts et al., "RNA-peptide fusions for the in vitro selection of peptides and proteins," Proceedings of the National Academy of Science USA, vol. 94, pp. 12297-12302 (1997).
Robinson et al., "Covalent Attachment of Arc Repressor Subunits by a Peptide Linker Enhances Affinity for Operator DNA," Biochemistry, vol. 35, pp. 109-116 (1996).
Strohl, William R., "Optimization of Fe-mediated effector functions of monoclonal antibodies," Current Opinion in Biotechnology, vol. 20, pp. 685-691 (2009).
Tie et al., "Safety and efficacy of nivolumab in the treatment of cancers: A meta-analysis of 27 prospective clinical rials," International Journal of Cancer, vol. 140, pp. 948-958, (2017).
Wang et al., "Vista, a novel mouse Ig superfamily ligand that negatively regulates T cell responses," Journal of Experimental Medicine, vol. 208, No. 3, pp. 577-592 (Mar. 14, 2011).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Cooper et al., "4-1 BB (CD 137) controls the clonal expansion and survival of COB T cells in vivo but does not t: ontribute the development of cytotoxicity", Eur. J_ Immunol., vol. 32, pp. 521-529, 2002.
Gramaglia et al., "Co-stimulation of antigen-specific CD4 T cells by 4-1BB ligand," Eur. J. Immunol., vol. 30, pp. ô €?˜92-402 (2000).
DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).
Langstein et al., "CD137 Induces Proliferation and Endomitosis in Monocytes," Blood, vol. 94, No. 9, pp. 3161-3168 1999).
Langstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).
Lee et al., "4-1BB Promotes the Survival of COB+ T Lymphocytes by Increasing Expression of Bcl-xL and Bfl-11," The Journal of Immunol., vol. 169, pp. 4882-4888 (2002).
Michel et al., "A soluble form of CD137 (ILA/4-1BB), a member of the TNF receptor family, is released by activated ymphocytes and is detectable in sera of patients with rheumatoid arthritis," Eur. J_ Immunol., vol. 28, pp. 290-295 1998).
Michel et al., "CD137-induced apoptosis is independent of CD95," Immunology, vol. 98, pp. 42-46 (1999).
Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).
Shuford et al., "4-18B Costimulatory Signals Preferentially Induce COB+ T Cell Proliferation and Lead to the amplification In Vivo of Cytotoxic T Cell Responses," J_ Exp_ Med., vol. 186, No. 1, pp. 47-55 (Jul. 7, 1997).
Takahashi et al., "Cutting Edge: 4-1 BB Is a Bona Fide COB T Cell Survival Signal," J Immunol., vol. 162, pp. 0037-5040 (1999).
Alderson et al., "Molecular and Biological Characterization of Human 4-1 BB and its Ligand", Eur. J_ Immunol., vol. N, pp. 2219-2227, 1994.

(56) References Cited

OTHER PUBLICATIONS

Hurtado et al., "Potential role of 4-1 BB in T cell Activation Comparison with the Costimulatory Molecule CD28", Journal of Immunology, vol. 155, pp. 3360-3367, 1995.
Hurtado et al., "Signals through 4-1BB are Costimulatory to previously activated splenic T cells and inhibit activation-induced cell death", Journal of Immunology, vol. 158, pp. 2600-2609, 1997.
Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.
Michel et al., "Expression of soluble CD137 correlates with activation-induced cell death of lymphocytes", Cytokine, vol. 12, No. 6, pp. 742-746, 2000.
Zhou et al., Characterization of human homologue of 4-1 BB and its ligand, Immunology Letters, vol. 45, pp. p7-73, 1995.
Pauly et al., CD137 is expressed by follicular dendritic cells and costimulates B lymphocyte activation in germinal t: enters, Journal of Leukocyte Biology, vol. 72, pp. 35-42, Jul. 2002.
Langstein et al., Identification of CD137 as a potent monocyte survival factor, Journal of Leukocyte Biology, vol. 65, pp. 829-833, Jun. 1999.
Kwon et al., cDNA sequences of two inducible T-cell genes, Proc. Natl. Acad. Sci., vol. 86, pp. 1963-1967, Mar. 1989.
Lehmann et al., Engineering proteins for thermostability the use of sequence alignments versus rational design and directed evolution, Current Opinion in Biotechnology, vol. 12, pp. 371-375 (2001).
Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.
Goldberg et al., "Engineering a Targeted Delivery Platform using Centyrins" Protein Engineering, Design & selection, vol. 29, No. 12, pp. 563-572, 2016.
Strand et al., "Site-Specific Radioiodination of HER2-Targeting Affibody Molecules using 4-lodophenethylmaleimide Decreases Renal Uptake of Radioactivity"; Chemitry Open, vol. 4, pp. 174-182, 2015.
Hylarides et al., "Preparation and in Vivo Evaluation of an N-9p-[125I]1odophenethyl) maleimide—Antibody Conjugate" Bioconjugate Chem., vol. 2, pp. 435-440, 1991.
Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.
Binz, et al., "Engineered proteins as specific binding reagents," Current Opinion in Biotechnology, 16: 459-469 (2005).
Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity," The Journal Jf Biological Chemistry, vol. 259, No. 12, pp. 7755-7760 (1984).
Goldstein et al., "Biological efficacy of a chimeric antibody to the epidermal growth factor receptor in a human umor xenografl model," Clinical Cancer Research, vol. 1, pp. 1311-1318 (1995).
Grünwald et al., "Developing Inhibitors of the Epidermal Growth Factor Receptor for Cancer Treatment," Journal of he National Cancer Institute, vol. 95, No. 12, pp. 851-867 (2003).
Hirsch et al, "Combination of EGFR gene copy number and protein expression predicts outcome for advanced non- , mall-cell lung cancer patients treated with gefitnib," Annals of Oncology, vol. 18, pp. 752-760 (2007).
Hynes et al., "ERBB Receptors and Cancer: the Complexity of Targeted Inhibitors," Nature Reviews, vol. 5, pp. 341-356 (2005).
Chimu RA et al., "Expression of c-mel/HGF Receptor in Human Non-small Cell Lung Carcinomas in vitro and in vivo and Its Prognostic Significance," Japan Journal of Cancer Research, vol. 87. pp. 1063-1069 (1996).
Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).
Jacobs et al., "FN3 Domain Engineering", Protein Engineering, pp. 145-162, 2012.
Li et al., "Skin toxicities associated with epidermal growth factor receptor inhibitors," Target Oncology, vol. 4, pp. 107-119 (2009).
Linardou et al., "Somatic EGFR mutations and efficacy of tyrosine kinase inhibitors in NSCLC," National Review of :; linical Oncology, vol. 6, pp. 352-366 (2009).
Ma et al., "c-Met: Structure, functions and potential for therapeutic inhibition," Cancer and Metastasis Reviews, vol. 22 pp. 309-325 (2003).
Mendelsohn et al., "Epidermal Growth Factor Receptor Targeting in Cancer," Seminars in Oncology, vol. 33, pp. 369-385 (2006).
Mendelsohn et al., "The EGF receptor family as targets for cancer therapy," Oncogene, vol. 19, pp. 6550-6565 2000).
Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).
NCBI Reference Sequence NP _005219.2, "Epidermal Growth Factor Receptor Isoform a Precursor [Homo sapiens]," pp. 1-14 (May 18, 2014).
Panek et al.,"In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth Jf Human Renal Cell Carcinoma Xenografts in Nude Mice," Clinical Cancer Research, vol. 4, pp. 2957-2966 (1998).
Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-g844 (2006).
Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).
Schmidt et al., "Novel mutations of the MET proto-0ncogene in papillary rental carcinomas," Oncogene, vol. 18, pp. ]343-2350 (1999).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-MET as a potential therapeutic target and biomarker in cancer," Therapeutic Advances in Medical :: >ncology, vol. 3, No. 51, pp. 521-535 (2011).
Stamos et al., "Crystal structure of the HGF b-chain in complex with the Serna domain of the Met receptor," The EMBO Journal, vol. 23, pp. 2325-2335 (2004).
Mamluk et al., "Anti-tumor effect of CT-322 as an Adnectin inhibitor of vascular endothelial growth factor receptor-2", mAbs, 2(2), pp. 199-208, 2010.
Klein et al. "Abstract LB-312: Bispecific Centyrin Simultaneously targeting EGFR and c-Met demonstrates improved ô €?'ctivity compared to the mixture of single agents", Cancer Research, 73 (8 Supplement), Abstract LB-312, Apr. 2013.
Jacobs et al., "Fusion to a highly stable consensus albumin binding domain allows for tunable pharmacokinetics", Protein Engineering, Design & Selection, vol. 28, No. 10, pp. 385-393, 2015.
Notice of Allowance dated Mar. 3, 2020 in U.S. Appl. No. 15/840,303.
Makkouk Amani et al: "Rationale for anti-CD137 cancer immunotherapy", European Journal of Cancer, Elsevier, Amsterdam, NL, vol. 54, Jan. 2, 2016 (Jan. 2, 2016), pp. 112-119, XP029401784, ISSN: 0959-8049, DOI: 10.1016/j.ejca.2015.09.026 *abstractp. 114, right-hand column, paragraph 4—p. 116, right-hand column, paragraph 1table 1*.
Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-

(56) References Cited

OTHER PUBLICATIONS

0126, DOI: 10.1093/protein/gzw054 *abstractp. 564, left-hand column, paragraph 2—right-hand column, line 3 p. 567, right-hand column, paragraph 2p. 568, right-hand column, paragraph 2—p. 569, left-hand column, paragraph 2table I**figure 1a*.

Burton Earle Barnett et al: "Disclosures", Blood, vol. 128, No. 22, Dec. 2, 2016 (Dec. 2, 2016), pp. 4557-4557, XP055711182, US ISSN: 0006-4971, doi: 10.1182/blood.V128.22.4557.4557 *abstract*.

Final Office Action dated Jul. 10, 2020 in U.S. Appl. No. 15/637,276.

Zucali, et al., "Role of cMET expression in non-small-cell lung cancer patients treated with eGFR tyrosine kinase inhibitors", Annals of Anocology (2008) 19:: 1605-1612.

Non-Final Office Action dated Sep. 24, 2021 in U.S. Appl. No. 16/820,844.

Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.

Non-Final Office Action dated Feb. 3, 2021 in U.S. Appl. No. 16/218,990.

Final Office Action dated Jul. 21, 2020 in U.S. Appl. No. 16/218,990.

Lejon et al., "Structural basis for the binding of naproxen to human serum albumin in the presence of fatty acids and the GA module", Acta Cryst. (2008) F pp. 64-69.

Lee et al., "A Glu-ruea-Lys Ligand-conjugated Lipid nanoparticle/siRNA System Inhibits Androgen Receptor Expression In Vivo", Molecular Therapy—Nucleic Acids (2016) 5, e348: pp. 1-11.

Pace, "Determination and Analysis of Urea and Guanidine Hydrochloride Denaturation Curves", Methods in Enzymology (1986) vol. 131, pp. 266-280.

Chen et al., "Cell-Surface Display of Heterologous Proteins: From High-Throughput Screening to Environmental Applications", Biotechnology and Bioengineering, (2002) vol. 79, No. 5, pp. 496-503.

Mattheakis et al., "An in vitro polysome display system for identifying ligands from very large peptide libraries", Proc. Natl. Acad. Sci. (1994) Vo.. 91, pp. 9022-9026.

Hoogenboom et al., "Natural and designer binding sites made by phage display technology" Immunology Today (2000) vol. 21, No. 8, pp. 371-378.

Smith, "Filamentous fusion phage: novel expression vectors that display cloned antigens on the virion surface.", Association of Science (1985) vol. 228, pp. 1315(3).

Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.

Itoh, et al., "Application of Inverse Substrates to Trypsin-Catalyzed Peptide Synthesis", Bioorganic Chemistry (1996) 24, 0007, pp. 59-68.

Kumaran et al., "Confrmationally driven protease-catalyzed splicing of peptide segments: V8 protease-mediated syntheses of fragments derived from thermolysin and ribonuclease A", Protein Science, (1997) 6: pp. 2233-2241.

Kunkel et al., "Rapid and Efficient Site-Specific Mutagenesis without Phenotypic Selection", Methods in Enzymology, (1987) vol. 154 pp. 367-375.

Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.

Hackel et al., "Use of 64Cu-Labeled Fibronectin Domain with EGFR-Overexpressing Tumor Xenograft: Molecular Imaging1", Radiology (2012) vol. 263:No. 1 pp. 179-188.

Non-Final Office Action dated Aug. 18, 2021 in U.S. Appl. No. 16/801,787.

McCracken, "Non-invasive monitoring of hematopoietic reconstitution and immune cell function through Positron Emission Tomography" University of California, Los Angeles, Dissertaton ProQuest LLC (2014) pp. 1-202.

Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.

* cited by examiner

SEQUENCE LISTING

<160> NUMBER OF SEQ ID NOS: 281

<210> SEQ ID NO 1
<211> LENGTH: 89
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly His Arg Arg Ser
65                  70                  75                  80

Asn Pro Leu Ser Ala Glu Phe Thr Thr
                85

<210> SEQ ID NO 2
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(81)
<223> OTHER INFORMATION: Any amino acid
<220> FEATURE:
<221> NAME/KEY: MOD_RES
<222> LOCATION: (82)..(86)
<223> OTHER INFORMATION: Any amino acid or absent

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (23)..(23)
<223> OTHER INFORMATION: Ala, Arg, Asn, Asp, Glu, Gln, Gly, His, Ile,
```

-continued

```
      Leu, Lys, Phe, Pro, Ser, Thr, Trp, Tyr or Val
<220> FEATURE:
<221> NAME/KEY: MOD_RES
<222> LOCATION: (24)..(24)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (25)..(25)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (26)..(26)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (27)..(27)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (28)..(28)
<223> OTHER INFORMATION: Phe, Ile, Leu, Val or Tyr
<220> FEATURE:
<221> NAME/KEY: MOD_RES
<222> LOCATION: (29)..(29)
<223> OTHER INFORMATION: Asp, Glu or Thr
<220> FEATURE:
<221> NAME/KEY: MOD_RES
<222> LOCATION: (75)..(75)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (76)..(76)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (77)..(77)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (78)..(78)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (79)..(79)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (81)..(81)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (82)..(82)
<223> OTHER INFORMATION: Ala, Arg, Asn, Asp, Glu, Gln, Gly, His, Ile,
      Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60
```

```
Thr Glu Tyr Thr Val Ser Ile Tyr Gly Val Xaa Xaa Xaa Xaa Ser
 65                  70                  75                  80

Xaa Xaa Leu Ser Ala Glu Phe Thr Thr
                 85

<210> SEQ ID NO 4
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Leu
             20                  25                  30

Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Lys Gly His Arg Ser
 65                  70                  75                  80

Asn Pro Leu Ser Ala Ile Phe Thr Thr
                 85

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(27)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (28)..(30)
<223> OTHER INFORMATION: Ala, Asp, Glu, Phe, Gly, His, Ile, Lys, Leu,
      Asn, Pro, Gln, Arg, Ser, Thr, Val, Trp, Tyr, or absent
<220> FEATURE:
<221> NAME/KEY: MOD_RES
<222> LOCATION: (78)..(84)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (85)..(87)
<223> OTHER INFORMATION: Ala, Asp, Glu, Phe, Gly, His, Ile, Lys, Leu,
      Asn, Pro, Gln, Arg, Ser, Thr, Val, Trp, Tyr, or absent

<400> SEQUENCE: 5

Leu Pro Ala Pro Lys Asn Leu Val Val Ser Arg Val Thr Glu Asp Ser
 1               5                  10                  15

Ala Arg Leu Ser Trp Xaa Xaa Xaa Xaa Xaa Xaa Xaa Xaa Phe Asp
             20                  25                  30

Ser Phe Leu Ile Gln Tyr Gln Glu Ser Glu Lys Val Gly Glu Ala Ile
             35                  40                  45

Val Leu Thr Val Pro Gly Ser Glu Arg Ser Tyr Asp Leu Thr Gly Leu
     50                  55                  60

Lys Pro Gly Thr Glu Tyr Thr Val Ser Ile Tyr Gly Val Xaa Xaa Xaa
```

```
                65                  70                  75                  80
Xaa Xaa Xaa Xaa Xaa Xaa Xaa Ser Asn Pro Leu Ser Ala Ile Phe Thr
                    85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(81)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (82)..(86)
<223> OTHER INFORMATION: Ala, Asp, Glu, Phe, Gly, His, Ile, Lys, Leu,
      Asn, Pro, Gln, Arg, Ser, Thr, Val, Trp, Tyr, or absent

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
```

-continued

```
<220> FEATURE:
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, Trp, Tyr, or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Xaa Val Xaa Ile Xaa Gly Val Lys Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (46)..(46)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (48)..(48)
<223> OTHER INFORMATION: Ala, Asp, Glu, Phe, Gly, His, Ile, Lys, Leu,
      Asn, Pro, Gln, Arg, Ser, Thr, Val, or Trp
```

```
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (84)..(84)
<223> OTHER INFORMATION: Ala, Asp, Glu, Phe, Gly, His, Ile, Lys, Leu,
      Asn, Pro, Gln, Arg, Ser, Thr, Val, or Trp
<220> FEATURE:
<221> NAME/KEY: MOD_RES
<222> LOCATION: (86)..(86)
<223> OTHER INFORMATION: Ala, Asp, Glu, Phe, Gly, His, Ile, Lys, Leu,
      Asn, Pro, Gln, Arg, Ser, Thr, Val, or Trp

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgacacggc ggttagaac                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
```

```
gcctttggga agcttctaag                                                    20

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cggcggttag aacgcggcta caattaatac                                         30

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catgattacg ccaagctcag aa                                                 22

<210> SEQ ID NO 13
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(224)
<223> OTHER INFORMATION: a, c, t, g, unknown or other

<400> SEQUENCE: 13
gtgacacggc ggttagaacg cggctacaat taatacataa ccccatcccc ctgttgacaa        60
ttaatcatcg gctcgtataa tgtgtggaat tgtgagcgga taacaatttc acacaggaaa       120
caggatctac catgctgccg gcgccgaaaa acctggttgt ttctgaagtt accgaagact       180
ctctgcgtct gtcttggnnn nnnnnnnnnn nnnnnnnnnn nnnnttygac tctttcctga       240
tccagtacca ggaatctgaa aaagttggtg aagcgatcaa cctgaccgtt ccgggttctg       300
aacgttctta cgacctgacc ggtctgaaac cgggtaccga atacaccgtt tctatctacg       360
gtgttcttag aagcttccca aaggc                                             385

<210> SEQ ID NO 14
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(221)
<223> OTHER INFORMATION: a, c, t, g, unknown or other

<400> SEQUENCE: 14
gtgacacggc ggttagaacg cggctacaat taatacataa ccccatcccc ctgttgacaa        60
ttaatcatcg gctcgtataa tgtgtggaat tgtgagcgga taacaatttc acacaggaaa       120
caggatctac catgctgccg gcgccgaaaa acctggttgt ttctgaagtt accgaagact       180
```

```
ctctgcgtct gtcttggnnn nnnnnnnnnn nnnnnnnnnn nttygactct ttcctgatcc    240
agtaccagga atctgaaaaa gttggtgaag cgatcaacct gaccgttccg ggttctgaac    300
gttcttacga cctgaccggt ctgaaaccgg gtaccgaata caccgtttct atctacggtg    360
ttcttagaag cttcccaaag gc                                              382
```

<210> SEQ ID NO 15
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(218)
<223> OTHER INFORMATION: a, c, t, g, unknown or other

<400> SEQUENCE: 15

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg cgccgaaaa acctggttgt ttctgaagtt accgaagact    180
ctctgcgtct gtcttggnnn nnnnnnnnn nnnnnnntt ygactctttc ctgatccagt    240
accaggaatc tgaaaaagtt ggtgaagcga tcaacctgac cgttccgggt tctgaacgtt    300
cttacgacct gaccggtctg aaaccgggta ccgaatacac cgtttctatc tacggtgttc    360
ttagaagctt cccaaaggc                                                 379
```

<210> SEQ ID NO 16
<211> LENGTH: 376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(215)
<223> OTHER INFORMATION: a, c, t, g, unknown or other

<400> SEQUENCE: 16

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg cgccgaaaa acctggttgt ttctgaagtt accgaagact    180
ctctgcgtct gtcttggnnn nnnnnnnnn nnnnttyga ctctttcctg atccagtacc    240
aggaatctga aaagttggt gaagcgatca acctgaccgt tccgggttct gaacgttctt    300
acgacctgac cggtctgaaa ccgggtaccg aatacaccgt ttctatctac ggtgttctta    360
gaagcttccc aaaggc                                                    376
```

<210> SEQ ID NO 17
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
cggcggttag aacgcggcta caattaatac ataaccccat cccctgttg acaattaatc     60
```
atcggctcgt ataatgtgtg gaattgtgag cggataacaa tttcacacag gaaacaggat        120
ctaccatgct g                                                            131

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggcggttag aacgcggcta caattaatac                                         30

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccaagacaga cgggcagagt cttcggtaac gcgagaaaca accaggtttt tcggcgccgg        60
cagcatggta gatcctgttt c                                                  81

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccgaagactc tgcccgtctg tcttgg                                             26

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagtggtctc acggattcct ggtactggat caggaaagag tcgaa                        45

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catgcggtct cttccgaaaa agttggtgaa gcgatcgtcc tgaccgttcc gggt              54

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggtggtgaag atcgcagaca gcgggttag                              29

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggcggttag aacgcggcta c                                      21

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagatcagtt gcggccgcta gactagaacc gctgccaccg ccggtggtga agatcgcaga    60
c                                                                  61

<210> SEQ ID NO 26
<211> LENGTH: 485
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(392)
<223> OTHER INFORMATION: a, c, t, g, unknown or other

<400> SEQUENCE: 26
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn nnnnnnnnnn nntctaaccc gctgtctgcg atcttcacca   420
ccggcggtca ccatcaccat caccatggca gcggttctag tctagcggcc gcaactgatc   480
ttggc                                                              485

<210> SEQ ID NO 27
<211> LENGTH: 482
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(389)
<223> OTHER INFORMATION: a, c, t, g, unknown or other

<400> SEQUENCE: 27

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnnnnnt ctaacccgct gtctgcgatc ttcaccaccg     420
gcggtcacca tcaccatcac catggcagcg gttctagtct agcggccgca actgatcttg     480
gc                                                                    482
```

<210> SEQ ID NO 28
<211> LENGTH: 479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(386)
<223> OTHER INFORMATION: a, c, t, g, unknown or other

<400> SEQUENCE: 28

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnntcta acccgctgtc tgcgatcttc accaccggcg     420
gtcaccatca ccatcaccat ggcagcggtt ctagtctagc ggccgcaact gatcttggc     479
```

<210> SEQ ID NO 29
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(383)
<223> OTHER INFORMATION: a, c, t, g, unknown or other

<400> SEQUENCE: 29

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnntctaacc cgctgtctgc gatcttcacc accggcggtc     420
```

```
accatcacca tcaccatggc agcggttcta gtctagcggc cgcaactgat cttggc        476
```

<210> SEQ ID NO 30
<211> LENGTH: 473
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(380)
<223> OTHER INFORMATION: a, c, t, g, unknown or other

<400> SEQUENCE: 30

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnnnnn tctaacccgc tgtctgcgat cttcaccacc ggcggtcacc    420
atcaccatca ccatggcagc ggttctagtc tagcggccgc aactgatctt ggc           473
```

<210> SEQ ID NO 31
<211> LENGTH: 470
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(377)
<223> OTHER INFORMATION: a, c, t, g, unknown or other

<400> SEQUENCE: 31

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnntct aacccgctgt ctgcgatctt caccaccggc ggtcaccatc    420
accatcacca tggcagcggt tctagtctag cggccgcaac tgatcttggc               470
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Lys Gly Gly His Arg Ser Asn
1               5
```

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
aagaaggaga accggtatgc tgccggcgcc gaaaaac      37

<210> SEQ ID NO 34
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
gagccgccgc caccggttta atggtgatgg tgatggtgac caccggtggt gaagatcgca      60
gacag      65

<210> SEQ ID NO 35
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
130                 135                 140

Pro Ala Gly Ser Gly Ser Gly Ser Asp Tyr Lys Asp Asp Asp Asp Lys
145                 150                 155                 160

Asp Lys Thr His Thr Cys Pro Pro Cys Pro Ala Pro Glu Leu Leu Gly
                165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
```

```
                    210                 215                 220
His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
                260                 265                 270

Glu Lys Thr Ile Ser Lys Ala Lys Gly Gln Pro Arg Glu Pro Gln Val
                275                 280                 285

Tyr Thr Leu Pro Pro Ser Arg Asp Glu Leu Thr Lys Asn Gln Val Ser
            290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
                340                 345                 350

Asp Lys Ser Arg Trp Gln Gln Gly Asn Val Phe Ser Cys Ser Val Met
                355                 360                 365

His Glu Ala Leu His Asn His Tyr Thr Gln Lys Ser Leu Ser Leu Ser
            370                 375                 380

Pro Gly Lys
385

<210> SEQ ID NO 36
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
                100                 105                 110

Pro Ala Lys Pro Thr Thr Thr Pro Ala Pro Arg Pro Pro Thr Pro Ala
            115                 120                 125

Pro Thr Ile Ala Ser Gln Pro Leu Ser Leu Arg Pro Glu Ala Cys Arg
        130                 135                 140

Pro Ala Ala Gly Gly Ala Val His Thr Arg Gly Leu Asp Phe Ala Cys
145                 150                 155                 160

Asp Gly Gly Gly Gly Ser Asp Tyr Lys Asp Asp Asp Lys Gly Gly
                165                 170                 175
```

```
Gly Gly Ser His His His His His Asp Lys Thr His Thr Cys Pro
            180                 185                 190

Pro Cys Pro Ala Pro Glu Leu Leu Gly Gly Pro Ser Val Phe Leu Phe
            195                 200                 205

Pro Pro Lys Pro Lys Asp Thr Leu Met Ile Ser Arg Thr Pro Glu Val
            210                 215                 220

Thr Cys Val Val Val Asp Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Asn Ser Thr Tyr Arg Val Val Ser Val Leu Thr
                260                 265                 270

Val Leu His Gln Asp Trp Leu Asn Gly Lys Glu Tyr Lys Cys Lys Val
            275                 280                 285

Ser Asn Lys Ala Leu Pro Ala Pro Ile Glu Lys Thr Ile Ser Lys Ala
            290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
                325                 330                 335

Phe Tyr Pro Ser Asp Ile Ala Val Glu Trp Glu Ser Asn Gly Gln Pro
                340                 345                 350

Glu Asn Asn Tyr Lys Thr Thr Pro Pro Val Leu Asp Ser Asp Gly Ser
            355                 360                 365

Phe Phe Leu Tyr Ser Lys Leu Thr Val Asp Lys Ser Arg Trp Gln Gln
            370                 375                 380

Gly Asn Val Phe Ser Cys Ser Val Met His Glu Ala Leu His Asn His
385                 390                 395                 400

Tyr Thr Gln Lys Ser Leu Ser Leu Ser Pro Gly Lys
                405                 410

<210> SEQ ID NO 37
<211> LENGTH: 20
<212> TYPE: PRT
<213> ORGANISM: Unknown
<220> FEATURE:
<223> OTHER INFORMATION: Description of Unknown:
      mIgGK signal peptide

<400> SEQUENCE: 37

Met Glu Thr Asp Thr Leu Leu Leu Trp Val Leu Leu Leu Trp Val Pro
1               5                   10                  15

Gly Ser Thr Gly
            20

<210> SEQ ID NO 38
<211> LENGTH: 227
<212> TYPE: PRT
<213> ORGANISM: Homo sapiens

<400> SEQUENCE: 38

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45
```

```
Glu Asp Pro Glu Val Lys Phe Asn Trp Tyr Val Asp Gly Val Glu Val
 50                  55                  60
His Asn Ala Lys Thr Lys Pro Arg Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
210                 215                 220
Pro Gly Lys
225

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Gly Gly Ser Asp Tyr Lys Asp Asp Asp Asp Lys Gly Gly Gly
1               5                   10                  15
Gly Ser His His His His His His
            20

<210> SEQ ID NO 40
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Pro Ala Pro Lys Asn Leu Val Val Ser Arg Val Thr Glu Asp Ser
1               5                   10                  15
Ala Arg Leu Ser Trp His Thr Ala Thr Asn Ser Phe Asp Ser Phe Leu
            20                  25                  30
Ile Gln Tyr Gln Glu Ser Glu Lys Val Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Thr Val Ser Ile Tyr Gly Val Asp Val Asp Tyr Asn Pro
65                  70                  75                  80
```

```
Thr Gly Arg Pro Val Ser Ser Asn Pro Leu Ser Ala Ile Phe Thr Thr
                85                  90                  95
```

<210> SEQ ID NO 41
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Leu Pro Ala Pro Lys Asn Leu Val Val Ser Arg Val Thr Glu Asp Ser
1               5                   10                  15

Ala Arg Leu Ser Trp Val Lys Arg Pro Asn Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Val Asp Tyr Glu
65                  70                  75                  80

Gly Arg Pro Arg Trp Ser Asn Pro Leu Ser Ala Ile Phe Thr Thr
                85                  90                  95
```

<210> SEQ ID NO 42
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Leu Pro Ala Pro Lys Asn Leu Val Val Ser Arg Val Thr Glu Asp Ser
1               5                   10                  15

Ala Arg Leu Ser Trp Ser Lys Thr Asp Ser Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Val Tyr Ile Glu
65                  70                  75                  80

Gly Asn Pro Val Phe Ser Asn Pro Leu Ser Ala Ile Phe Thr Thr
                85                  90                  95
```

<210> SEQ ID NO 43
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Leu Pro Ala Pro Lys Asn Leu Val Val Ser Arg Val Thr Glu Asp Ser
1               5                   10                  15

Ala Arg Leu Ser Trp Pro Glu Gly Asp Arg Pro Phe Phe Asp Ser Phe
            20                  25                  30

Leu Ile Gln Tyr Gln Glu Ser Glu Lys Val Gly Glu Ala Ile Val Leu
```

```
                 35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Asp Val Lys Trp Glu
65                  70                  75                  80

Gly Asn Arg Pro Val Ala Ser Asn Pro Leu Ser Ala Ile Phe Thr Thr
                 85                  90                  95

<210> SEQ ID NO 44
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Pro Ala Pro Lys Asn Leu Val Val Ser Arg Val Thr Glu Asp Ser
1               5                   10                  15

Ala Arg Leu Ser Trp Thr Arg His Glu Thr Ser Phe Asp Ser Phe Leu
                 20                  25                  30

Ile Gln Tyr Arg Glu Ser Glu Lys Val Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Val Glu Tyr Asp Ala
65                  70                  75                  80

Ala Gly Asn Pro Lys Tyr Ser Asn Pro Leu Ser Ala Ile Phe Thr Thr
                 85                  90                  95

<210> SEQ ID NO 45
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Pro Ala Pro Lys Asn Leu Val Val Ser Arg Val Thr Glu Asp Ser
1               5                   10                  15

Ala Arg Leu Ser Trp Ile Pro Asn Pro Ser Ser Phe Asp Ser Phe Leu
                 20                  25                  30

Ile Gln Tyr Gln Glu Ser Glu Lys Val Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Asp Val Phe Asp Pro
65                  70                  75                  80

Val Gly Phe Pro Ser His Ser Asn Pro Leu Ser Ala Ile Phe Thr Thr
                 85                  90                  95

<210> SEQ ID NO 46
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

```
Leu Pro Ala Pro Lys Asn Leu Val Val Ser Arg Val Thr Glu Asp Ser
1               5                   10                  15

Ala Arg Leu Ser Trp Arg Lys Arg Ala Asn Ser Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Val Glu Tyr Asp Gln
65                  70                  75                  80

His Gly Arg Pro Arg Trp Ser Asn Pro Leu Ser Ala Ile Phe Thr Thr
                85                  90                  95
```

<210> SEQ ID NO 47
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Leu Pro Ala Pro Lys Asn Leu Val Val Ser Arg Val Thr Glu Asp Ser
1               5                   10                  15

Ala Arg Leu Ser Trp Lys Ala Asn Arg Thr Thr Asp Leu His Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Asp Val Gln
65                  70                  75                  80

Tyr Asp Gly Gln Gln Pro Leu Tyr Ser Asn Pro Leu Ser Ala Ile Phe
                85                  90                  95

Thr Thr
```

<210> SEQ ID NO 48
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Leu Pro Ala Pro Lys Asn Leu Val Val Ser Arg Val Thr Glu Asp Ser
1               5                   10                  15

Ala Arg Leu Ser Trp Asn Pro Ser Glu Asp Pro Gln Arg Phe Asp Ser
            20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95
```

Thr

<210> SEQ ID NO 49
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Pro Ala Pro Lys Asn Leu Val Val Ser Arg Val Thr Glu Asp Ser
1               5                   10                  15

Ala Arg Leu Ser Trp Trp Ser Asn Asp Asn Arg Pro Ile Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95

Thr

<210> SEQ ID NO 50
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Pro Ala Pro Asn Asn Leu Val Val Ser Arg Val Thr Glu Asp Ser
1               5                   10                  15

Ala Arg Leu Ser Trp Pro Phe Val Ser Gln Asn Lys Pro His Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 51
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Pro Ala Pro Lys Asn Leu Val Val Ser Arg Val Thr Glu Asp Ser
1               5                   10                  15

Ala Arg Leu Ser Trp Gly Gln Tyr Ile Thr Ala Phe Ser Phe Asp Ser

```
                    20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Asp Val Ala Trp
65                  70                  75                  80

Phe Gln Gly Lys Pro Thr Trp Ser Asn Pro Leu Ser Ala Ile Phe Thr
                85                  90                  95

Thr

<210> SEQ ID NO 52
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Leu Pro Ala Pro Lys Asn Leu Val Val Ser Arg Val Thr Glu Asp Ser
1               5                   10                  15

Ala Arg Leu Ser Trp Ile Lys Asp Gly His Pro Arg His Phe Asp Ser
            20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Asp Val Val Tyr
65                  70                  75                  80

Asp Arg Gly Gln Leu Ile Ser Ser Asn Pro Leu Ser Ala Ile Phe Thr
                85                  90                  95

Thr

<210> SEQ ID NO 53
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Leu Pro Ala Pro Lys Asn Leu Val Val Ser Arg Val Thr Glu Asp Ser
1               5                   10                  15

Ala Arg Leu Ser Trp Trp Pro Arg Lys Tyr Gln Arg Pro Phe Asp Ser
            20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Asp Ile Glu Trp
65                  70                  75                  80

Ile Gly Asn Arg Pro Ile Ala Ser Asn Pro Leu Ser Ala Ile Phe Thr
                85                  90                  95

Thr
```

-continued

```
<210> SEQ ID NO 54
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Pro Ala Pro Lys Asn Leu Val Val Ser Arg Val Thr Glu Asp Ser
1               5                   10                  15

Ala Arg Leu Ser Trp Pro Ile Ala Ser Gln Ile His Ser Pro Phe Asp
            20                  25                  30

Ser Phe Leu Ile Gln Tyr Gln Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Tyr Asp Ile Asp Ser Arg Pro Ile Ser Ser Asn Pro Leu Ser Ala Ile
                85                  90                  95

Phe Thr Thr

<210> SEQ ID NO 55
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Leu Pro Ala Pro Lys Asn Leu Val Val Ser Arg Val Thr Glu Asp Ser
1               5                   10                  15

Ala Arg Leu Ser Trp Lys Lys Arg Glu Tyr Gln Asp Pro Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 56
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
            20                  25                  30

Ile Ala Tyr Pro Glu Trp Pro Ser Asn Gly Glu Ala Ile Val Leu Thr
```

```
                35                  40                  45
Val Pro Gly Ser Glu Arg Ser Tyr Asp Leu Thr Gly Leu Lys Pro Gly
 50                  55                  60

Thr Glu Tyr Ala Val Phe Ile Trp Gly Val Lys Gly Gly Ala Phe Ser
 65                  70                  75                  80

Asn Pro Leu Ser Ala Ile Phe Thr Thr
                 85

<210> SEQ ID NO 57
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Leu
                 20                  25                  30

Ile Ala Tyr Pro Glu Trp Pro Asp Ser Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Ala Val Phe Ile Trp Gly Val Lys Gly Gly Pro Leu Ser
 65                  70                  75                  80

His Pro Leu Ser Ala Ile Phe Thr Thr
                 85

<210> SEQ ID NO 58
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Leu
                 20                  25                  30

Ile Ser Tyr Pro Glu Tyr Pro Pro Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Phe Val Ile Ile Phe Gly Val Lys Gly Gly Asp Thr Ser
 65                  70                  75                  80

Trp Pro Leu Ser Ala Ile Phe Thr Thr
                 85

<210> SEQ ID NO 59
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Ala Tyr Pro Glu Trp Pro Ile Phe Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Val Ile Tyr Gly Val Lys Gly Gly Glu Gln
65                  70                  75                  80

Ser Ser Pro Leu Ser Ala Ile Phe Thr Thr
            85                  90
```

<210> SEQ ID NO 60
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ser Tyr Pro Glu Trp Pro Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Trp Gly Val Lys Gly Gly Glu Thr Ser
65                  70                  75                  80

Ala Pro Leu Ser Ala Ile Phe Thr Thr
            85
```

<210> SEQ ID NO 61
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Leu Pro Ala Pro Lys Asn Leu Val Val Ser Arg Val Thr Glu Asp Ser
1               5                   10                  15

Ala Arg Leu Ser Trp Thr Ala Pro Glu Ala Ala Phe Asp Ser Phe Gln
            20                  25                  30

Ile Ala Tyr Pro Glu Trp Pro Pro Arg Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Gln Gly Val Lys Gly Gly Glu Ile Ser
65                  70                  75                  80

Trp Pro Leu Ser Ala Ile Phe Thr Thr
            85
```

<210> SEQ ID NO 62

```
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
                20                  25                  30

Ile Gly Tyr Pro Glu Leu Glu Lys Leu Gly Tyr Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Trp Val Ile Ile Trp Gly Val Lys Gly Gly Glu
65                  70                  75                  80

Asn Ser Trp Pro Leu Ser Ala Ile Phe Thr Thr
                85                  90

<210> SEQ ID NO 63
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
                20                  25                  30

Ile Ala Tyr Pro Glu Trp Pro Val Gln Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Ile Ile Tyr Gly Val Lys Gly Gly Glu Leu Ser
65                  70                  75                  80

Pro Pro Leu Ser Ala Ile Phe Thr Thr
                85

<210> SEQ ID NO 64
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Ala Tyr Thr Glu Trp Pro Ile Pro Tyr Glu Glu Ala Gly Gln Glu
            35                  40                  45

Gly Glu Ala Ile Val Leu Thr Val Pro Gly Ser Glu Arg Ser Tyr Asp
        50                  55                  60
```

Leu Thr Gly Leu Lys Pro Gly Thr Glu Tyr Trp Val Ser Ile Tyr Gly
65                  70                  75                  80

Val Lys Gly Gly Pro Asn Ser Gln Pro Leu Ser Ala Ile Phe Thr Thr
            85                  90                  95

<210> SEQ ID NO 65
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Val Tyr Pro Glu Trp Pro Thr Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Phe Ile Trp Gly Val Lys Gly Gly Asn Gln Ser
65                  70                  75                  80

Trp Pro Leu Ser Ala Ile Phe Thr Thr
            85

<210> SEQ ID NO 66
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
            20                  25                  30

Ile Ala Tyr Pro Glu Phe Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Ile Ile Ile Gly Val Lys Gly Gly Thr Asp Ser
65                  70                  75                  80

Trp Pro Leu Ser Ala Ile Phe Thr Thr
            85

<210> SEQ ID NO 67
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr

```
                    20                  25                  30

Ile Ser Tyr Pro Glu Trp Pro Val Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Val Ile Tyr Gly Val Lys Gly Gly Ala Leu Ser
65                  70                  75                  80

Val Pro Leu Ser Ala Ile Phe Thr Thr
                85
```

<210> SEQ ID NO 68
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Thr Tyr Pro Glu Trp Pro Asp Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90
```

<210> SEQ ID NO 69
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Pro Glu Thr Ala Thr Trp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Ile Ile Tyr Gly Val Lys Gly Gly Phe Glu Ser
65                  70                  75                  80

Ala Pro Leu Ser Ala Ile Phe Thr Thr
                85
```

<210> SEQ ID NO 70
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ser Tyr Pro Glu Trp Pro Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Tyr Gly Val Lys Gly Gly Ala Ile Ser
65                  70                  75                  80

Thr Pro Leu Ser Ala Ile Phe Thr Thr
                85

<210> SEQ ID NO 71
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Phe Tyr Pro Glu Ile Val Thr Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Asn Ile Val Gly Val Lys Gly Gly Asp Asn Ser
65                  70                  75                  80

Trp Pro Leu Ser Ala Ile Phe Thr Thr
                85

<210> SEQ ID NO 72
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Leu Pro Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Gly Val Glu Ser
65                  70                  75                  80

Phe Pro Leu Ser Ala Ile Phe Thr Thr
                85

<210> SEQ ID NO 73
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ser Tyr Pro Glu Trp Pro Val Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Gly Leu Tyr Ser
65                  70                  75                  80

Ala Pro Leu Ser Ala Ile Phe Thr Thr
                85

<210> SEQ ID NO 74
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ala Tyr Pro Glu Trp Pro Val Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Gln Gly Val Lys Gly Gly Thr Pro Ser
65                  70                  75                  80

Trp Pro Leu Ser Ala Ile Phe Thr Thr
                85

<210> SEQ ID NO 75
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Trp Pro Val Ile Gly Glu Ala Ile Val Leu Thr
        35                  40                  45

```
Val Pro Gly Ser Glu Arg Ser Tyr Asp Leu Thr Gly Leu Lys Pro Gly
    50                  55                  60

Thr Glu Tyr Trp Val Ile Ile Gln Gly Val Lys Gly Gly Tyr Thr Ser
 65                  70                  75                  80

Trp Pro Leu Ser Ala Ile Phe Thr Thr
                85
```

<210> SEQ ID NO 76
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Asp
                 20                  25                  30

Ile Phe Tyr Pro Glu Leu Pro Ile His Gly Glu Ala Ile Val Leu Thr
             35                  40                  45

Val Pro Gly Ser Glu Arg Ser Tyr Asp Leu Thr Gly Leu Lys Pro Gly
    50                  55                  60

Thr Glu Tyr Trp Val Asn Ile Thr Gly Val Lys Gly Gly Asp Phe Ser
 65                  70                  75                  80

Trp Pro Leu Ser Ala Ile Phe Thr Thr
                85
```

<210> SEQ ID NO 77
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Asn
                 20                  25                  30

Ile Ala Tyr Pro Glu Ala Leu His Pro Gly Tyr Gly Glu Ala Ile Val
             35                  40                  45

Leu Thr Val Pro Gly Ser Glu Arg Ser Tyr Asp Leu Thr Gly Leu Lys
    50                  55                  60

Pro Gly Thr Glu Tyr Trp Val Ile Ile Gly Gly Val Lys Gly Gly Gln
 65                  70                  75                  80

Lys Ser Trp Pro Leu Ser Ala Ile Phe Thr Thr Gly Gly His His His
                 85                  90                  95

Asp His His
```

<210> SEQ ID NO 78
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Thr Tyr Pro Glu Trp Pro Val Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Tyr Gly Val Lys Gly Thr Glu Ser
65                  70                  75                  80

Glu Pro Leu Ser Ala Ile Phe Thr Thr
                85
```

```
<210> SEQ ID NO 79
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Val Glu Ser
65                  70                  75                  80

Trp Pro Leu Ser Ala Ile Phe Thr Thr
                85
```

```
<210> SEQ ID NO 80
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Thr Thr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Trp Gly Val Lys Gly Gly Asp His Ser
65                  70                  75                  80

Ala Pro Leu Ser Ala Ile Phe Thr Thr
                85
```

```
<210> SEQ ID NO 81
```

<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Trp Pro Pro Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Ser Tyr Ser
65                  70                  75                  80

Ala Pro Leu Ser Ala Ile Phe Thr Thr
                85

<210> SEQ ID NO 82
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Ala Tyr Pro Glu Trp Pro Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Pro Glu Tyr Phe Val Val Ile Gln Gly Val Lys Gly Gly Asp Pro Ser
65                  70                  75                  80

Phe Pro Leu Ser Ala Ile Phe Thr Thr Gly Gly Asn His His His His
                85                  90                  95

His

<210> SEQ ID NO 83
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys

```
                50                  55                  60

Pro Gly Thr Glu Tyr Trp Val Pro Ile Trp Gly Val Lys Gly Ala
 65                  70                  75                  80

Asn Ser Trp Pro Leu Ser Ala Ile Phe Thr Thr
                 85                  90

<210> SEQ ID NO 84
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asn
                20                  25                  30

Ile Ala Tyr Pro Glu Ala Leu His Pro Gly Tyr Gly Glu Ala Ile Val
             35                  40                  45

Leu Thr Val Pro Gly Ser Glu Arg Ser Tyr Asp Leu Thr Gly Leu Lys
         50                  55                  60

Pro Gly Thr Glu Tyr Phe Val Val Ile Tyr Gly Val Lys Gly Gly Thr
 65                  70                  75                  80

Asn Ser Glu Pro Leu Ser Ala Ile Phe Thr Thr
                 85                  90

<210> SEQ ID NO 85
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gly
                20                  25                  30

Ile Leu Tyr Tyr Glu Pro Val Asp Ser Gly Glu Ala Ile Thr Leu Pro
             35                  40                  45

Ile Pro Gly Ser Glu Arg Ser Tyr Asp Leu Thr Gly Leu Lys Pro Gly
         50                  55                  60

Thr Glu Tyr Trp Val Val Ile Thr Gly Val Lys Gly Gly Ala Pro Ser
 65                  70                  75                  80

Thr Pro Leu Gly Ala Ile Phe Thr Thr
                 85

<210> SEQ ID NO 86
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Leu Pro Ala Pro Lys Asn Leu Val Val Ser Arg Val Thr Glu Asp Ser
 1               5                  10                  15
```

```
Ala Arg Leu Ser Trp Thr Thr Pro Asp Ala Ala Phe Asp Ser Phe Gly
            20                  25                  30

Ile Leu Tyr Tyr Glu Pro Val Asp Ser Gly Glu Ala Ile Thr Leu Pro
            35                  40                  45

Val Pro Gly Ser Glu Arg Ser Tyr Asp Leu Thr Gly Leu Lys Pro Gly
 50                  55                  60

Thr Glu Tyr Trp Val Val Ile Thr Gly Val Lys Gly Ala Pro Ser
 65                  70                  75                  80

Thr Pro Leu Gly Ala Ile Phe Thr Thr
                85

<210> SEQ ID NO 87
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gly
            20                  25                  30

Ile Thr Tyr Tyr Glu Pro Asn His Gly Glu Ala Ile Ser Leu Ser
            35                  40                  45

Val Pro Gly Ser Glu Arg Ser Tyr Asp Pro Thr Gly Leu Lys Pro Gly
 50                  55                  60

Thr Glu Tyr Trp Val Val Ile Thr Gly Val Lys Gly Ala Pro Ser
 65                  70                  75                  80

Thr Pro Leu Gly Ala Ile Phe Thr Thr
                85

<210> SEQ ID NO 88
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Ser Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
            35                  40                  45

Ile Pro Gly Ser Glu Arg Ser Tyr Asp Leu Thr Gly Leu Lys Pro Gly
 50                  55                  60

Thr Glu Tyr Trp Val Val Ile Thr Gly Val Lys Gly Ala Pro Ser
 65                  70                  75                  80

Thr Pro Leu Gly Ala Ile Phe Thr Thr
                85

<210> SEQ ID NO 89
<211> LENGTH: 89
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 89

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Pro Gly Ser Glu Arg Ser Tyr Asp Leu Thr Gly Leu Lys Pro Gly
    50                  55                  60

Thr Glu Tyr Trp Val Val Ile Thr Gly Val Lys Gly Ala Pro Ser
65                  70                  75                  80

Thr Pro Leu Gly Thr Ile Phe Thr Thr
                85

<210> SEQ ID NO 90
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Val Gly Val Lys Gly Gly Tyr Pro Ser
65                  70                  75                  80

Ile Pro Leu Gly Ala Ala Phe Thr Thr
                85

<210> SEQ ID NO 91
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Leu Gly Ser Glu Arg Ser Tyr Asp Leu Thr Gly Leu Lys Pro Gly
    50                  55                  60

Thr Glu Tyr Trp Val Val Ile Thr Gly Val Lys Gly Gly Ala Pro Ser
65                  70                  75                  80
```

Thr Pro Leu Gly Ala Ile Phe Thr Thr
                85

<210> SEQ ID NO 92
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Leu Pro Ala Pro Lys Asn Leu Val Val Ser Arg Val Thr Glu Asp Ser
1               5                   10                  15

Ala Arg Leu Ser Trp Ile Ala Pro Asp Ala Ala Phe Asp Ser Phe Ser
            20                  25                  30

Ile Ala Tyr Val Glu Ala Glu Leu Val Gly Glu Ala Ile Gln Leu Val
        35                  40                  45

Val Pro Gly Ser Glu Arg Ser Tyr Asp Leu Thr Gly Leu Lys Pro Gly
    50                  55                  60

Thr Glu Tyr Trp Val Val Ile Leu Gly Val Lys Gly Gly Asn Pro Ser
65                  70                  75                  80

Asn Pro Leu Gly Ala Ser Phe Thr Thr
                85

<210> SEQ ID NO 93
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Trp Tyr Val Glu Gln His Pro Phe Gly Glu Ala Ile Pro Leu Phe
        35                  40                  45

Val Pro Gly Ser Glu Arg Ser Tyr Asp Leu Thr Gly Leu Lys Pro Gly
    50                  55                  60

Thr Glu Tyr Thr Val Gly Ile Arg Gly Val Lys Gly Gly Asn Phe Ser
65                  70                  75                  80

Thr Pro Leu Ile Ala His Phe Thr Thr
                85

<210> SEQ ID NO 94
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro

```
                35                  40                  45

Val Pro Gly Ser Glu Arg Ser Tyr Asp Leu Thr Gly Leu Lys Pro Gly
 50                  55                  60

Thr Glu Tyr Trp Val Val Ile Thr Gly Val Lys Gly Ala Pro Ser
65                  70                  75                  80

Thr Pro Leu Gly Ala Ile Leu Thr Thr
                85

<210> SEQ ID NO 95
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Pro Glu Trp Pro Phe Ala Gly Glu Ala Ile Gly Leu Pro
                35                  40                  45

Val Pro Gly Ser Glu Arg Ser Tyr Asp Leu Thr Gly Leu Lys Pro Gly
 50                  55                  60

Thr Glu Tyr Phe Val Val Ile Tyr Gly Val Lys Gly Gly Glu Leu Ser
65                  70                  75                  80

Glu Pro Leu Thr Ala Gln Phe Thr Thr
                85

<210> SEQ ID NO 96
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Ala Tyr Val Glu Ala Glu Leu Val Gly Glu Ala Ile Gln Leu Val
                35                  40                  45

Val Pro Gly Ser Glu Arg Ser Tyr Asp Leu Thr Gly Leu Lys Pro Gly
 50                  55                  60

Thr Glu Tyr Trp Val Val Ile Leu Gly Val Lys Gly Gly Asn Pro Ser
65                  70                  75                  80

Asn Pro Leu Gly Ala Ser Phe Thr Thr Thr
                85                  90

<210> SEQ ID NO 97
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Ala Tyr Val Glu Ala Glu Leu Val Gly Glu Ala Ile Gln Leu Val
            35                  40                  45

Val Pro Gly Ser Glu Arg Ser Tyr Asp Leu Thr Gly Leu Lys Pro Gly
    50                  55                  60

Thr Glu Tyr Trp Val Val Ile Leu Gly Val Lys Gly Asn Pro Ser
65                  70                  75                  80

Asn Pro Leu Gly Ala Ser Phe Thr Thr
                85

<210> SEQ ID NO 98
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Trp Tyr Ala Glu Tyr Gly Tyr Pro Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Asp Val Ala Ile Val Gly Val Lys Gly Gly Asn Arg Ser
65                  70                  75                  80

Tyr Pro Leu Ser Ala Ile Phe Thr Thr
                85

<210> SEQ ID NO 99
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Leu Tyr Tyr Glu Pro Val Asp Ser Gly Glu Ala Ile Thr Leu Pro
            35                  40                  45

Val Pro Gly Ser Glu Arg Ser Tyr Asp Leu Thr Gly Leu Lys Pro Gly
    50                  55                  60

Thr Glu Tyr Trp Val Val Ile Thr Gly Val Lys Gly Gly Ala Pro Ser
65                  70                  75                  80

Thr Pro Leu Gly Ala Ile Phe Thr Thr
                85

<210> SEQ ID NO 100

<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Trp Tyr His Glu Tyr Gly Gly Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ala Ile Trp Gly Val Lys Gly Asp Val Ser
65                  70                  75                  80

Tyr Pro Leu Ser Ala Ile Phe Thr Thr
                85

<210> SEQ ID NO 101
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Trp Tyr Ala Glu Tyr Gly Tyr Pro Gly Glu Ala Ile Val Leu Thr
        35                  40                  45

Val Pro Gly Ser Glu Arg Ser Tyr Asp Leu Thr Gly Leu Asn Pro Gly
    50                  55                  60

Thr Glu Tyr Asp Val Ala Ile Ser Gly Val Lys Gly Pro Arg Ser
65                  70                  75                  80

Tyr Pro Leu Ser Ala Ile Phe Thr Thr
                85

<210> SEQ ID NO 102
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Leu Gly
            20                  25                  30

Ile Thr Tyr Trp Glu Ser Pro Tyr Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gly Val Phe Ile Leu Gly Val Lys Gly Gly Tyr Pro Ser
65                  70                  75                  80

Ala Pro Leu Ser Ala Ile Phe Thr Thr
                85

<210> SEQ ID NO 103
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Trp Tyr Ala Glu Tyr Gly Tyr Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ala Ile Trp Gly Val Lys Gly Gly Val Arg Ser
65                  70                  75                  80

Tyr Pro Leu Ser Ala Ile Phe Thr Thr
                85

<210> SEQ ID NO 104
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Trp Tyr Arg Glu Tyr Gly Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ala Ile Trp Gly Val Lys Gly Gly Val Arg Ser
65                  70                  75                  80

Tyr Pro Leu Ser Ala Ile Phe Thr Thr
                85

<210> SEQ ID NO 105
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp 20                  25                  30

Ile Trp Tyr Ala Glu Tyr Gly Tyr Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Asp Val Ala Ile Ser Gly Ile Lys Gly Gly Pro Arg Ser
65                  70                  75                  80

Tyr Pro Leu Ser Ala Ile Phe Thr Thr
                85

<210> SEQ ID NO 106
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Trp Tyr Ala Glu Tyr Gly Tyr Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Asp Val Ala Ile Ser Gly Ala Lys Gly Gly Pro Arg Ser
65                  70                  75                  80

Tyr Pro Leu Ser Ala Ile Phe Thr Thr
                85

<210> SEQ ID NO 107
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Trp Tyr Arg Glu Tyr Ala Thr Gly Glu Ala Ile Val Leu Thr Val
            35                  40                  45

Pro Gly Ser Glu Arg Ser Tyr Asp Leu Thr Gly Leu Lys Pro Gly Thr
        50                  55                  60

Glu Tyr Asp Val Val Ile Thr Gly Val Lys Gly Gly Tyr Pro Ser Tyr
65                  70                  75                  80

Pro Leu Ser Ala Ile Phe Thr Thr
                85

<210> SEQ ID NO 108
<211> LENGTH: 89
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 108

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Thr Tyr Trp Glu Ser Pro Tyr Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gly Val Phe Ile Leu Gly Val Lys Gly Gly Tyr Pro Ser
65                  70                  75                  80

Ala Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Trp Tyr Ala Glu Tyr Gly Tyr Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ala Ile Tyr Gly Val Lys Gly Ser Pro Ser
65                  70                  75                  80

Tyr Pro Leu Ser Ala Ile Phe Thr Thr
                85

<210> SEQ ID NO 110
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Trp Tyr Ala Glu Tyr Gly Tyr Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ala Ile Ser Gly Val Lys Gly Gly Pro Arg Ser
65                  70                  75                  80

Tyr Pro Leu Ser Ala Ile Phe Thr Thr
                85

<210> SEQ ID NO 111
<211> LENGTH: 96
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 111

Leu Pro Ala Pro Lys Asn Leu Val Val Ser Arg Val Thr Glu Asp Ser
1               5                   10                  15

Ala Arg Leu Ser Trp Lys Arg Ile Asp Ser Pro Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                85                  90                  95

<210> SEQ ID NO 112
<211> LENGTH: 96
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 112

Leu Pro Ala Pro Lys Asn Leu Val Val Ser Arg Val Thr Glu Asp Ser
1               5                   10                  15

Ala Arg Leu Ser Trp Ile Gly His Asp Ser Gly Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                85                  90                  95

<210> SEQ ID NO 113
<211> LENGTH: 95
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 113

Leu Pro Ala Pro Lys Asn Leu Val Val Ser Arg Val Thr Glu Asp Ser
1               5                   10                  15

Ala Arg Leu Ser Trp Lys Arg Arg Trp Asp Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Asp Val Glu Trp Phe Asn
 65                  70                  75                  80

Gly Leu Pro His His Ser Asn Pro Leu Ser Ala Ile Phe Thr Thr
                85                  90                  95

<210> SEQ ID NO 114
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Leu Pro Ala Pro Lys Asn Leu Val Val Ser Arg Val Thr Glu Asp Ser
  1               5                  10                  15

Ala Arg Leu Ser Trp Ala Lys His Pro Asn Ser Phe Asp Ser Phe Leu
                 20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Asp Val Val Val Asn Glu
 65                  70                  75                  80

Leu Asn Asn Pro Leu Phe Ser Asn Pro Leu Ser Ala Ile Phe Thr Thr
                85                  90                  95

<210> SEQ ID NO 115
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Leu Pro Ala Pro Lys Asn Leu Val Val Ser Arg Val Thr Glu Asp Ser
  1               5                  10                  15

Ala Arg Leu Ser Trp Trp Thr Ser Pro Leu Pro Phe Asp Ser Phe Leu
                 20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Asp Val Lys Tyr Asp Ile
 65                  70                  75                  80

Asp Ser Arg Pro Ile Ser Ser Asn Pro Leu Ser Ala Ile Phe Thr Thr
                85                  90                  95

<210> SEQ ID NO 116
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Leu Pro Ala Pro Lys Asn Leu Val Val Ser Arg Val Thr Glu Asp Ser

```
                1               5                  10                 15
Ala Arg Leu Ser Trp Ala Lys Asn Leu His Ser Phe Asp Ser Phe Leu
                20                 25                  30

Ile Gln Tyr Gln Glu Ser Glu Lys Val Gly Glu Ala Ile Val Leu Thr
                35                 40                  45

Val Pro Gly Ser Glu Arg Ser Tyr Asp Leu Thr Gly Leu Lys Pro Gly
            50                 55                  60

Thr Glu Tyr Thr Val Ser Ile Tyr Gly Val Asp Val Lys Tyr Asp Ile
 65                 70                  75                  80

Asp Ser Arg Pro Ile Ser Ser Asn Pro Leu Ser Ala Ile Phe Thr Thr
                    85                  90                  95
```

<210> SEQ ID NO 117
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Leu Pro Ala Pro Lys Asn Leu Val Val Ser Arg Val Thr Glu Asp Ser
 1               5                  10                  15

Ala Arg Leu Ser Trp Tyr Pro Ser Asp Pro Phe Asp Ser Phe Leu
                20                 25                  30

Ile Gln Tyr Gln Glu Ser Glu Lys Val Gly Glu Ala Ile Val Leu Thr
                35                 40                  45

Val Pro Gly Ser Glu Arg Ser Tyr Asp Leu Thr Gly Leu Lys Pro Gly
            50                 55                  60

Thr Glu Tyr Thr Val Ser Ile Tyr Gly Val Pro Asn Tyr His Ser Arg
 65                 70                  75                  80

Arg Ser Tyr Tyr Tyr Ser Asn Pro Leu Ser Ala Ile Phe Thr Thr
                    85                  90                  95
```

<210> SEQ ID NO 118
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Leu Pro Ala Pro Lys Asn Leu Val Val Ser Arg Val Thr Glu Asp Ser
 1               5                  10                  15

Ala Arg Leu Ser Trp Val Lys Arg Ala Thr Ser Phe Asp Ser Phe Leu
                20                 25                  30

Ile Gln Tyr Gln Glu Ser Glu Lys Val Gly Glu Ala Ile Val Leu Thr
                35                 40                  45

Val Pro Gly Ser Glu Arg Ser Tyr Asp Leu Thr Gly Leu Lys Pro Gly
            50                 55                  60

Thr Glu Tyr Thr Val Ser Ile Tyr Gly Val Asp Val Arg Tyr Asn Glu
 65                 70                  75                  80

Gly Gln Pro Ile Trp Ser Asn Pro Leu Ser Ala Ile Phe Thr Thr
                    85                  90                  95
```

<210> SEQ ID NO 119
<211> LENGTH: 97
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 119

Leu Pro Ala Pro Lys Asn Leu Val Val Ser Arg Val Thr Glu Asp Ser
1               5                   10                  15

Ala Arg Leu Ser Trp Gln Arg Pro Lys Ser Gly Phe Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val Asp Val Lys Tyr Asp
65                  70                  75                  80

Ile Asp Ser Arg Pro Ile Ser Ser Asn Pro Leu Ser Ala Ile Phe Thr
                85                  90                  95

Thr

<210> SEQ ID NO 120
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Leu Pro Ala Pro Lys Asn Leu Val Val Ser Arg Val Thr Glu Asp Ser
1               5                   10                  15

Ala Arg Leu Ser Trp Pro Val Glu Ser Asn Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Glu Tyr Asp Gln
65                  70                  75                  80

His Gly Arg Pro Arg Trp Ser Asn Pro Leu Ser Ala Ile Phe Thr Thr
                85                  90                  95

<210> SEQ ID NO 121
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Leu Pro Ala Pro Lys Asn Leu Val Val Ser Arg Val Thr Glu Asp Ser
1               5                   10                  15

Ala Arg Leu Ser Trp Val Arg Glu His Asp Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

```
Thr Glu Tyr Thr Val Ser Ile Tyr Gly Val Asp Val Lys Tyr Asp Ile
 65                  70                  75                  80

Asp Ser Arg Pro Ile Ser Ser Asn Pro Leu Ser Ala Ile Phe Thr Thr
                 85                  90                  95

<210> SEQ ID NO 122
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Leu Pro Ala Pro Lys Asn Leu Val Val Ser Arg Val Thr Glu Asp Ser
 1               5                  10                  15

Ala Arg Leu Ser Trp Ala Lys Arg Pro Gly Ala Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Asp Val Lys Tyr Asp Ile
 65                  70                  75                  80

Asp Ser Arg Pro Ile Ser Ser Asn Pro Leu Ser Ala Ile Phe Thr Thr
                 85                  90                  95

<210> SEQ ID NO 123
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Leu Pro Ala Pro Lys Asn Leu Val Val Ser Arg Val Thr Glu Asp Ser
 1               5                  10                  15

Ala Arg Leu Ser Trp Val Lys Arg Ala Thr Ser Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Asp Val Lys Tyr Asp Ile
 65                  70                  75                  80

Asp Ser Arg Pro Ile Ser Ser Asn Pro Leu Ser Ala Ile Phe Thr Thr
                 85                  90                  95

<210> SEQ ID NO 124
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Pro Ala Pro Lys Asn Leu Val Val Ser Arg Val Thr Glu Asp Ser
 1               5                  10                  15

Ala Arg Leu Ser Trp Val Pro Ser Pro Trp Gly Phe Asp Ser Phe Leu
```

20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                    85                  90                  95

<210> SEQ ID NO 125
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Leu Pro Ala Pro Lys Asn Leu Val Val Ser Arg Val Thr Glu Asp Ser
1               5                   10                  15

Ala Arg Leu Ser Trp Ala Arg Asn Ile Thr Ser Phe Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                    85                  90                  95

<210> SEQ ID NO 126
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Leu Pro Ala Pro Lys Asn Leu Val Val Ser Arg Val Thr Glu Asp Ser
1               5                   10                  15

Ala Arg Leu Ser Trp Arg Lys Lys Asp His Pro Phe Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                    85                  90                  95

<210> SEQ ID NO 127
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Leu Pro Ala Pro Lys Asn Leu Val Val Ser Arg Val Thr Glu Asp Ser
1               5                   10                  15

Ala Arg Leu Ser Trp Gly Tyr Tyr His Gly His Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Lys Trp Glu Gly
65                  70                  75                  80

Asn Arg Pro Val Ala Ser Asn Pro Leu Ser Ala Ile Phe Thr Thr
                85                  90                  95

<210> SEQ ID NO 128
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Pro Ala Pro Lys Asn Leu Val Val Ser Arg Val Thr Glu Asp Ser
1               5                   10                  15

Ala Arg Leu Ser Trp Arg Lys Glu Ala Thr Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                85                  90                  95

<210> SEQ ID NO 129
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Pro Ala Pro Lys Asn Leu Val Val Ser Arg Val Thr Glu Asp Ser
1               5                   10                  15

Ala Arg Leu Ser Trp Val Lys Arg Ala Thr Ser Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Asp Val Lys Trp Glu Gly
65                  70                  75                  80

Asn Arg Pro Val Ala Ser Asn Pro Leu Ser Ala Ile Phe Thr Thr
                85                  90                  95

<210> SEQ ID NO 130
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Leu Pro Ala Pro Lys Asn Leu Val Val Ser Arg Val Thr Glu Asp Ser
1               5                   10                  15

Ala Arg Leu Ser Trp Pro Lys Ile Gln Gly Gln His Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Asp Val Lys Tyr Asp
65                  70                  75                  80

Ile Asp Ser Arg Pro Ile Ser Ser Asn Pro Leu Ser Ala Ile Phe Thr
                85                  90                  95

Thr

<210> SEQ ID NO 131
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Leu Pro Ala Pro Lys Asn Leu Val Val Ser Arg Val Thr Glu Asp Ser
1               5                   10                  15

Ala Arg Leu Ser Trp Gln Arg Ala Asp Asp Ile Leu Pro Tyr Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Tyr Asp Ile Asp Ser Arg Pro Ile Ser Ser Asn Pro Leu Ser Ala Ile
                85                  90                  95

Phe Thr Thr

<210> SEQ ID NO 132
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Leu Pro Ala Pro Lys Asn Leu Val Val Ser Arg Val Thr Glu Asp Ser
1               5                   10                  15

Ala Arg Leu Ser Trp Val Arg Ser Asp Thr Ala Arg Phe Phe Asp Ser
            20                  25                  30

```
Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
 50                  55                  60

Pro Gly Thr Glu Tyr Thr Val Ser Ile Tyr Gly Val Asp Val Lys Tyr
 65                  70                  75                  80

Asp Ile Asp Ser Arg Pro Ile Ser Ser Asn Pro Leu Ser Ala Ile Phe
                 85                  90                  95

Thr Thr
```

<210> SEQ ID NO 133
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Leu Pro Ala Pro Lys Asn Leu Val Val Ser Arg Val Thr Glu Asp Ser
 1               5                  10                  15

Ala Arg Leu Ser Trp Ala Ser Thr Val Asp Pro His Pro Arg Phe Asp
                20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
     50                  55                  60

Lys Pro Gly Thr Glu Tyr Thr Val Ser Ile Tyr Gly Val Asp Val Lys
 65                  70                  75                  80

Tyr Asp Ile Asp Ser Arg Pro Ile Ser Ser Asn Pro Leu Ser Ala Ile
                 85                  90                  95

Phe Thr Thr
```

<210> SEQ ID NO 134
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Leu Pro Ala Pro Lys Asn Leu Val Val Ser Arg Val Thr Glu Asp Ser
 1               5                  10                  15

Ala Arg Leu Ser Trp Gln Arg His Ser Asp Ala His Pro Leu Phe Asp
                20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
     50                  55                  60

Lys Pro Gly Thr Glu Tyr Thr Val Ser Ile Tyr Gly Val Asp Val Lys
 65                  70                  75                  80

Trp Glu Gly Asn Arg Pro Val Ala Ser Asn Pro Leu Ser Ala Ile Phe
                 85                  90                  95

Thr Thr
```

<210> SEQ ID NO 135

<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 135

Leu Pro Ala Pro Lys Asn Leu Val Val Ser Arg Val Thr Glu Asp Ser
1               5                   10                  15

Ala Arg Leu Ser Trp Pro Ile Val Asn Thr Pro Leu His Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Asp Val Gln Tyr
65                  70                  75                  80

Thr Ala Thr Gly Gln Pro Glu Arg Ser Asn Pro Leu Ser Ala Ile Phe
                85                  90                  95

Thr Thr

<210> SEQ ID NO 136
<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 136

Leu Pro Ala Pro Lys Asn Leu Val Val Ser Arg Val Thr Glu Asp Ser
1               5                   10                  15

Ala Arg Leu Ser Trp Ala Lys Thr Ser Asp Leu His Pro Leu Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 137
<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 137

Leu Pro Ala Pro Lys Asn Leu Val Val Ser Arg Val Thr Glu Asp Ser
1               5                   10                  15

Ala Arg Leu Ser Trp Asn Lys Lys His Asp Gly Gln Pro Thr Phe Asp
            20                  25                  30

Ser Phe Leu Ile Gln Tyr Gln Glu Ser Glu Lys Val Gly Glu Ala Ile
        35                  40                  45

```
Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Val
65                  70                  75                  80

Tyr Glu Gly Ser Tyr Pro Ala Ser Ser Asn Pro Leu Ser Ala Ile Phe
                85                  90                  95

Thr Thr

<210> SEQ ID NO 138
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Pro Ala Pro Lys Asn Leu Val Val Ser Arg Val Thr Glu Asp Ser
1               5                   10                  15

Ala Arg Leu Ser Trp Ile Lys Ser Glu Thr Ser Gln Pro Ala Phe Asp
                20                  25                  30

Ser Phe Leu Ile Gln Tyr Gln Glu Ser Glu Lys Val Gly Glu Ala Ile
                35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 139
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Pro Ala Pro Lys Asn Leu Val Val Ser Arg Val Thr Glu Asp Ser
1               5                   10                  15

Ala Arg Leu Ser Trp Tyr Ala Arg Lys Phe Ile Ser Pro Phe Asp Ser
                20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95

Thr

<210> SEQ ID NO 140
<211> LENGTH: 99
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 140

Leu Pro Ala Pro Lys Asn Leu Val Val Ser Arg Val Thr Glu Asp Ser
1               5                   10                  15

Ala Arg Leu Ser Trp Tyr Arg Pro Asp Asn Arg Ala Gly Ala Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Tyr Asp Ile Asp Ser Arg Pro Ile Ser Ser Asn Pro Leu Ser Ala Ile
                85                  90                  95

Phe Thr Thr

<210> SEQ ID NO 141
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Pro Ala Pro Lys Asn Leu Val Val Ser Arg Val Thr Glu Asp Ser
1               5                   10                  15

Ala Arg Leu Ser Trp Glu Arg Ile Val Gln Thr Pro His Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95

Thr

<210> SEQ ID NO 142
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Leu Pro Ala Pro Lys Asn Leu Val Val Ser Arg Val Thr Glu Asp Ser
1               5                   10                  15

Ala Arg Leu Ser Trp Pro Glu Glu Ala Val Thr Ala Thr Ser Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 143
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Leu Pro Ala Pro Lys Asn Leu Val Val Ser Arg Val Thr Glu Asp Ser
1               5                   10                  15

Ala Arg Leu Ser Trp Pro Lys Asn Gln Thr Asn Arg His Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95

Thr

<210> SEQ ID NO 144
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Leu Pro Ala Pro Lys Asn Leu Val Val Ser Arg Val Thr Glu Asp Ser
1               5                   10                  15

Ala Arg Leu Ser Trp Tyr Arg Ala Thr Thr Pro Ala Pro His Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Asp Val Lys
65                  70                  75                  80

Trp Glu Gly Asn Arg Pro Val Ala Ser Asn Pro Leu Ser Ala Ile Phe
                85                  90                  95

Thr Thr

<210> SEQ ID NO 145
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Leu Pro Ala Pro Lys Asn Leu Val Val Ser Arg Val Thr Glu Asp Ser
1               5                   10                  15

Ala Arg Leu Ser Trp Ser Ala Lys Lys Phe Pro Arg His Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Asp Val Lys Trp
65                  70                  75                  80

Glu Gly Asn Arg Pro Val Ala Ser Asn Pro Leu Ser Ala Ile Phe Thr
                85                  90                  95

Thr

<210> SEQ ID NO 146
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ala Tyr Pro Glu Trp Pro Val Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Asp Trp Ser
65                  70                  75                  80

Glu Pro Leu Ser Ala Ile Phe Thr Thr
                85

<210> SEQ ID NO 147
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Pro Glu Trp Pro Val Arg Gly Asp Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Gln Gly Val Lys Gly Thr Asp Ser
65                  70                  75                  80

Phe Pro Leu Ser Ala Ile Phe Thr Thr

<210> SEQ ID NO 148
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Thr Tyr Pro Glu Ile Pro Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Leu Leu Ser
65                  70                  75                  80

Ser Pro Leu Ser Ala Ile Phe Thr Thr
                85

<210> SEQ ID NO 149
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ser Tyr Pro Glu Trp Glu Gln Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Ala Leu Ser
65                  70                  75                  80

Ala Pro Leu Ser Ala Ile Phe Thr Thr
                85

<210> SEQ ID NO 150
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ser Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
            50                  55                  60

Thr Glu Tyr Trp Val Ile Ile Leu Gly Val Lys Gly Gly Asp Gln Ser
 65                  70                  75                  80

Trp Pro Leu Ser Ala Ile Phe Thr Thr
                 85

<210> SEQ ID NO 151
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gln
            20                  25                  30

Ile Ala Tyr Pro Glu Trp Pro Lys Asp Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Ala Val Phe Ile Trp Gly Val Lys Gly Gly Val Tyr Ser
 65                  70                  75                  80

Asn Pro Leu Ser Ala Ile Phe Thr Thr
                 85

<210> SEQ ID NO 152
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
            20                  25                  30

Ile Ala Tyr Pro Glu Trp Pro Lys Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Phe Val Val Ile Tyr Gly Val Lys Gly Gly Ile His Ser
 65                  70                  75                  80

Ala Pro Leu Ser Ala Ile Phe Thr Thr
                 85

<210> SEQ ID NO 153
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Thr Pro Ile Gln Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Phe Val Ile His Gly Val Lys Gly Gly Ile Thr Ser
65                  70                  75                  80

Phe Pro Leu Ser Ala Ile Phe Thr Thr
                85

<210> SEQ ID NO 154
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ser Tyr Pro Glu Trp Pro Leu Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Trp Val Ile Ile Phe Gly Val Lys Gly Gly Glu Arg Ser
65                  70                  75                  80

Trp Pro Leu Ser Ala Ile Phe Thr Thr
                85

<210> SEQ ID NO 155
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Pro Glu Leu Pro Ile Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Phe Val Ile Ile Arg Gly Val Lys Gly Gly Thr Leu Ser
65                  70                  75                  80

Pro Pro Leu Ser Ala Ile Phe Thr Thr
                85

<210> SEQ ID NO 156
<211> LENGTH: 89
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ser Tyr Pro Glu Trp Pro Val Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Gln Gly Val Lys Gly Gly Lys Leu Ser
65                  70                  75                  80

Trp Pro Leu Ser Ala Ile Phe Thr Thr
                85

<210> SEQ ID NO 157
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Ala Tyr Pro Glu Trp Pro Val Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Tyr Gly Val Lys Gly Gly Asp Arg Ser
65                  70                  75                  80

Asn Pro Leu Ser Ala Ile Phe Thr Thr
                85

<210> SEQ ID NO 158
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Ala Tyr Pro Glu Trp Pro Val His Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Gly Val Leu Ser
```

65                  70                  75                  80

Glu Pro Leu Ser Ala Ile Phe Thr Thr
                85

<210> SEQ ID NO 159
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Thr Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Asn Gly Val Lys Gly Gly Trp Arg Ser
65                  70                  75                  80

Phe Pro Leu Ser Ala Ile Phe Thr Thr
                85

<210> SEQ ID NO 160
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ala Tyr Pro Glu Trp Pro Val Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Phe Gly Ser
65                  70                  75                  80

Phe Pro Leu Ser Ala Ile Phe Thr Thr
                85

<210> SEQ ID NO 161
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Ala Tyr Pro Glu Arg Glu Gln Asp Lys Trp Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Trp Val Ile Ile Gln Gly Val Lys Gly Gly Arg
65                  70                  75                  80

Pro Ser Thr Pro Leu Ser Ala Ile Leu Thr Thr
                85                  90

<210> SEQ ID NO 162
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Trp Pro Pro Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Phe Val Ile Ile Tyr Gly Val Lys Gly Gly Trp Thr Ser Pro
65                  70                  75                  80

Pro Leu Ser Ala Ile Phe Thr Thr
                85

<210> SEQ ID NO 163
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Ala Tyr Pro Glu Trp Pro Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Phe Gly Val Lys Gly Ser Gln Ser
65                  70                  75                  80

Trp Pro Leu Ser Ala Ile Phe Thr Thr
                85

<210> SEQ ID NO 164
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Trp Tyr Pro Glu Trp Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Asn Ile Ser Gly Val Lys Gly Glu Tyr Ser
65                  70                  75                  80

Phe Pro Leu Ser Ala Ile Phe Thr Thr
                85

<210> SEQ ID NO 165
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
                20                  25                  30

Ile Ser Tyr Pro Glu Trp Pro Val His Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Ile Ile Trp Gly Val Lys Gly Arg Gln Ser
65                  70                  75                  80

Trp Pro Leu Ser Ala Ile Phe Thr Thr
                85

<210> SEQ ID NO 166
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Ala Tyr Pro Glu Leu Pro Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Ile Ile Trp Gly Val Lys Gly Gly Asp Arg Ser
65                  70                  75                  80

Glu Pro Leu Ser Ala Ile Phe Thr Thr
                85

```
<210> SEQ ID NO 167
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Ala Tyr Pro Glu Thr Pro Val Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Ile Gly Val Lys Gly Gly Gln Glu Ser
65                  70                  75                  80

Phe Pro Leu Ser Ala Ile Phe Thr Thr
                85

<210> SEQ ID NO 168
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Ser Tyr Ile Glu Tyr Pro Glu Ile Pro Gly Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Trp Val Pro Ile Trp Gly Val Lys Gly Gly Ile
65                  70                  75                  80

Gln Ser Trp Pro Leu Ser Ala Ile Phe Thr Thr
                85                  90

<210> SEQ ID NO 169
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Val Glu Trp Trp His Arg Gly Glu Ala Ile Ser Leu Pro
        35                  40                  45

Val Pro Gly Ser Glu Arg Ser Tyr Asp Leu Thr Gly Leu Lys Pro Gly
```

```
            50                  55                  60

Thr Glu Tyr Asn Val Ile Ile Thr Gly Val Lys Gly Ile Pro Ser
65                  70                  75                  80

His Pro Leu Gly Ala Ile Phe Thr Thr
                85

<210> SEQ ID NO 170
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Pro Tyr Trp Glu Ser Glu Val Tyr Gly Glu Ala Ile Ala Leu Pro
                35                  40                  45

Val Pro Gly Ser Glu Arg Ser Tyr Asp Leu Thr Gly Leu Lys Pro Gly
            50                  55                  60

Thr Glu Tyr Gln Val Ser Ile Ile Gly Val Lys Gly Val Tyr Ser
65                  70                  75                  80

Gln Pro Leu Ala Ala Ile Phe Thr Thr
                85

<210> SEQ ID NO 171
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Gly Tyr Ala Glu Pro Val Thr Gly Glu Ala Ile Ser Leu Ser
                35                  40                  45

Val Pro Gly Ser Glu Arg Ser Tyr Asp Leu Thr Gly Leu Lys Pro Gly
            50                  55                  60

Thr Glu Tyr Trp Val Ile Ile Gly Val Lys Gly Gly Ile Asn Ser
65                  70                  75                  80

Tyr Pro Leu Gly Ala Ile Phe Thr Thr
                85

<210> SEQ ID NO 172
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Leu Pro Ala Pro Lys Asn Leu Val Val Ser Arg Val Thr Glu Asp Ser
1               5                   10                  15
```

Ala Arg Leu Ser Trp Thr Ala Pro Asp Ala Ala Phe Asp Ser Phe Tyr
            20                  25                  30

Ile Pro Tyr Trp Glu Ser Glu Val Tyr Gly Glu Ala Ile Ala Leu Pro
        35                  40                  45

Val Thr Gly Ser Glu Arg Ser Tyr Asp Leu Thr Gly Leu Lys Pro Gly
    50                  55                  60

Thr Glu Tyr Gln Val Ser Ile Ile Gly Val Lys Gly Val Tyr Ser
65                  70                  75                  80

Gln Pro Leu Ala Ala Ile Phe Thr Thr
                85

<210> SEQ ID NO 173
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Pro Tyr Arg Glu Ser Glu Phe Arg Gly Glu Ala Ile Ala Leu Pro
        35                  40                  45

Val Pro Gly Ser Glu Arg Ser Tyr Asp Leu Thr Gly Leu Lys Pro Gly
    50                  55                  60

Thr Lys Tyr Arg Val Ile Ile Ile Gly Val Lys Gly Gly Glu Phe Ser
65                  70                  75                  80

Gln Pro Leu Ala Ala Ile Phe Thr Thr
                85

<210> SEQ ID NO 174
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Pro Tyr Arg Glu Ser Glu Phe Arg Gly Glu Ala Ile Ala Leu Pro
        35                  40                  45

Val Pro Gly Ser Glu Arg Ser Tyr Asp Leu Thr Gly Leu Lys Pro Gly
    50                  55                  60

Thr Lys Tyr Ser Val Ile Ile Ile Gly Val Lys Gly Gly Glu Phe Ser
65                  70                  75                  80

Gln Pro Leu Gly Ala Ile Phe Thr Thr
                85

<210> SEQ ID NO 175
<211> LENGTH: 89
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 175

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Pro Tyr Arg Glu Ser Glu Phe Arg Gly Glu Ala Ile Ala Leu Ser
            35                  40                  45

Val Pro Gly Ser Glu Arg Ser Tyr Asp Leu Thr Gly Leu Lys Pro Gly
        50                  55                  60

Thr Lys Tyr Arg Val Ile Ile Ile Gly Val Lys Gly Gly Glu Phe Ser
65                  70                  75                  80

Gln Pro Leu Gly Ala Ile Phe Thr Thr
                85

<210> SEQ ID NO 176
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Ser Tyr Tyr Glu Trp Ala Pro Asn Gly Glu Ala Ile Gln Leu Ser
            35                  40                  45

Val Pro Gly Ser Glu Arg Ser Tyr Asp Leu Thr Gly Leu Lys Pro Gly
        50                  55                  60

Thr Glu Tyr His Val Val Ile Ile Gly Val Lys Gly Gly Glu Pro Ser
65                  70                  75                  80

His Pro Leu Gly Ala Ile Phe Thr Thr
                85

<210> SEQ ID NO 177
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Pro Tyr Arg Glu Ser Glu Phe Arg Gly Glu Ala Ile Ala Leu Pro
            35                  40                  45

Val Pro Gly Ser Glu Arg Ser Tyr Asp Leu Thr Gly Leu Lys Pro Gly
        50                  55                  60

Thr Lys Tyr Arg Val Ile Ile Ile Gly Val Lys Gly Gly Glu Phe Ser
65                  70                  75                  80
```

```
Gln Pro Leu Ser Ala Ile Phe Thr Thr
                85
```

<210> SEQ ID NO 178
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Thr Tyr Pro Glu Trp Pro Val Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ala Val Phe Ile Trp Gly Val Lys Gly Asp Ala Ser
65                  70                  75                  80

Glu Pro Leu Ser Ala Ile Phe Thr Thr
                85
```

<210> SEQ ID NO 179
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Ala Tyr Pro Glu Trp Pro Thr Arg Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Val Ile Tyr Gly Val Lys Gly Gly Ser Pro Ser
65                  70                  75                  80

Pro Pro Leu Ser Ala Ile Phe Thr Thr
                85
```

<210> SEQ ID NO 180
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
                20                  25                  30

Ile Ala Tyr Gly Glu Tyr Pro Gly Pro Gly Glu Ala Ile Val Leu Thr
```

```
                35                  40                  45
Val Pro Gly Ser Glu Arg Ser Tyr Asp Leu Thr Gly Leu Lys Pro Gly
     50                  55                  60
Thr Glu Tyr Trp Val Pro Ile Trp Gly Val Lys Gly Glu Leu Ser
 65                  70                  75                  80
Glu Pro Leu Ser Ala Ile Phe Thr Thr
                 85

<210> SEQ ID NO 181
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Leu Pro Ala Pro Lys Asn Leu Val Val Ser Arg Val Thr Glu Asp Ser
 1               5                  10                  15
Ala Arg Leu Ser Trp Thr Ala Pro Asp Ala Ala Phe Asp Ser Phe Trp
                20                  25                  30
Ile Thr Tyr Pro Glu Trp Pro Val Asn Gly Glu Ala Ile Val Leu Thr
                35                  40                  45
Val Pro Gly Ser Glu Arg Ser Tyr Asp Leu Thr Gly Leu Lys Pro Gly
     50                  55                  60
Thr Glu Tyr Trp Val Val Ile Trp Gly Val Lys Gly Val Glu Ser
 65                  70                  75                  80
Pro Pro Leu Ser Ala Ile Phe Thr Thr
                 85

<210> SEQ ID NO 182
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Leu Pro Ala Pro Lys Asn Leu Val Val Ser Arg Val Thr Glu Asp Ser
 1               5                  10                  15
Ala Arg Leu Ser Trp Thr Ala Pro Asp Ala Ala Phe Asp Ser Phe Lys
                20                  25                  30
Ile Ser Tyr Pro Glu Trp Pro Pro Gly Glu Ala Ile Val Leu Thr
                35                  40                  45
Val Pro Gly Ser Glu Arg Ser Tyr Asp Leu Thr Gly Leu Lys Pro Gly
     50                  55                  60
Thr Glu Tyr Ala Val Phe Ile Trp Cys Val Lys Gly Glu His Ser
 65                  70                  75                  80
Trp Pro Leu Ser Ala Ile Phe Thr Thr
                 85

<210> SEQ ID NO 183
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
                20                  25                  30

Ile Ala Tyr Pro Glu Trp Pro Asp Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Ile Ile Tyr Gly Val Lys Gly Ile Leu Ser
65                  70                  75                  80

Pro Pro Leu Ser Ala Ile Phe Thr Thr
                85

<210> SEQ ID NO 184
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
                20                  25                  30

Ile Ala Tyr Pro Glu Trp Pro Val Arg Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Ile Ile Ile Gly Val Lys Gly Gly Glu Asp Ser
65                  70                  75                  80

Trp Pro Leu Ser Ala Ile Phe Thr Thr
                85

<210> SEQ ID NO 185
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Ala Tyr Pro Glu Trp Pro Val Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Val Ile Tyr Gly Val Lys Gly Gly Asn Tyr Ser
65                  70                  75                  80

Asp Pro Leu Ser Ala Ile Phe Thr Thr
                85

<210> SEQ ID NO 186

```
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Leu Gly Val Lys Gly Asp Gln Ser
65                  70                  75                  80

Trp Pro Leu Ser Ala Ile Phe Thr Thr
                85

<210> SEQ ID NO 187
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Phe Tyr Pro Glu Leu Val Phe Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Asn Ile Ser Gly Val Lys Gly Gly Glu His Ser
65                  70                  75                  80

Trp Pro Leu Ser Ala Ile Phe Thr Thr
                85

<210> SEQ ID NO 188
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Ala Tyr Pro Glu Leu Pro Val Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60
```

Thr Glu Tyr Phe Val Val Ile Trp Gly Val Lys Gly Gly Thr Tyr Ser
65                  70                  75                  80

Gly Pro Leu Ser Ala Ile Phe Thr Thr
                85

<210> SEQ ID NO 189
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Ala Tyr Pro Glu Ile Pro Ile Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Gly Asp Trp Ser
65                  70                  75                  80

Asp Pro Leu Ser Ala Ile Phe Thr Thr
                85

<210> SEQ ID NO 190
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Val Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Lys Gly Val Lys Gly Gly Asn Ile Ser
65                  70                  75                  80

Trp Pro Leu Ser Ala Ile Phe Thr Thr
                85

<210> SEQ ID NO 191
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp 20                  25                  30

Ile Gly Tyr Pro Glu Trp Pro Ile Lys Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Trp Val Ile Ile Trp Gly Val Lys Gly Gly Asp Arg Ser
65                  70                  75                  80

Glu Pro Leu Ser Ala Ile Phe Thr Thr
                85

<210> SEQ ID NO 192
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Ala Tyr Pro Glu Ile Ala Lys Trp Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Phe Val Ile Ile Tyr Gly Val Lys Gly Gly Val His Ser
65                  70                  75                  80

Phe Pro Leu Ser Ala Ile Phe Thr Thr
                85

<210> SEQ ID NO 193
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
                20                  25                  30

Ile Phe Tyr Pro Glu Leu Pro Ile Ala Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Trp Val Asn Ile Ser Gly Val Lys Gly Gly Tyr Glu Ser
65                  70                  75                  80

Trp Pro Leu Ser Ala Ile Phe Thr Thr
                85

<210> SEQ ID NO 194
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ser Tyr Pro Glu Leu Pro Val Glu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Trp Gly Val Lys Gly Gly Ala Thr Ser
65                  70                  75                  80

Glu Pro Leu Ser Ala Ile Phe Thr Thr
                85

<210> SEQ ID NO 195
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Tyr Pro Ala Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Ile Gly Val Lys Gly Gly Asp Glu Ser
65                  70                  75                  80

Phe Pro Leu Ser Ala Ile Phe Thr Thr
                85

<210> SEQ ID NO 196
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Leu Pro Ile Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Ile His Ser
65                  70                  75                  80

Ala Pro Leu Ser Ala Ile Phe Thr Thr
                85

<210> SEQ ID NO 197
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Ala Tyr Pro Glu Trp Pro Pro Glu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly His Leu Ser
65                  70                  75                  80

Asp Pro Leu Ser Ala Ile Phe Thr Thr
                85

<210> SEQ ID NO 198
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Gln Tyr Leu Glu Thr Ala Pro Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Trp Ile Pro Gly Val Lys Gly Gly Ala Phe Ser
65                  70                  75                  80

Pro Leu Ser Ala Ile Phe Thr Thr
                85

<210> SEQ ID NO 199
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Trp Pro Ile Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Val Ile Tyr Gly Val Lys Gly Val Phe Ser
65                  70                  75                  80

Glu Pro Leu Ser Ala Ile Phe Thr Thr
                85

<210> SEQ ID NO 200
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Tyr Ile Glu Asn Lys Val Asn Gly Glu Ala Ile Val Leu Thr Val Pro
        35                  40                  45

Gly Ser Glu Arg Ser Tyr Asp Leu Thr Gly Leu Lys Pro Gly Thr Glu
    50                  55                  60

Tyr His Val Thr Ile Gly Gly Val Lys Gly Thr Glu Ser Asn Thr
65                  70                  75                  80

Leu Ser Ala Ile Phe Thr Thr
                85

<210> SEQ ID NO 201
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Val Thr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Phe Gly Val Lys Gly Gly Glu Arg Ser
65                  70                  75                  80

Trp Pro Leu Ser Ala Ile Phe Thr Thr
                85

<210> SEQ ID NO 202
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Leu Pro Ala Pro Lys Asn Leu Val Val Ser Arg Val Thr Glu Asp Ser

```
                1               5                   10                  15
Ala Arg Leu Ser Trp Thr Ala Pro Asp Ala Ala Phe Asp Ser Phe Gln
            20                  25                  30

Ile Ala Tyr Pro Glu Tyr Pro Ala Leu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Ile Ile Ala Gly Val Lys Gly Ile Gln Ser
65                  70                  75                  80

Trp Pro Leu Ser Ala Ile Phe Thr Thr
                85
```

<210> SEQ ID NO 203
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ser Tyr Pro Glu Trp Pro Gly Ser Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ala Val Phe Ile Trp Cys Val Lys Gly Trp Leu Ser
65                  70                  75                  80

Asp Pro Leu Ser Ala Ile Phe Thr Thr
                85
```

<210> SEQ ID NO 204
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Ala Tyr Pro Glu Trp Pro Val Asn Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Val Ile Trp Gly Val Lys Gly Gly Val Asn Ser
65                  70                  75                  80

Tyr Pro Leu Ser Ala Ile Phe Thr Thr
                85
```

<210> SEQ ID NO 205
<211> LENGTH: 89
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 205

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Thr Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Tyr Gly Val Lys Gly Gly Ser Tyr Ser
65                  70                  75                  80

Glu Pro Leu Ser Ala Ile Phe Thr Thr
                85

<210> SEQ ID NO 206
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Leu Tyr Tyr Glu Leu Pro Pro Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Phe Gly Val Lys Gly Gly Asp Asn Ser
65                  70                  75                  80

Phe Pro Leu Ser Ala Ile Phe Thr Thr
                85

<210> SEQ ID NO 207
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Ala Tyr Pro Glu Trp Pro Thr Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly His Trp Ser
65                  70                  75                  80
```

Tyr Pro Leu Ser Ala Ile Phe Thr Thr
                85

<210> SEQ ID NO 208
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Trp Tyr His Glu Tyr His Pro Arg Gly Glu Ala Ile Val Leu Thr
        35                  40                  45

Val Pro Ser Ser Glu Arg Ser Tyr Asp Leu Thr Gly Leu Lys Pro Gly
    50                  55                  60

Thr Glu Tyr Asp Val Val Ile Ser Gly Val Lys Gly Gly His Trp Ser
65                  70                  75                  80

Tyr Pro Leu Ser Ala Ile Phe Thr Thr
                85

<210> SEQ ID NO 209
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gly Tyr Pro Glu Trp Pro Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Ile Ile Tyr Gly Val Lys Gly Gly Glu Tyr Ser
65                  70                  75                  80

Asp Pro Leu Ser Ala Ile Phe Thr Thr
                85

<210> SEQ ID NO 210
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Trp Tyr His Glu Tyr His Pro Arg Gly Glu Ala Ile Val Leu Thr
    35                  40                  45

Val Pro Gly Ser Glu Arg Ser Tyr Asp Leu Thr Gly Leu Lys Pro Gly
 50                  55                  60

Thr Glu Tyr Asp Val Val Ile Ser Gly Val Lys Gly Gly His Trp Ser
 65                  70                  75                  80

Tyr Pro Leu Ser Ala Ile Phe Thr Thr
                85

<210> SEQ ID NO 211
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                20                  25                  30

Ile Ala Tyr Pro Glu Trp Pro Thr Asp Gly Glu Ala Ile Val Leu Thr
    35                  40                  45

Val Pro Gly Ser Glu Arg Ser Tyr Asp Leu Thr Gly Leu Lys Pro Gly
 50                  55                  60

Thr Glu Tyr Phe Val Ile Ile Tyr Gly Val Lys Gly Gly Ala Leu Ser
 65                  70                  75                  80

Arg Pro Leu Ser Ala Ile Phe Thr Thr
                85

<210> SEQ ID NO 212
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Tyr
                20                  25                  30

Ile Ala Tyr Pro Glu Tyr Val Trp Gly Glu Ala Thr Ser Leu Gly
    35                  40                  45

Glu Ala Ile Val Leu Thr Val Pro Gly Ser Glu Arg Ser Tyr Asp Leu
 50                  55                  60

Thr Gly Leu Lys Pro Gly Thr Glu Tyr Phe Val Ile Thr Gly Val
 65                  70                  75                  80

Lys Gly Gly Leu Gly Ser Tyr Pro Leu Ser Ala Ile Phe Thr Thr
                85                  90                  95

<210> SEQ ID NO 213
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Ala Tyr Pro Glu Trp Pro Thr Asp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Val Ile Tyr Gly Val Lys Gly Gly Gly Arg Ser
65                  70                  75                  80

Tyr Pro Leu Ser Ala Ile Phe Thr Thr
                85

<210> SEQ ID NO 214
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Asn Tyr Trp Glu Glu Asp Pro Ala Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Arg Val Leu Ile Gly Gly Val Lys Gly Gly His Gly Ser
65                  70                  75                  80

Leu Pro Leu Ser Ala Ile Phe Thr Thr
                85

<210> SEQ ID NO 215
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Ala Tyr Pro Glu Trp Pro Thr Asp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Val Ile Tyr Gly Val Lys Gly Gly Gly Arg Ser
65                  70                  75                  80

Ala Pro Leu Ser Ala Ile Phe Thr Thr
                85

<210> SEQ ID NO 216
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Phe Tyr Leu Glu Pro Phe Pro Arg Gly Glu Ala Ile Pro Leu Glu
        35                  40                  45

Val Pro Gly Ser Glu Arg Ser Tyr Asp Leu Thr Gly Leu Lys Pro Gly
    50                  55                  60

Thr Glu Tyr Ser Val Asp Ile Arg Gly Val Lys Gly Gly Asp His Ser
65                  70                  75                  80

Asp Pro Leu Trp Ala Tyr Phe Thr Thr
                85

<210> SEQ ID NO 217
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Gly Tyr Val Glu Phe Thr Arg Ala Gly Glu Ala Ile Ser Leu Ser
        35                  40                  45

Val Pro Gly Ser Glu Arg Ser Tyr Asp Leu Thr Gly Leu Lys Pro Gly
    50                  55                  60

Thr Glu Tyr His Val Val Ile Ile Gly Val Lys Gly Gly Glu Pro Ser
65                  70                  75                  80

His Pro Leu Gly Ala Pro Phe Thr Thr
                85

<210> SEQ ID NO 218
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Gly Tyr Ala Glu Pro Ala Val Thr Gly Glu Ala Ile Ser Leu Ser
        35                  40                  45

Val Pro Gly Ser Lys Arg Ser Tyr Asp Leu Thr Gly Leu Lys Pro Gly
    50                  55                  60

Thr Glu Tyr Trp Val Val Ile Ile Gly Val Lys Gly Ile Asn Ser
65                  70                  75                  80

Tyr Pro Leu Gly Ala Ser Phe Thr Thr
                85

<210> SEQ ID NO 219
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Ser Tyr Tyr Glu Trp Ala Pro Asn Gly Glu Ala Ile Gln Leu Ser
            35                  40                  45

Val Pro Gly Ser Glu Arg Ser Tyr Asp Leu Thr Gly Leu Lys Pro Gly
        50                  55                  60

Thr Glu Tyr His Val Val Ile Ile Gly Val Lys Gly Glu Pro Ser
65                  70                  75                  80

His Pro Leu Gly Ala Pro Phe Thr Thr
                85

<210> SEQ ID NO 220
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asn Ser Phe Gly
                20                  25                  30

Ile Gly Tyr Ala Glu Pro Ala Val Thr Gly Glu Ala Ile Ser Leu Ser
            35                  40                  45

Val Pro Gly Ser Glu Arg Ser Tyr Asp Leu Thr Gly Leu Lys Pro Gly
        50                  55                  60

Thr Glu Tyr Trp Val Val Ile Ile Gly Val Lys Gly Ile Asn Ser
65                  70                  75                  80

Tyr Pro Leu Gly Ala Ser Phe Thr Thr
                85

<210> SEQ ID NO 221
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Leu Pro Ala Pro Lys Asn Leu Val Val Ser Arg Val Thr Glu Asp Ser
1               5                   10                  15

```
Ala Arg Leu Ser Trp Thr Ala Pro Asp Ala Ala Phe Asp Ser Phe Ala
            20                  25                  30

Ile Trp Cys Val Glu Pro Ile Pro Glu Gly Glu Ala Ile Pro Leu Phe
        35                  40                  45

Val Pro Gly Ser Glu Arg Ser Tyr Asp Leu Thr Gly Leu Lys Pro Gly
    50                  55                  60

Thr Glu Tyr Arg Val Gly Ile Arg Gly Val Lys Gly Thr Phe Ser
65                  70                  75                  80

Ser Pro Leu Ala Ala Pro Phe Thr Thr
                85

<210> SEQ ID NO 222
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Pro Tyr Arg Glu Ser Glu Phe Arg Gly Glu Ala Ile Ala Leu Pro
        35                  40                  45

Val Pro Gly Ser Glu Arg Ser Tyr Asp Leu Thr Gly Leu Lys Pro Gly
    50                  55                  60

Thr Lys Tyr Arg Val Ile Ile Gly Val Lys Gly Gly Glu Phe Ser
65                  70                  75                  80

Gln Pro Leu Gly Ala Ile Phe Thr Thr
                85

<210> SEQ ID NO 223
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Gly Tyr Ile Glu Trp Val His Arg Gly Glu Ala Ile Ser Leu His
        35                  40                  45

Val Pro Gly Ser Glu Arg Ser Tyr Asp Leu Thr Gly Leu Lys Pro Gly
    50                  55                  60

Thr Glu Tyr Val Val Ala Ile Val Gly Val Lys Gly Gly Glu Pro Ser
65                  70                  75                  80

Thr Pro Leu Gly Ala Pro Phe Thr Thr
                85

<210> SEQ ID NO 224
<211> LENGTH: 89
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 224

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Thr Tyr Trp Glu Ile Glu Pro Glu Gly Glu Ala Ile Phe Leu Gly
        35                  40                  45

Val Pro Gly Ser Glu Arg Ser Tyr Asp Leu Thr Gly Leu Lys Pro Gly
    50                  55                  60

Thr Glu Tyr Arg Val Gln Ile Asn Gly Val Lys Gly Thr Ile Ser
65                  70                  75                  80

Tyr Pro Leu Phe Ala Gly Phe Thr Thr
                85

<210> SEQ ID NO 225
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Val Glu Trp Trp His Arg Gly Glu Ala Ile Ser Leu Pro
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Leu Gly Val Lys Gly Ile Ile Ser
65                  70                  75                  80

Thr Pro Leu Gly Ala Ser Phe Thr Thr
                85

<210> SEQ ID NO 226
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Gly Tyr Ala Glu Pro Ala Val Thr Gly Glu Ala Ile Ser Leu Ser
        35                  40                  45

Val Pro Gly Ser Glu Arg Ser Tyr Asp Leu Thr Gly Leu Lys Pro Gly
    50                  55                  60

Thr Glu Tyr Trp Val Val Ile Ile Gly Val Lys Gly Ile Asn Ser
65                  70                  75                  80

Tyr Pro Leu Gly Ala Ser Phe Thr Thr

<210> SEQ ID NO 227
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Ile Glu Thr Ala Arg Trp Gly Glu Ala Ile Ser Leu Thr
        35                  40                  45

Val Pro Gly Ser Glu Arg Ser Tyr Asp Leu Thr Gly Leu Lys Pro Gly
    50                  55                  60

Thr Glu Tyr Asn Val Val Ile Ile Gly Val Lys Gly Thr Pro Ser
65                  70                  75                  80

His Pro Leu Gly Ala Pro Phe Thr Thr
                85

<210> SEQ ID NO 228
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Thr Tyr Leu Asp Pro Arg Asn Gly Glu Ala Ile Ser Leu Asn Val
        35                  40                  45

Pro Gly Ser Glu Arg Ser Tyr Asp Leu Thr Gly Leu Lys Pro Gly Thr
    50                  55                  60

Glu Tyr Trp Val Val Ile Gly Val Lys Gly Gly Ile Asn Ser Tyr
65                  70                  75                  80

Pro Leu Gly Ala Ser Phe Thr Thr
                85

<210> SEQ ID NO 229
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Trp Pro Pro Gly Glu Ala Ile Val Leu Thr
        35                  40                  45

```
Val Pro Gly Ser Cys Arg Ser Tyr Asp Leu Thr Gly Leu Lys Pro Gly
         50                  55                  60

Thr Glu Tyr Phe Val Ile Ile Gln Gly Val Lys Gly Gly Val Glu Ser
 65                  70                  75                  80

Trp Pro Leu Ser Ala Ile Phe Thr Thr
                 85

<210> SEQ ID NO 230
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                 20                  25                  30

Ile Ala Tyr Pro Glu Trp Pro Pro Gln Gly Glu Ala Ile Val Leu Thr
                 35                  40                  45

Val Pro Gly Ser Cys Arg Ser Tyr Asp Leu Thr Gly Leu Lys Pro Gly
         50                  55                  60

Thr Glu Tyr Phe Val Val Ile Tyr Gly Val Lys Gly Gly Ser Tyr Ser
 65                  70                  75                  80

Ala Pro Leu Ser Ala Ile Phe Thr Thr
                 85

<210> SEQ ID NO 231
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                 20                  25                  30

Ile Thr Tyr Ile Glu Lys Glu His Ile Glu Asp Gly Glu Ala Ile Val
                 35                  40                  45

Leu Thr Val Pro Gly Ser Cys Arg Ser Tyr Asp Leu Thr Gly Leu Lys
         50                  55                  60

Pro Gly Thr Glu Tyr Trp Val Pro Ile Trp Gly Val Lys Gly Gly Ala
 65                  70                  75                  80

Asn Ser Trp Pro Leu Ser Ala Ile Phe Thr Thr
                 85                  90

<210> SEQ ID NO 232
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
            35                  40                  45

Val Pro Gly Ser Cys Arg Ser Tyr Asp Leu Thr Gly Leu Lys Pro Gly
    50                  55                  60

Thr Glu Tyr Trp Val Val Ile Thr Gly Val Lys Gly Gly Ala Pro Ser
65                  70                  75                  80

Thr Pro Leu Gly Thr Ile Phe Thr Thr
                85

<210> SEQ ID NO 233
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Leu Pro Ala Pro Lys Asn Leu Val Val Ser Arg Val Thr Glu Asp Ser
1               5                   10                  15

Ala Arg Leu Ser Trp Ala Lys Arg Pro Gly Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr Thr Val Ser Ile Tyr Gly Val Asp Val Lys Tyr Asp Ile
65                  70                  75                  80

Asp Ser Arg Pro Ile Ser Ser Asn Pro Leu Ser Ala Ile Phe Thr Thr
                85                  90                  95

<210> SEQ ID NO 234
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Thr Tyr Pro Glu Trp Pro Asp Pro Gly Gly Glu Ala Ile Val Leu
            35                  40                  45

Thr Val Pro Gly Ser Cys Arg Ser Tyr Asp Leu Thr Gly Leu Lys Pro
    50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 235
<211> LENGTH: 89
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Tyr Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Val Glu Ser
65                  70                  75                  80

Trp Pro Leu Ser Ala Ile Phe Thr Thr
                85

<210> SEQ ID NO 236
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Leu Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Val Glu Ser
65                  70                  75                  80

Trp Pro Leu Ser Ala Ile Phe Thr Thr
                85

<210> SEQ ID NO 237
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Ile Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Val Glu Ser
```

```
                65                  70                  75                  80
Trp Pro Leu Ser Ala Ile Phe Thr Thr
                    85

<210> SEQ ID NO 238
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Val Glu Ser
65                  70                  75                  80

Tyr Pro Leu Ser Ala Ile Phe Thr Thr
                    85

<210> SEQ ID NO 239
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Ala Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Ile Ile Gln Gly Val Lys Gly Gly Val Glu Ser
65                  70                  75                  80

Leu Pro Leu Ser Ala Ile Phe Thr Thr
                    85

<210> SEQ ID NO 240
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30
```

```
Ile Ala Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Phe Val Ile Ile Gln Gly Val Lys Gly Gly Val Glu Ser
 65                  70                  75                  80

Ser Pro Leu Ser Ala Ile Phe Thr Thr
                85
```

<210> SEQ ID NO 241
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gln
            20                  25                  30

Ile Ala Tyr Pro Glu Trp Pro Pro Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Phe Val Ile Ile Gln Gly Val Lys Gly Gly Val Glu Ser
 65                  70                  75                  80

Glu Pro Leu Ser Ala Ile Phe Thr Thr
                85
```

<210> SEQ ID NO 242
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Glu Gly Glu Ala Ile Val
        35                  40                  45

Leu Thr Val Pro Gly Ser Glu Arg Ser Tyr Asp Leu Thr Gly Leu Lys
 50                  55                  60

Pro Gly Thr Glu Tyr Trp Val Pro Ile Trp Gly Val Lys Gly Gly Ala
 65                  70                  75                  80

Asn Ser Trp Pro Leu Ser Ala Ile Phe Thr Thr
                85                  90
```

<210> SEQ ID NO 243
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Ser Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Trp Val Pro Ile Trp Gly Val Lys Gly Gly Ala
65                  70                  75                  80

Asn Ser Trp Pro Leu Ser Ala Ile Phe Thr Thr
                85                  90

<210> SEQ ID NO 244
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Tyr Val Pro Ile Trp Gly Val Lys Gly Gly Ala
65                  70                  75                  80

Asn Ser Trp Pro Leu Ser Ala Ile Phe Thr Thr
                85                  90

<210> SEQ ID NO 245
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Phe Val Pro Ile Trp Gly Val Lys Gly Gly Ala
65                  70                  75                  80

Asn Ser Trp Pro Leu Ser Ala Ile Phe Thr Thr
                85                  90

<210> SEQ ID NO 246
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Ser Val Pro Ile Trp Gly Val Lys Gly Gly Ala
65                  70                  75                  80

Asn Ser Trp Pro Leu Ser Ala Ile Phe Thr Thr
                85                  90

<210> SEQ ID NO 247
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Trp Val Pro Ile Tyr Gly Val Lys Gly Gly Ala
65                  70                  75                  80

Asn Ser Trp Pro Leu Ser Ala Ile Phe Thr Thr
                85                  90

<210> SEQ ID NO 248
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys

```
                    50                  55                  60

Pro Gly Thr Glu Tyr Trp Val Pro Ile Phe Gly Val Lys Gly Ala
 65                  70                  75                  80

Asn Ser Trp Pro Leu Ser Ala Ile Phe Thr Thr
                 85                  90
```

<210> SEQ ID NO 249
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                20                  25                  30

Ile Thr Tyr Ile Glu Lys Glu His Ile Glu Asp Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Trp Val Pro Ile Ser Gly Val Lys Gly Ala
 65                  70                  75                  80

Asn Ser Trp Pro Leu Ser Ala Ile Phe Thr Thr
                 85                  90
```

<210> SEQ ID NO 250
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                20                  25                  30

Ile Thr Tyr Ile Glu Lys Glu His Ile Glu Asp Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Trp Val Pro Ile Trp Gly Val Lys Gly Ala
 65                  70                  75                  80

Asn Ser Tyr Pro Leu Ser Ala Ile Phe Thr Thr
                 85                  90
```

<210> SEQ ID NO 251
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

```
Leu Pro Ala Pro Lys Asn Leu Val Val Ser Arg Val Thr Glu Asp Ser
 1               5                  10                  15
```

```
Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
 50                  55                  60

Pro Gly Thr Glu Tyr Trp Val Pro Ile Trp Gly Val Lys Gly Gly Ala
65                   70                  75                  80

Asn Ser Glu Pro Leu Ser Ala Ile Phe Thr Thr
                85                  90

<210> SEQ ID NO 252
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Thr Tyr Ile Glu Lys Glu His Ile Glu Asp Gly Glu Ala Ile Val
        35                  40                  45

Leu Thr Val Pro Gly Ser Glu Arg Ser Tyr Asp Leu Thr Gly Leu Lys
 50                  55                  60

Pro Gly Thr Glu Tyr Trp Val Pro Ile Trp Gly Val Lys Gly Gly Ala
65                   70                  75                  80

Gln Ser Trp Pro Leu Ser Ala Ile Phe Thr Thr
                85                  90

<210> SEQ ID NO 253
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Pro Gly Ser Glu Arg Ser Tyr Asp Leu Thr Gly Leu Lys Pro Gly
 50                  55                  60

Thr Glu Tyr Phe Val Val Ile Thr Gly Val Lys Gly Gly Ala Pro Ser
65                   70                  75                  80

Thr Pro Leu Gly Thr Ile Phe Thr Thr
                85

<210> SEQ ID NO 254
<211> LENGTH: 89
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 254

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Pro Gly Ser Glu Arg Ser Tyr Asp Leu Thr Gly Leu Lys Pro Gly
    50                  55                  60

Thr Glu Tyr Tyr Val Val Ile Thr Gly Val Lys Gly Ala Pro Ser
65                  70                  75                  80

Thr Pro Leu Gly Thr Ile Phe Thr Thr
                85

<210> SEQ ID NO 255
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Leu Tyr Tyr Glu Pro Val Asp Ser Gly Glu Ala Ile Thr Leu Pro
        35                  40                  45

Val Pro Gly Ser Glu Arg Ser Tyr Asp Leu Thr Gly Leu Lys Pro Gly
    50                  55                  60

Thr Glu Tyr His Val Val Ile Thr Gly Val Lys Gly Ala Pro Ser
65                  70                  75                  80

Thr Pro Leu Gly Thr Ile Phe Thr Thr
                85

<210> SEQ ID NO 256
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Tyr Pro Pro Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Ser Tyr Ser
65                  70                  75                  80

Ala Pro Leu Ser Ala Ile Phe Thr Thr
                85

<210> SEQ ID NO 257
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Leu Pro Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Ser Tyr Ser
65                  70                  75                  80

Ala Pro Leu Ser Ala Ile Phe Thr Thr
                85

<210> SEQ ID NO 258
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu Ile Pro Gln Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Val Ile Tyr Gly Val Lys Gly Gly Ser Tyr Ser
65                  70                  75                  80

Ala Pro Leu Ser Ala Ile Phe Thr Thr
                85

<210> SEQ ID NO 259
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Pro Glu His Pro Pro Gln Gly Glu Ala Ile Val Leu Thr 35                  40                  45

Val Pro Gly Ser Glu Arg Ser Tyr Asp Leu Thr Gly Leu Lys Pro Gly
 50                  55                  60

Thr Glu Tyr Phe Val Val Ile Tyr Gly Val Lys Gly Gly Ser Tyr Ser
65                  70                  75                  80

Ala Pro Leu Ser Ala Ile Phe Thr Thr
                85

<210> SEQ ID NO 260
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Thr Tyr Pro Glu Trp Pro Asp Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 261
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
                20                  25                  30

Ile Thr Tyr Pro Glu Trp Pro Asp Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 262
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Thr Tyr Pro Glu Trp Pro Asp Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 263
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Thr Tyr Pro Glu Tyr Pro Asp Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 264
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Thr Tyr Pro Glu Leu Pro Asp Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 265

```
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Thr Tyr Pro Glu Ile Pro Asp Pro Gly Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 266
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Thr Tyr Pro Glu Trp Pro Pro Gly Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Phe Val Val Ile Tyr Gly Val Lys Gly Gly Glu Ile
65                  70                  75                  80

Tyr Ser Pro Leu Ser Ala Ile Phe Thr Thr
                85                  90

<210> SEQ ID NO 267
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Ala Tyr Ala Glu Trp Pro Pro Gln Gly Glu Ala Ile Val Leu Thr
            35                  40                  45

Val Pro Gly Ser Glu Arg Ser Tyr Asp Leu Thr Gly Leu Lys Pro Gly
    50                  55                  60
```

```
Thr Glu Tyr Phe Val Val Ile Tyr Gly Val Lys Gly Gly Ser Tyr Ser
 65                  70                  75                  80

Ala Pro Leu Ser Ala Ile Phe Thr Thr
                 85

<210> SEQ ID NO 268
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
             20                  25                  30

Ile Thr Tyr Ala Glu Trp Pro Asp Pro Gly Gly Glu Ala Ile Val Leu
         35                  40                  45

Thr Val Pro Gly Ser Glu Arg Ser Tyr Asp Leu Thr Gly Leu Lys Pro
     50                  55                  60

Gly Thr Glu Tyr Phe Val Val Ile Tyr Gly Val Lys Gly Gly Glu Ile
 65                  70                  75                  80

Tyr Ser Pro Leu Ser Ala Ile Phe Thr Thr
                 85                  90

<210> SEQ ID NO 269
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Gly
             20                  25                  30

Ile Leu Tyr Tyr Glu Pro Val Asp Ser Gly Glu Ala Ile Thr Leu Thr
         35                  40                  45

Val Pro Gly Ser Glu Arg Ser Tyr Asp Leu Thr Gly Leu Lys Pro Gly
     50                  55                  60

Thr Glu Tyr Trp Val Val Ile Thr Gly Val Lys Gly Gly Ala Pro Ser
 65                  70                  75                  80

Thr Pro Leu Gly Thr Ile Phe Thr Thr
                 85

<210> SEQ ID NO 270
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Leu Pro Ala Pro Lys Asn Leu Val Val Ser Glu Val Thr Glu Asp Ser
 1               5                  10                  15

Ala Arg Leu Ser Trp Thr Ala Pro Asp Ala Ala Phe Asp Ser Phe Leu
```

```
               20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Lys Gly Gly His Arg Ser
 65                  70                  75                  80

Asn Pro Leu Ser Ala Ile Phe Thr Thr
                85

<210> SEQ ID NO 271
<211> LENGTH: 276
<212> TYPE: PRT
<213> ORGANISM: Macaca fascicularis

<400> SEQUENCE: 271

Met Arg Asn Gln Ala Pro Gly Arg Pro Lys Gly Ala Thr Ser Pro Pro
 1               5                  10                  15

Pro Leu Pro Thr Gly Ser Arg Ala Pro Pro Val Ala Pro Glu Leu Arg
            20                  25                  30

Ala Glu Pro Arg Pro Gly Glu Arg Val Met Ala Pro Val Thr Ala
            35                  40                  45

Leu Leu Leu Pro Leu Val Leu Leu Leu His Ala Arg Pro Asn Gln
 50                  55                  60

Phe Arg Val Ser Pro Leu Gly Arg Thr Trp Asn Leu Gly Glu Thr Val
 65                  70                  75                  80

Glu Leu Lys Cys Gln Val Leu Leu Ser Asn Pro Thr Ser Gly Cys Ser
                85                  90                  95

Trp Leu Phe Gln Pro Arg Gly Thr Ala Ala Arg Pro Thr Phe Leu Leu
                100                 105                 110

Tyr Leu Ser Gln Asn Lys Pro Lys Ala Ala Glu Gly Leu Asp Thr Gln
                115                 120                 125

Arg Phe Ser Gly Lys Arg Leu Gly Asp Thr Phe Val Leu Thr Leu Arg
            130                 135                 140

Asp Phe Arg Gln Glu Asn Glu Gly Tyr Tyr Phe Cys Ser Ala Leu Ser
145                 150                 155                 160

Asn Ser Ile Met Tyr Phe Ser His Phe Val Pro Val Phe Leu Pro Ala
                165                 170                 175

Lys Pro Thr Thr Thr Pro Ala Pro Arg Pro Pro Thr Pro Ala Pro Thr
                180                 185                 190

Thr Ala Ser Gln Pro Leu Ser Leu Arg Pro Glu Ala Cys Arg Pro Ala
            195                 200                 205

Ala Gly Gly Ser Val Asn Thr Arg Gly Leu Asp Phe Ala Cys Asp Ile
        210                 215                 220

Tyr Ile Trp Ala Pro Leu Ala Gly Ala Cys Gly Val Leu Leu Leu Ser
225                 230                 235                 240

Leu Val Ile Thr Leu Tyr Cys Asn His Arg Asn Arg Arg Val Cys
                245                 250                 255

Lys Cys Pro Arg Pro Val Val Lys Ser Gly Gly Lys Pro Ser Leu Ser
            260                 265                 270

Asp Arg Tyr Val
        275

<210> SEQ ID NO 272
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Ser Gly Ser
1

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Gly Gly Ser Gly Gly Gly Ser
1               5

<210> SEQ ID NO 274
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 275
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ala Pro Ala Pro
1

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Pro Ala Pro Ala Pro Ala Pro Ala Pro
1               5                   10

<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 277

Ala Pro Ala Pro Ala Pro Ala Pro Ala Pro Ala Pro Ala Pro Ala Pro
1               5                   10                  15

Ala Pro Ala Pro
            20

<210> SEQ ID NO 278
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 279
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Thr Ala Pro Asp Ala Ala Phe Asp
1               5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Lys Gly Gly His Arg Ser Asn Pro
1               5
```

CD8A-BINDING FIBRONECTIN TYPE III DOMAINS

CROSS-REFERENCE TO RELATED APPLICATIONS

This application claims the benefit of U.S. Provisional Application Ser. No. 62/434,017, filed 14 Dec. 2016. The entire contents of the aforementioned application are incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 5, 2017, is named JBI5112USNP_SL.txt and is 256,587 bytes in size.

TECHNICAL FIELD

The present invention relates to fibronectin type III (FN3) domains that specifically bind to cluster of differentiation 8a (CD8a). Such FN3 domains may be used for example, for medical imaging, diagnostics, and pharmaceutical therapy. Methods for the production of such molecules and diagnostic agents comprising them are also provided.

BACKGROUND

The rapidly evolving fields of cancer immunotherapy have recently led to the FDA approval of several new immunotherapies, with many more therapies presently in clinical trials for a variety of cancers. Furthermore, cellular, small molecule, antibody-based immunotherapies, and combinations thereof, are being rigorously tested preclinically for clinical translation. The dynamic tumor microenvironment and tumor heterogeneity have become important topics in both preclinical and clinical studies (Hanahan D, Weinberg R A. Cell 2011; 144:646-74; M antovani A, Allavena P, Sica A, Balkwill F. Nature 2008; 454:436-44; Schreiber R D, Old L J, Smyth M J. Science 2011; 331:1565-70), but the ability to monitor changes in the immune status of primary lesions and metastatic cancers is limited. Current methods to monitor lymphocytes from whole blood or biopsies from heterogeneous tumors do not reflect the dynamic and spatial information likely required to monitor immune responses to therapeutic intervention, many of which elicit whole body changes in immune cell numbers and localization. Therefore, molecular imaging methods that can noninvasively monitor both systemic and intratumoral alterations in immune cell numbers or localization during experimental therapies have the ability to increase the understanding of the dynamics of immunotherapeutic mechanism with the potential to provide translatable methods for predicting and/or assessing clinical immunotherapeutic responses.

Analysis of tumor-infiltrating lymphocytes (TIL) has demonstrated the importance of tumor immune microenvironment and that the presence of cytotoxic CD8+ T cells can predict overall survival in breast, lung, ovarian, melanoma, and colorectal cancers (reviewed in refs. Pages F, et al. Oncogene 2010; 29:1093-102. and Gooden M J, et al. Br J Cancer 2011; 105:93-103). With the recent clinical successes of immunotherapies that alter the tumor immune microenvironment, including adoptive cell transfer (ACT) of T-cell receptor (TCR)- or chimeric antigen receptor-transduced cytotoxic T cells (Johnson L A, et al. Blood 2009; 114:535-46; Rosenberg S A. Sci Transl Med 2012; 4:127ps8), agonistic antibodies targeting CD137 (4-1BB) and CD40 (Melero I, et al. Clin Cancer Res 2013; 19:997-1008; Melero I, et al. Nat Rev Cancer 2007; 7:95-106; Vinay D S, and Kwon B S. Mol Cancer Ther 2012; 11:1062-70), and antibody blockade of the checkpoint inhibitors CTLA-4, PD-1, and PD-L1 (Callahan M K, and Wolchok J D. J Leukoc Biol 2013; 94:41-53; Shin D S, and Ribas A. Curr Opin Immunol 2015; 33C:23-35; Topalian S L, et al. Cancer Cell 2015; 27:450-61), the ability to noninvasively monitor the tumor immune response to therapy has become of upmost importance.

SUMMARY

The present invention comprises CD8A-binding fibronectin type III (FN3) domains. Also described are related polynucleotides capable of encoding the provided FN3 domains, cells expressing the provided FN3 domains, as well as associated vectors. In addition, methods of using the provided FN3 domains are described. For example, the FN3 domains of the invention can be used to noninvasively and quantitatively monitor the presence and abundance of CD8+ T cells.

In some embodiments, the present invention comprises isolated FN3 domains, wherein the FN3 domains bind to a human CD8A comprising SEQ ID NO: 35. In other embodiments, the CD8A-specific FN3 domains bind to human CD8A and cynomolgus monkey CD8A. In yet other embodiments, the CD8A-specific FN3 domains are based on Tencon sequence of SEQ ID NO: 1. In further embodiments, the CD8A-specific FN3 domains are based on the Tencon27 sequence of SEQ ID NO: 4. In some embodiments, the albumin-specific FN3 domains are isolated from the library comprising the sequence of SEQ ID NOs: 2, 3, 5, 6, 7 or 8. In some embodiments, the CD8A-specific FN3 domains do not activate CD8+ T-cells in vitro as measured by the enzyme-linked immunospot (ELISPOT) assay. In some embodiments, the CD8A-specific FN3 domains bind human CD8A with an affinity ($K_D$) of between about 0.02 to about 6.6 nM as measured by surface plasmon resonance. In other embodiments, the CD8A-specific FN3 domains have a cysteine substitution at residue position 54 of SEQ ID NOs 79, 81, 83, 89, 122 and 68. In other embodiments, the CD8A-specific FN3 domains comprise the amino acid sequence of SEQ ID NOs: 40-269. In other embodiments, the CD8A-specific FN3 domains are conjugated to a detectable label.

In addition to the described CD8A-specific FN3 domains, also provided are polynucleotide sequences capable of encoding the described FN3 domains. Vectors comprising the described polynucleotides are also provided, as are cells expressing the CD8A-specific FN3 domains herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). A process for the production of the described FN3 domains is also provided.

The present invention also comprises methods of conjugating or otherwise associating the described CD8A-specific FN3 domains to various molecules for diagnostic purposes. For example, Zr-89 or I-124 are ideal fusion partners for creation of diagnostic agents capable of detecting the presence of CD8+ T-cells. As such, the CD8A-specific FN3 domains have utility in cancer diagnostics using CD8A as a biomarker.

Another embodiment of the invention is a method of detecting CD8A-expressing cells in a biological sample comprising treating the biological sample with a diagnostic agent comprising the described CD8A-specific FN3 domains. These methods are provided in the EXAMPLES.

Within the scope of the invention are kits including the disclosed CD8A-specific FN3 domains. The kits may be used to carry out the methods of using the CD8A-specific FN3 domains provided herein, or other methods known to those skilled in the art. In some embodiments, the described kits may include the FN3 domains described herein and reagents for use in detecting the presence of human CD8A in a biological sample. The described kits may include one or more of the FN3 domains described herein and a vessel for containing the FN3 domains when not in use, instructions for use of the FN3 domains affixed to a solid support, and/or detectably labeled forms of the FN3 domains, as described herein.

BRIEF DESCRIPTION OF DRAWINGS

FIG. 1A includes kidneys, liver and spleen, while FIG. 11B is focused on the spleen. The 24 h time point for [$^{124}$I]-IPEM CD8S365 is missing due to a technical issue. The high uptake of Zr-89 in kidneys due to residualization of the isotope is largely absent from the I-124 data.

DETAILED DESCRIPTION OF ILLUSTRATIVE EMBODIMENTS

Definitions

Figure 1A:
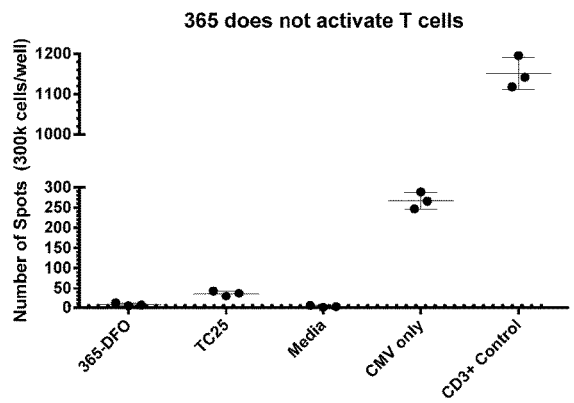
FIG. 1A-1D. The CD8S365-DFO conjugate does not activate T cells de novo and does not modulate the antigen dependent activation of T cells in a 24 hour INF$^\gamma$ EliSpot assay. CMV reactive T cells were treated with 365-DFO in the absence (A) or presence (B) of CMV peptides. A second M1 reactive donor was also tested in the absence (C) or presence (D) of M1 peptides.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" FN3 domain, as used herein, is intended to refer to an FN3 domain which is substantially free of other FN3 domains having different antigenic specificities (for instance, an isolated FN3 domain that specifically binds to human serum albumin is substantially free of FN3 domains that specifically bind antigens other than human serum albumin). An isolated FN3 domain that specifically binds to an epitope, isoform or variant of human serum albumin may, however, have cross-reactivity to other related antigens, for instance from other species (such as serum albumin species homologs).

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al. J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

"Centyrin" as used herein refers to a FN3 domain that is based on the consensus sequence of the 15 different FN3 domains present in human tenascin C.

The term "capture agent" refers to substances that bind to a particular type of cells and enable the isolation of that cell from other cells. Examples of capture agents include but are not limited to magnetic beads, ferrofluids, encapsulating reagents and the like.

The term "biological sample" refers to blood, tissue, marrow, sputum and the like.

The term "diagnostic reagent" refers to any substance that may be used to analyze a biological sample, whether or not such substance is distributed as a single substance or in a combination with other substances in a diagnostic kit.

The term "substituting" or "substituted" or 'mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Typically the FN3 domain of the invention binds to a predetermined antigen (i.e. human CD8A) with a $K_D$ that is at least ten fold less than its $K_D$ for a nonspecific antigen (for example BSA or casein) as measured by surface plasmon resonance using for example a Proteon Instrument (BioRad). The isolated FN3 domain of the invention that specifically binds to human CD8A may, however, have cross-reactivity to other related antigens, for example to the same predetermined antigen from other species (orthologs), such as *Macaca Fascicularis* (cynomolgus monkey, cyno) or *Pan troglodytes* (chimpanzee).

The term "library" refers to a collection of variants. The library may be composed of polypeptide or polynucleotide variants.

As used herein, the terms "CD8A" or "CD8" specifically include the human CD8 alpha protein, for example, as described in NCBI Reference Sequence: NP_001139345.1, NP_0011759.3, and NP_741969.1. CD8A is also known in the scientific literature as CD8a molecule, MAL, p32, Leu2, T-cell surface glycoprotein CD8 alpha chain, CD8 antigen, alpha polypeptide (p32), Leu2 T-lymphocyte antigen, OKT8 T-cell antigen, T-cell antigen Leu2, T-lymphocyte differentiation antigen T8/Leu-2, and T8 T-cell antigen.

"Tencon" as used herein refers to the synthetic fibronectin type III (FN3) domain having the sequence shown in SEQ ID NO: 1 and described in U.S. Pat. Publ. No. US2010/0216708.

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than about 50 amino acids may be referred to as "peptides".

The term "in combination with" as used herein means that two or more therapeutics can be administered to a subject together in a mixture, concurrently as single agents or sequentially as single agents in any order.

Compositions of Matter

The present invention provides human CD8A binding FN3 domains and CD8A binding FN3 domains conjugated to detectable labels. The present invention provides polynucleotides encoding the FN3 domains of the invention or complementary nucleic acids thereof, vectors, host cells, and methods of making and using them.

CD8A Binding Molecules

The present invention provides fibronectin type III (FN3) domains that bind specifically to CD8A, optionally conjugated to a detectable label. These molecules may be widely used in preclinical applications and in cancer diagnostics using CD8A as a biomarker. The present invention provides polynucleotides encoding the FN3 domains of the invention or complementary nucleic acids thereof, vectors, host cells, and methods of making and using them.

The FN3 domains of the invention bind CD8A with high affinity and can localize CD8-expressing cells, thereby providing an efficient way to deliver diagnostic reagents into tumor microenvironment.

One embodiment of the invention an isolated FN3 domain that specifically binds a human CD8A comprising the amino acid sequence of SEQ ID NO: 35.

In some embodiment of the invention described herein, the FN3 domain of the invention cross-reacts with cynomolgus monkey CD8A having the amino acid sequence of SEQ ID NO: 271.

The FN3 domain of the invention may bind human, *Macaca Fascicularis* and/or *Pan troglodytes* CD8A with a dissociation constant ($K_D$) of less than about $1\times10^{-7}$ M, for example less than about $1\times10^{-8}$ M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

In some embodiments, the CD8A binding FN3 domains comprise an initiator methionine (Met) linked to the N-terminus of the molecule.

In some embodiments, the CD8A binding FN3 domains comprise a cysteine (Cys) linked to the FN3 domain.

The addition of the N-terminal Met and/or the Cys may facilitate expression and/or conjugation of second molecules.

Another embodiment of the invention is an isolated FN3 domain that specifically binds human CD8A and wherein the CD8A-specific FN3 domain does not activate CD8+ T-cells in vitro. CD8+ T cell activation may be measured using standard methods. For example, the enzyme-linked immunospot (ELISPOT) assay may be used. The ELISPOT assay employs the sandwich enzyme-linked immunosorbent assay (ELISA) technique. The interferon-gamma antibody is pre-coated onto a PVDF (polyvinylidene difluoride)-backed microplate. Appropriately stimulated cells (cells+peptides, FN3 domains, etc) are pipetted into the wells and the microplate is placed into a humidified 37° C. $CO_2$ incubator for a specified period of time. During this incubation period, the immobilized interferon-gamma antibody, in the immediate vicinity of the secreting cells, binds the secreted interferon gamma. After washing away any cells and unbound substances, a second biotinylated interferon-gamma antibody is added to the wells. Following a wash to remove any unbound biotinylated antibody, alkaline-phosphatase conjugated to streptavidin is added.

Unbound enzyme is subsequently removed by washing and a substrate solution (BCIP/NBT) is added. A blue-black colored precipitate forms and appears as spots at the sites of interferon-gamma localization, with each individual spot representing an individual interferon gamma-secreting cell. The spots can be counted with an automated ELISpot reader system or manually, using a stereomicroscope. The isolated CD8A binding FN3 domains of the invention do not activate CD8+ T-cells in vitro when tested at 1 µM concentrations as described in the EXAMPLES.

In some embodiments of the invention described herein, the isolated FN3 domain comprises the amino acid sequence of SEQ ID NOs: 40-269.

In some embodiments of the invention described herein, the CD8A-specific FN3 domain has a cysteine substitution at residue position 54 of SEQ ID NOs 79, 81, 83, 89, 122 and 68.

Substitutions resulting in introduction of cysteine into a protein sequence may be utilized to chemically conjugate small molecules such as cytotoxic agents, detectable labels, half-life extension molecules, chelators, polyethylene glycol and/or nucleic acids to the FN3 domain using standard chemistry.

In some embodiments, the FN3 domain specifically binding human CD8A competes for binding to human CD8A with the FN3 domain of SEQ ID NOs: 229-234. FN3 domains may be evaluated for there competition with a reference molecule for binding human CD8A using well known in vitro methods. In an exemplary method, HEK cells recombinantly expressing human CD8A may be incubated with unlabeled reference molecule for 15 min at 4° C., followed by incubation with an excess of fluorescently labeled test FN3 domain for 45 min at 4° C. After washing in PBS/BSA, fluorescence may be measured by flow cytometry using standard methods. In another exemplary method, extracellular portion of human CD8A may be coated on the surface of an ELISA plate. Excess of unlabelled reference molecule may be added for about 15 minutes and subsequently biotinylated test FN3 domains may be added. After washes in PBS/Tween, binding of the test biotinylated FN3 domain may be detected using horseradish peroxidase (HRP)-conjugated streptavidine and the signal detected using standard methods. It is readily apparent that in the competition assays, reference molecule may be labelled and the test FN3 domain unlabeled. The test FN3 domain may compete with the reference molecule when the reference molecule inhibits binding of the test FN3 domain, or the test FN3 domain inhibits binding of the reference molecule by 20%, 30%, 40%, 50%, 60%, 70%, 80%, 85%, 90%, 95% or 100%.

In some embodiments, the isolated FN3 domain that specifically binds human CD8A of the invention is conjugated to a chelator that can bind to a radioactive metal and may be used as an imaging agent to evaluate tumor distribution, diagnosis for the presence of CD8-T cells inside tumors and/or efficacy of cancer treatment.

In some embodiments, the CD8A-specific FN3 domains are removed from the blood via renal and/or liver clearance.

Isolation of CD8A Binding FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708).

The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD8A. Table 1 shows positions and sequences of each loop and beta-strand in Tencon (SEQ ID NO: 1).

Library designed based on Tencon sequence may thus have randomized FG loop, or randomized BC and FG loops, such as libraries TCL 1 or TCL2 as described below. The Tencon BC loop is 7 amino acids long, thus 1, 2, 3, 4, 5, 6 or 7 amino acids may be randomized in the library diversified at the BC loop and designed based on the Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

A library designed based on the Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

| Tencon topology | |
|---|---|
| FN3 domain | Tencon (SEQ ID NO: 1) |
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_// www_sloning_com). This technology uses a library of premade double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding human CD8A of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al. Proc Natl Acad Sci USA 101, 2806-2810, 2004), and assaying the library for specific binding to CD8A by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding CD8A are further characterized for their inhibition of CD8A activity, internalization, stability, and other desired characteristics.

The FN3 domains specifically binding human CD8A of the invention may be generated using any FN3 domain as a template to generate a library and screening the library for molecules specifically binding human CD8A using methods provided within. Exemplar FN3 domains that may be used are the 3rd FN3 domain of tenascin C (TN3) (SEQ ID NO: 145), Fibcon (SEQ ID NO: 146), and the 10 FN3 domain of fibronectin (FN10) (SEQ ID NO: 147). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

In some embodiments of the invention described herein, the FN3 domain specifically binding human CD8A is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

The FN3 domains specifically binding human CD8A of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domains specifically binding human CD8A of the invention may exhibit increased stability by at least 5%, 10%, 15%, 20%, 25%, 30%, 35%, 40%,45%, 50%, 55%, 60%, 65%, 70%, 75%, 80%, 85%, 90%, or 95% or more compared to the same domain prior to engineering measured by the increase in the $T_m$. Chemical denaturation can likewise be measured by a variety of methods.

Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules.

The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include (GS)$_2$, (SEQ ID NO: 148), (GGGS)$_2$ (SEQ ID NO: 149), (GGGGS)$_5$ (SEQ ID NO: 150), (AP)$_2$ (SEQ ID NO: 151), (AP)$_5$ (SEQ ID NO: 152), (AP)$_{10}$ (SEQ ID NO: 153), (AP)$_{20}$ (SEQ ID NO: 154) and A(EAAAK)$_5$AAA (SEQ ID NO: 142). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al. *Protein Eng.* 8, 725-731, 1995; *Robinson & Sauer, Biochemistry* 35, 109-116, 1996; U.S. Pat. No. 5,856,456).

Diagnostic Agents

According to the invention, a CD8A-specific FN3 domain of the invention may comprise a detectable label. In an embodiment, the detectable label may be complexed with a chelating agent that is conjugated to the FN3 domain. In another embodiment, the detectable label may be complexed with a chelating agent that is conjugated to a linker that is conjugated to the FN3 domain. In still another embodiment, the detectable label may be coupled to a linker that is conjugated to the FN3 domain. In still yet another embodiment, a detectable label may be indirectly attached to a peptide of the invention by the ability of the label to be specifically bound by a second molecule. One example of this type of an indirectly attached label is a biotin label that can be specifically bound by the second molecule, streptavidin. Single, dual or multiple labeling may be advantageous. As used herein, a "detectable label" is any type of label which, when attached to an FN3 domain of the invention renders the FN3 domain detectable. A detectable label may also be toxic to cells or cytotoxic. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, Ni$^{2+}$, Flag tags, myc tags, heavy metals, enzymes, alkaline phosphatase, peroxidase, luciferase, electron donors/acceptors, acridinium esters, and colorimetric substrates. In a specific embodiment, the detectable label is a radionuclide. The skilled artisan would readily recognize other useful labels that are not mentioned above, which may be employed in the operation of the present invention.

A detectable label emits a signal that can be detected by a signal transducing machine. In some cases, the detectable label can emit a signal spontaneously, such as when the detectable label is a radionuclide. In other cases, the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. An FN3 domain of the invention can be labeled for fluorescence detection by labeling the agent with a fluorophore using techniques well known in the art (see, e.g., Lohse et al., Bioconj Chem 8:503-509 (1997)). For example, many known dyes are capable of being coupled to NH$_2$-terminal amino acid residues. Alternatively, a fluorochrome such as fluorescein may be bound to a lysine residue of the peptide linker.

A radionuclide may be a γ-emitting radionuclide, Auger-emitting radionuclide, β-emitting radionuclide, an alpha-emitting radionuclide, or a positron-emitting radionuclide. A radionuclide may be a detectable label and/or a cytotoxic agent Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97, 103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121 m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-21 1, bismuth-212 and 213, lead-212, radium-223, actinium-225, and nitride or oxide forms derived there from. In a specific embodiment, a radionuclide is selected from the group consisting of copper-64, zirconium-89, yttrium-90, indium-111, and lutetium-177. In another specific embodiment, a radionuclide is selected from the group consisting of yttrium-90, indium-111, and lutetium-177. In an exemplary embodiment, a radionuclide is zirconium-89.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{4+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

According to the invention, an FN3 domain comprising a chelating agent may incorporate a radionuclide or metal atom. Incorporation of the radionuclide or metal atom with an FN3domain-chelating agent complex may be achieved by various methods common in the art of coordination chemistry.

Half-Life Extending Moieties

The FN3 domain specifically binding human CD8A of the invention may incorporate other subunits for example via covalent interaction. In one aspect of the invention, the FN3 domain of the invention further comprises a half-life extending moiety. Exemplary half-life extending moieties are albumin, albumin variants, albumin-binding proteins and/or domains, transferrin and fragments and analogues thereof, and Fc regions.

Additional moieties may be incorporated into the FN3 domain of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain of the invention by incorporating a cysteine residue to the C-terminus of the molecule, or engineering cysteines into residue positions that face away from the human CD8A binding face of the molecule, and attaching a pegyl group to the cysteine using well known methods. FN3 domain of the invention incorporating additional moieties may be compared for functionality by several well known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the FN3 domains specifically binding human CD8A of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

One embodiment of the invention is an isolated polynucleotide encoding the FN3 domain specifically binding human CD8A comprising the amino acid sequence of SEQ ID NOs: 40-269.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. The FN3 domain specifically binding human CD8A of the invention may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al. Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp. *Klebsiella* spp., or *Pseudomonas* spp strains.

Another embodiment of the invention is a method of producing the isolated FN3 domain specifically binding human CD8A of the invention, comprising culturing the isolated host cell of the invention under conditions such that the isolated FN3 domain specifically binding human CD8A is expressed, and purifying the FN3 domain.

The FN3 domain specifically binding human CD8A may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Kits for Detecting Human CD8A

Provided herein are kits for detecting CD8A in a biological sample. These kits include one or more of the CD8A-specific FN3 domains described herein and instructions for use of the kit.

The provided CD8A-specific FN3 domain may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of CD8A can further include, for example, buffers or other reagents for use in an assay for determining the level of CD8A. The instructions can be, for example, printed instructions for performing the assay and/or instructions for evaluating the level of CD8A.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Uses of Human CD8A Binding FN3 Domains of the Invention

The FN3 domains specifically binding human CD8A of the invention may be used to diagnose human disease or specific pathologies in cells, tissues, organs, fluid, or, generally, a host, using CD8A as a biomarker. The methods of the invention may be used in an animal patient belonging to any classification. Examples of such animals include mammals such as humans, rodents, dogs, cats and farm animals.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:

(SEQ ID NO 1):
LPAPKNLVVSEVTEDSLRLSWTAPDAAFDSFLIQYQESEKVGEAINLTVP

GSERSYDLTGLKPGTEYTVSIYGVKGGHRSNPLSAEFTT

Various libraries were generated using the tencon scaffold and various design strategies. In general, libraries TCL 1 and TCL2 produced good binders. Generation of TCL 1 and TCL2 libraries are described in detail in Int. Pat. Publ. No. WO2014081944A2.

Construction of TCL1 Library

A library designed to randomize only the FG loop of Tencon (SEQ ID NO: 1), TCL 1, was constructed for use with the cis-display system (Jacobs et al., Protein Engineering, Design, and Selection, 25:107-117, 2012). In this system, a double-stranded DNA incorporating sequences for a Tac promoter, Tencon library coding sequence, RepA coding sequence, cis-element, and on element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and on elements. These two halves are combined by restriction digest in order to produce the entire construct. The TCL 1 library was designed to incorporate random amino acids only in the FG loop of Tencon, KGGHRSN (SEQ ID NO: 32). NNS codons were used in the construction of this library, resulting in the possible incorporation of all 20 amino acids and one stop codon into the FG loop. The TCL 1 library contains six separate sub-libraries, each having a different randomized FG loop length, from 7 to 12 residues, in order to further increase diversity.

TCL1 library
(SEQ ID NO: 2)
LPAPKNLVVSEVTEDSLRLSWTAPDAAFDSFLIQYQESEKVGEAINLTVP

GSERSYDLTGLKPGTEYTVSIYGVX$_{7-12}$PLSAEFTT;

wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted
Construction of TCL2 Library TCL2 library was constructed in which both the BC and the FG loops of Tencon were randomized and the distribution of amino acids at each position was strictly controlled. Table 2 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 1 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library
(SEQ ID NO: 3)
LPAPKNLVVSEVTEDSLRLSWX$_1$X$_2$X$_3$X$_4$X$_5$X$_6$X$_7$X$_8$SFLIQYQESEKVGEAI NLTVPGSERSYDLTGLKPGTEYTVSIYGVX$_9$X$_{10}$X$_{11}$X$_{12}$X$_{13}$SX$_{14}$X$_{15}$LSAE FTT; wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 1

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No.

WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                           (SEQ ID NO: 4)
LPAPKNLVVSRVTEDSARLSWTAPDAAFDSFLIQYQESEKVGEAIVLTVP

GSERSYDLTGLKPGTEYTVSIYGVKGGHRSNPLSAIFTT

TCL7 (randomized FG and BC loops)
                                           (SEQ ID NO: 5)
LPAPKNLVVSRVTEDSARLSWX₁X₂X₃X₄X₅X₆X₇X₈X₉FDSFLIQYQESE

KVGEAIVLTVPGSERSYDLTGLKPGTEYTVSIYGVX₁₀X₁₁X₁₂X₁₃X₁₄X₁₅

X₁₆X₁₇X₁₈X₁₉SNPLSAIFTT;

wherein

X₁, X₂, X₃, X₄, X₅, X₆, X₁₀, X₁₁, X₁₂, X₁₃, X₁₄, X₁₅ and

X₁₆ is A, D, E, F, G, H, I, K, L, N, P, Q, R, S, T,

V, W or Y; and X₇, X₈, X₉, X₁₇, X₁₈ and X₁₉, is A, D,

E, F, G, H, I, K, L, N, P, Q, R, S, T, V, W, Y or deleted.

TCL9 (randomized FG loop)
                                           (SEQ ID NO: 6)
LPAPKNLVVSRVTEDSARLSWTAPDAAFDSFLIQYQESEKVGEAIVLTVP

GSERSYDLTGLKPGTEYTVSIYGV X₁X₂X₃X₄X₅X₆X₇X₈X₉X₁₀X₁₁X₁₂SNP

LSAIFTT; X₁, X₂, X₃, X₄, X₅, X₆ and X₇, is A, D, E,

F, G, H, I, K, L, N, P, Q, R, S, T, V, W or Y; and

X₈, X₉, X₁₀, X₁₁ and X₁₂ is A, D, E, F, G, H, I, K,

L, N, P, Q, R, S, T, V, W, Y or deleted.
```

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 pg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 pg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID No. 13-16) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83 mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide endoding for amino acid A17 (130mer-L17A, SEQ ID No. 17) was produced by PCR using oligos POP2222ext (SEQ ID No. 18) and LS1114 (SEQ ID No. 19). his was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID No. 20) and LS1117 (SEQ ID No. 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7 (SEQ ID No. 31), FG8 (SEQ ID No. 30), FG9 (SEQ ID No. 29), FG10 (SEQ ID No. 28), FG11 (SEQ ID No. 27), and FG12 (SEQ ID No. 26) as templates with oligonucleotides SDG10 (SEQ ID No. 22) and SDG24 (SEQ ID No. 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID No. 24) and SDG28 (SEQ ID No. 25). 7.5 pg of each reaction product were then digested with NotI and cleaned up with a Qiagen PCR purification column. 5.2 pg of this DNA, was ligated to an equal molar amount of RepA DNA fragment (~14 pg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. 2013/0226834.

TCL14 library (SEQ ID NO: 7):
LPAPKNLVVSRVTEDSARLSWTAPDAAFDSFX$_1$IX$_2$YX$_3$EX$_4$X$_5$X$_6$X$_7$GEAI

VLTVPGSERSYDLTGLKPGTEYX$_8$VX$_9$IX$_{10}$GVKGGX$_{11}$X$_{12}$SX$_{13}$PLSAIFT

T;

Wherein $X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V, W, Y, or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL 14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL 14 design, they could be included in subsequent library designs to provide additional diversity for de novo selection or for example for an affinity maturation library on a select TCL 14 target specific hit.

Subsequent to the production of TCL 14, 3 additional Tencon libraries of similar design were produced. These two libraries, TCL19, TCL21 and TCL23, are randomized at the same positions as TCL14 (see above) however the distribution of amino acids occurring at these positions is altered (Table 2). TCL 19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 2. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 2.

TCL24 Library (SEQ ID NO: 8)
LPAPKNLVVSRVTEDSARLSWTAPDAAFDSFX$_1$IX$_2$YX$_3$EX$_4$X$_5$X$_6$X$_7$GEAI X$_8$LX$_9$VPGSERSYDLTGLKPGTEYX$_{10}$VX$_{11}$IX$_{12}$GVKGGX$_{13}$X$_{14}$SX$_{15}$PLX$_{16}$

AX$_{17}$FTT;

wherein $X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V or W.

TABLE 2

Amino acid frequency (%) at each randomized position for TCL21, TCL23, and TCL24.

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL 19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3: Selection of Fibronectin Type III (FN3) Domains that Bind CD8A

Design and Production of Human CD8 Alpha Antigens:
Two human CD8 alpha (Swiss Prot P01732) constructs were expressed and purified from HEK cells to produce recombinant protein for CIS-Display panning (Table 3).

TABLE 3

CD8A constructs generated for use as antigens

| Construct | SEQID No. | Description |
|---|---|---|
| CD8W7 | 35 | Human CD8 alpha residues 22-167 fused to Fc fragment of human IgG1 |
| CD8W13 | 36 | Human CD8 alpha residues 22-182 fused to Fc fragment of human IgG1 |

Each construct was designed to include a murine IgG Kappa secretion signal (SEQ ID No 3) and was fused to the Fc fragment of human IgG1 (SEQID No. 4). The CD8 alpha and Fc fragment sequences were connected by a linker containing a flag and polyhistidine tag sequence (SEQID No 5.)

Plasmids encoding these proteins were transfected into HEK 293-Expi cells by transient transfection and culture supernatants were harvested by centrifugation at 6000×g and clarified with a 0.2 micron filter. Supernatants were loaded onto a HiTrap Mabsure Select column (GE Healthcare) and CD8A proteins eluted in 0.1 M Na-Acetate pH 3.5 and neutralized by addition of 2M Tris pH 7. Each sample was then dialyzed into PBS pH 7.4 for biotinylation with a No Weigh EZ-Link-Sulfo-NHS-LC-Biotin biotinylation kit (Thermo Scientific).

Library Screening

Cis-display was used to select human CD8 alpha-binding domains from the TCL18, TCL19, TCL21, TCL23, and TCL24 libraries. Biotinylated CD8W7 and CD8W13 were used for panning. For in vitro transcription and translation (ITT), 3 pg of library DNA were incubated with 0.1 mM complete amino acids, 1× S30 premix components, and 15 µL of S30 extract (Promega) in a total volume of 50 µL and incubated at 30° C. After 1 hour, 375 µL of blocking solution ((0.1% Casein (Thermo Fisher, Rockford, Ill.), 100 mg/ml Herring Sperm DNA (Promega, Madison, Wis.), 1 mg/mL heparin (Sigma-Aldrich, St. Louis, Mo.)) was added and the reaction was incubated on ice for 15 minutes. For selection, biotinylated antigen was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, Ill.) (Rounds 1, 3, and 5) or streptavidin magnetic beads (Promega, Madison, Wis.) (Rounds 2 and 4) and unbound library members were removed by washing the beads 5-14 times with 500 µL PBST followed by 2 washes with 500 µL PBS. Additional selection rounds were performed in order to identify scaffold molecules with improved affinities. Briefly, outputs from round 5 were prepared as described above and subjected to additional iterative rounds of selection with the following changes: the biotinylated target concentration decreased to 25 nM (Rounds 6 and 7) or 2.5 nM (Rounds 8 and 9), and an additional 1 hour wash was performed in the presence of an excess of non-biotinylated target protein. The goal of these changes was to simultaneously select for binders with a potentially faster on-rate and a slower off-rate yielding a substantially lower $K_D$.

Following panning, selected FN3 domains were amplified by PCR using oligos Tcon6 (SEQID NO: 33) and Tcon5shortE86I (SEQID NO: 34), subcloned by annealing into a pET15-LIC and transformed into BL21-GOLD (DE3) cells (Agilent, Santa Clara, Calif.) for soluble expression in E. coli using standard molecular biology techniques. Single clones were picked and grown to saturation in 1 mL LB with ampicillin in 96 deepwell plates at 37° C. The following day, 25 uL was transferred to fresh 1 mL LB-Amp media in 96 deepwell plates and grown at 37° C. for 2 hours. IPTG was added at 1 mM final concentration and protein expression was induced at 30° C. for 16 hours. The cells were harvested by centrifugation and subsequently lysed with Bugbuster HT (EMD Chemicals, Gibbstown, N.J.) supplemented with 0.2 mg/mL final Chicken Egg White Lysozyme (Sigma-Aldrich, St. Louis, Mo.). Cells were harvested approximately 16 hours later by centrifugation and frozen at −20° C. Cell lysis was achieved by incubating each pellet in 0.6 mL of Bug-Buster® HT lysis buffer (Novagen EMD Biosciences) with shaking at room temperature for 45 minutes.

Selection of FN3 Domains that Bind CD8A

Neutravidin-coated plates were blocked for 1 hour in Starting Block T20 (Pierce) and then coated with biotinylated CD8W7 or CD8W13 (same antigen as in panning) or negative control (human Fc) for 1 hour. Plates were rinsed with TBST and diluted lysate was applied to plates for 1 hour. Following additional rinses, wells were treated with HRP-conjugated anti-FN3 domain antibody (PAB25) for 1 h and then assayed with POD (Roche). FN3 domain molecules with signals at least 10-fold above background were selected for further analysis.

Small Scale Expression and Purification of Identified FN3 Domains Binding CD8A

Isolated clones from unique hits identified by biochemical binding ELISA were combined into a single hit plate for growth in 96-well block plates; clones grew in 1 mL cultures (LB media supplemented with kanamycin for selection) at 37° C. overnight with shaking. For protein expression in 96-block plates, 1 mL TB media supplemented with kanamycin was inoculated with 50 uL of the overnight culture and grown at 37° C. with continual shaking at 300 rpm until $OD_{600}$=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Pellets were lysed with BugBuster® HT lysis buffer (Novagen EMD Biosciences) and His-tagged Centyrins purified from the clarified lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of anti-CD8 alpha FN3 domain molecules. Aliquots (10 μL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Wild-type Tencon was included in each run as a control. Agilent ChemStation software was used to analyse the elution profiles. Only those proteins with elution profiles similar to that of the tenascin consensus protein in the same run were considered for further characterization. After panning, ELISA screening and size exclusion chromatographic analysis, a total of 190 unique anti-human CD8 alpha FN3 domains were isolated that bound to recombinant human CD8 alpha greater than 10-fold over background and were free of aggregates by SEC (Table 4, SEQID no. 40-228, and 70).

TABLE 4

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P282AR9P1356_A10 | 40 | 4258 | 2093 | 2.91E−04 | 10584 | 3122 |
| P282AR9P1356_A4 | 41 | 16674 | 4380 | 8.61E−05 | 26447 | 8632 |
| P282AR9P1356_A6 | 42 | 10835 | 3441 | 9.73E−05 | 31432 | 5783 |
| P282AR9P1356_B9 | 43 | 17158 | 3670 | 2.95E−04 | 36397 | 5437 |
| P282AR9P1356_D3 | 44 | 5963 | 2403 | 1.58E−04 | 13852 | 3365 |
| P282AR9P1356_H1 | 45 | 14696 | 3234 | 1.14E−04 | 46317 | 5699 |
| P282AR9P1356_H6 | 46 | 6646 | 2642 | 8.08E−05 | 14393 | 3205 |
| P282BR9P1357_A9 | 47 | 3117 | 1074 | 5.90E−04 | 7281 | 1940 |
| P282BR9P1357_B2 | 48 | 5931 | 2875 | 1.00E−04 | 17974 | 3841 |
| P282BR9P1357_C10 | 49 | 9779 | 2901 | 4.58E−04 | 24476 | 5110 |
| P282BR9P1357_C4 | 50 | 16809 | 4224 | 1.27E−04 | 41586 | 7064 |
| P282BR9P1357_D12 | 51 | 15269 | 3899 | 8.76E−05 | 40450 | 7364 |
| P282BR9P1357_D2 | 52 | 9606 | 1568 | 1.05E−03 | 25843 | 2525 |
| P282BR9P1357_E5 | 53 | 6726 | 2587 | 2.10E−04 | 10563 | 4101 |
| P282BR9P1357_G9 | 54 | 12733 | 2803 | 3.04E−04 | 41492 | 4635 |
| P282BR9P1357_H3 | 55 | 11142 | 3033 | 2.85E−04 | 27090 | 5701 |
| P282CR9P1358_C2 | 56 | 10086 | 1059 | 1.13E−03 | 55786 | 7047 |
| P282CR9P1358_C5 | 57 | 2706 | 511 | 9.99E−04 | 25688 | 1831 |
| P282CR9P1358_D10 | 58 | 28650 | 2764 | 3.11E−04 | 74051 | 4072 |
| P282CR9P1358_F11 | 59 | 6420 | 749 | 1.35E−03 | 62412 | 6585 |
| P282CR9P1358_F5 | 60 | 24427 | 3072 | 6.37E−04 | 85691 | 13667 |
| P282DR9P1359_A12 | 61 | 32222 | 5952 | 8.12E−05 | 88032 | 15491 |
| P282DR9P1359_A7 | 62 | 38382 | 8764 | 7.54E−04 | 83943 | 22803 |
| P282DR9P1359_A8 | 63 | 21124 | 2113 | 6.38E−04 | 70263 | 7766 |
| P282DR9P1359_B2 | 64 | 22228 | 2726 | 6.38E−04 | 60866 | 4472 |
| P282DR9P1359_C10 | 65 | 27822 | 2879 | 9.91E−04 | 98481 | 15134 |
| P282DR9P1359_C11 | 66 | 18176 | 1288 | 2.16E−03 | 19916 | 457 |
| P282DR9P1359_C12 | 67 | 15106 | 944 | 9.78E−04 | 66538 | 3636 |
| P282DR9P1359_C5 | 68 | 31017 | 5551 | 1.74E−04 | 95679 | 14183 |
| P282DR9P1359_D12 | 69 | 4540 | 542 | 1.93E−03 | 37139 | 1746 |
| P282DR9P1359_E11 | 70 | 40607 | 7578 | 2.65E−04 | 104291 | 33144 |
| P282DR9P1359_E2 | 71 | 28491 | 4824 | 2.06E−03 | 77725 | 10939 |
| P282DR9P1359_E3 | 72 | 4307 | 349 | 2.63E−03 | 52426 | 1625 |
| P282DR9P1359_E5 | 73 | 24100 | 1954 | 1.01E−03 | 81183 | 13601 |
| P282DR9P1359_E6 | 74 | 20507 | 1262 | 1.71E−03 | 61734 | 5065 |
| P282DR9P1359_E8 | 75 | 26074 | 2919 | 1.19E−03 | 80973 | 16948 |
| P282DR9P1359_F11 | 76 | 35639 | 6592 | 5.54E−04 | 86740 | 16146 |
| P282DR9P1359_F2 | 77 | 18415 | 3047 | 7.22E−04 | 38228 | 4031 |
| P282DR9P1359_F3 | 78 | 6343 | 646 | 1.06E−03 | 48861 | 3084 |
| P282DR9P1359_F5 | 79 | 48931 | 8483 | 9.02E−05 | 113733 | 34709 |
| P282DR9P1359_F6 | 80 | 19937 | 3782 | 3.89E−04 | 73219 | 10680 |
| P282DR9P1359_F7 | 81 | 38323 | 6932 | 3.65E−04 | 96456 | 26331 |
| P282DR9P1359_G4 | 82 | 26568 | 2670 | 5.17E−04 | 78619 | 6006 |
| P282DR9P1359_G7 | 83 | 37626 | 6129 | 1.14E−04 | 69085 | 8769 |
| P282DR9P1359_H5 | 84 | 919 | 278 | 4.49E−03 | 2252 | 500 |

TABLE 4-continued

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P282ER9P1360_A9 | 85 | 23379 | 5344 | 1.33E-04 | 64694 | 8732 |
| P282ER9P1360_C1 | 86 | 25874 | 6291 | 1.81E-04 | 64813 | 9679 |
| P282ER9P1360_C4 | 87 | 19202 | 3459 | 1.07E-03 | 33427 | 3896 |
| P282ER9P1360_C6 | 88 | 25942 | 5079 | 1.75E-04 | 52783 | 7579 |
| P282ER9P1360_C8 | 89 | 30578 | 6013 | 1.56E-04 | 66829 | 10220 |
| P282ER9P1360_D11 | 90 | 36755 | 3210 | 1.42E-04 | 76564 | 1937 |
| P282ER9P1360_E4 | 91 | 26889 | 5030 | 1.91E-04 | 60757 | 6867 |
| P282ER9P1360_F11 | 92 | 22442 | 3863 | 2.25E-04 | 48653 | 4407 |
| P282ER9P1360_G10 | 93 | 26951 | 7046 | 2.07E-03 | 62701 | 22641 |
| P282ER9P1360_G7 | 94 | 25438 | 5869 | 2.21E-04 | 69709 | 9921 |
| P282ER9P1360_H10 | 95 | 2513 | 506 | 1.04E-03 | 27063 | 1887 |
| P282ER9P1360_H2 | 96 | 15165 | 3479 | 2.69E-04 | 44563 | 4535 |
| P282ER9P1360_H3 | 97 | 19992 | 4271 | 2.42E-04 | 65994 | 6441 |
| P282FR9P1361_A3 | 98 | 7670 | 1661 | 7.57E-04 | 8476 | 740 |
| P282FR9P1361_A5 | 99 | 32752 | 5213 | 1.92E-04 | 63541 | 8108 |
| P282FR9P1361_C7 | 100 | 8538 | 1575 | 2.24E-03 | 11639 | 896 |
| P282FR9P1361_D3 | 101 | 6881 | 1028 | 5.02E-03 | 14762 | 764 |
| P282FR9P1361_E12 | 102 | 15794 | 1130 | 1.09E-03 | 63536 | 15052 |
| P282FR9P1361_F1 | 103 | 5498 | 801 | 1.26E-03 | 9869 | 1392 |
| P282FR9P1361_F11 | 104 | 2189 | 382 | 2.13E-03 | 2289 | 384 |
| P282FR9P1361_F2 | 105 | 4610 | 498 | 4.96E-03 | 10883 | 462 |
| P282FR9P1361_F3 | 106 | 5157 | 674 | 1.07E-02 | 9709 | 513 |
| P282FR9P1361_F7 | 107 | 7001 | 1107 | 1.14E-03 | 1705 | 353 |
| P282FR9P1361_G9 | 108 | 859 | 297 | 6.53E-03 | 3746 | 666 |
| P282FR9P1361_H4 | 109 | 13056 | 3736 | 3.17E-04 | 26273 | 2504 |
| P282FR9P1361_H5 | 110 | 5730 | 698 | 5.77E-03 | 11794 | 637 |
| P283AR9P1362_A3 | 111 | 5535 | 1400 | 1.53E-03 | 17345 | 3533 |
| P283AR9P1362_A4 | 112 | 6314 | 2539 | 3.02E-04 | 21218 | 4402 |
| P283AR9P1362_B10 | 113 | 15380 | 3703 | 1.39E-04 | 35686 | 8380 |
| P283AR9P1362_B2 | 114 | 13649 | 3505 | 1.60E-04 | 38828 | 6479 |
| P283AR9P1362_B8 | 115 | 5737 | 1576 | 6.48E-04 | 12886 | 2271 |
| P283AR9P1362_C12 | 116 | 7064 | 2616 | 9.94E-05 | 14808 | 3832 |
| P283AR9P1362_C6 | 117 | 15955 | 4147 | 1.09E-03 | 17494 | 5690 |
| P283AR9P1362_C7 | 118 | 10957 | 2792 | 1.86E-04 | 19690 | 5515 |
| P283AR9P1362_D2 | 119 | 8650 | 2758 | 2.53E-04 | 17182 | 5333 |
| P283AR9P1362_D3 | 120 | 9498 | 3484 | 1.25E-04 | 34619 | 6052 |
| P283AR9P1362_D4 | 121 | 9832 | 2977 | 9.72E-05 | 25671 | 4101 |
| P283AR9P1362_D6 | 122 | 13686 | 3664 | 2.64E-05 | 33547 | 7721 |
| P283AR9P1362_D7 | 123 | 17327 | 3354 | 1.18E-04 | 27491 | 4849 |
| P283AR9P1362_E9 | 124 | 6178 | 2010 | 3.27E-04 | 15869 | 2837 |
| P283AR9P1362_F12 | 125 | 8970 | 2623 | 7.28E-05 | 26333 | 3794 |
| P283AR9P1362_F2 | 126 | 9619 | 1366 | 2.11E-03 | 26443 | 5518 |
| P283AR9P1362_F8 | 127 | 9195 | 3167 | 1.12E-04 | 23735 | 4571 |
| P283AR9P1362_G11 | 128 | 12690 | 3531 | 1.02E-04 | 32484 | 6826 |
| P283AR9P1362_G3 | 129 | 18512 | 4307 | 9.45E-05 | 35268 | 9198 |
| P283AR9P1362_H11 | 130 | 5734 | 2268 | 1.80E-04 | 11588 | 3655 |
| P283BR9P1363_A10 | 131 | 7886 | 2753 | 3.60E-04 | 27790 | 4105 |
| P283BR9P1363_A8 | 132 | 11285 | 2536 | 3.53E-04 | 24234 | 3453 |
| P283BR9P1363_B2 | 133 | 8358 | 2399 | 2.08E-04 | 14846 | 2819 |
| P283BR9P1363_B6 | 134 | 14534 | 3453 | 2.69E-04 | 37691 | 6839 |
| P283BR9P1363_C4 | 135 | 9073 | 2247 | 4.09E-04 | 23387 | 3266 |
| P283BR9P1363_C8 | 136 | 16541 | 3739 | 3.35E-04 | 37175 | 9082 |
| P283BR9P1363_D11 | 137 | 8692 | 2890 | 4.95E-04 | 20572 | 11630 |
| P283BR9P1363_E4 | 138 | 10790 | 2498 | 3.29E-04 | 17702 | 2469 |
| P283BR9P1363_E6 | 139 | 8239 | 2079 | 1.36E-03 | 16784 | 3715 |
| P283BR9P1363_F2 | 140 | 14473 | 3274 | 2.88E-04 | 33286 | 5278 |
| P283BR9P1363_F4 | 141 | 11933 | 2963 | 1.55E-04 | 20245 | 4479 |
| P283BR9P1363_F6 | 142 | 10632 | 3229 | 8.21E-05 | 31568 | 4571 |
| P283BR9P1363_G2 | 143 | 9640 | 3226 | 1.22E-04 | 15899 | 5383 |
| P283BR9P1363_G5 | 144 | 14798 | 3307 | 1.40E-04 | 24945 | 4430 |
| P283BR9P1363_G7 | 145 | 4639 | 2340 | 4.01E-05 | 7212 | 3022 |
| P283DR9P1364_A4 | 146 | 9491 | 1024 | 1.09E-03 | 48337 | 6653 |
| P283DR9P1364_A7 | 147 | 8985 | 435 | 1.97E-03 | 39870 | 2641 |
| P283DR9P1364_B1 | 148 | 1477 | 666 | 1.56E-03 | 8617 | 746 |
| P283DR9P1364_B11 | 149 | 4255 | 451 | 1.30E-03 | 22852 | 1590 |
| P283DR9P1364_B4 | 150 | 45452 | 6062 | 1.09E-04 | 96492 | 20238 |
| P283DR9P1364_C10 | 151 | 4936 | 649 | 1.29E-03 | 34234 | 2713 |
| P283DR9P1364_D11 | 152 | 32293 | 4223 | 5.14E-04 | 70431 | 16240 |
| P283DR9P1364_D8 | 153 | 656 | 244 | 6.61E-03 | 2484 | 365 |
| P283DR9P1364_D9 | 154 | 42285 | 5245 | 4.30E-04 | 88300 | 19979 |
| P283DR9P1364_E3 | 155 | 1285 | 317 | 2.53E-03 | 9128 | 887 |
| P283DR9P1364_E5 | 156 | 17625 | 1269 | 8.25E-04 | 55654 | 5091 |

TABLE 4-continued

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P283DR9P1364_E7 | 157 | 5394 | 442 | 2.43E-03 | 28732 | 2241 |
| P283DR9P1364_E8 | 158 | 14321 | 1181 | 7.56E-04 | 59328 | 5510 |
| P283DR9P1364_E9 | 159 | 4295 | 548 | 1.90E-03 | 19688 | 2096 |
| P283DR9P1364_F2 | 160 | 39164 | 6252 | 1.61E-04 | 91474 | 16946 |
| P283DR9P1364_F6 | 161 | 17215 | 1831 | 1.00E-03 | 33767 | 3161 |
| P283DR9P1364_F8 | 162 | 6305 | 458 | 1.74E-03 | 36659 | 1302 |
| P283DR9P1364_G10 | 163 | 6291 | 409 | 2.53E-03 | 10920 | 769 |
| P283DR9P1364_G9 | 164 | 9892 | 401 | 7.79E-04 | 47097 | 2796 |
| P283DR9P1364_H1 | 165 | 29248 | 3033 | 6.13E-04 | 54014 | 10610 |
| P283DR9P1364_H11 | 166 | 11479 | 834 | 9.64E-04 | 60609 | 9459 |
| P283DR9P1364_H6 | 167 | 2623 | 268 | 2.30E-03 | 6002 | 418 |
| P283DR9P1364_H9 | 168 | 32763 | 4057 | 2.71E-04 | 54593 | 4556 |
| P283ER9P1365_A1 | 169 | 25512 | 3862 | 4.67E-04 | 9676 | 1365 |
| P283ER9P1365_A7 | 170 | 18513 | 1315 | 7.86E-04 | 36568 | 2960 |
| P283ER9P1365_B6 | 171 | 22998 | 3397 | 2.88E-04 | 30081 | 2692 |
| P283ER9P1365_C1 | 172 | 8004 | 644 | 1.15E-03 | 23975 | 1884 |
| P283ER9P1365_E2 | 173 | 20011 | 2867 | 3.11E-04 | 17177 | 1905 |
| P283ER9P1365_F4 | 174 | 24065 | 2596 | 2.16E-04 | 43243 | 2038 |
| P283ER9P1365_G1 | 175 | 1280 | 318 | 3.67E-03 | 489 | 383 |
| P283ER9P1365_G3 | 176 | 12481 | 2916 | 2.50E-03 | 3480 | 1470 |
| P283ER9P1365_H3 | 177 | 17965 | 953 | 3.75E-04 | 19560 | 436 |
| P283FR9P1366_A1 | 178 | 8782 | 516 | 2.26E-03 | 39384 | 1650 |
| P283FR9P1366_A5 | 179 | 27649 | 3598 | 5.85E-04 | 67839 | 10945 |
| P283FR9P1366_A9 | 180 | 1717 | 252 | 3.94E-03 | 8809 | 580 |
| P283FR9P1366_B7 | 181 | 11365 | 899 | 1.15E-03 | 51186 | 4668 |
| P283FR9P1366_C2 | 182 | 40957 | 4319 | 4.91E-04 | 89242 | 19288 |
| P283FR9P1366_C3 | 183 | 1823 | 407 | 2.07E-03 | 4628 | 1044 |
| P283FR9P1366_C4 | 184 | 33821 | 3754 | 5.36E-04 | 63373 | 10200 |
| P283FR9P1366_C6 | 185 | 4541 | 483 | 1.43E-03 | 26242 | 1675 |
| P283FR9P1366_D12 | 186 | 27793 | 1528 | 1.76E-03 | 87643 | 8143 |
| P283FR9P1366_D6 | 187 | 32924 | 4554 | 5.09E-04 | 79621 | 10399 |
| P283FR9P1366_D7 | 188 | 7517 | 566 | 3.54E-04 | 41434 | 2581 |
| P283FR9P1366_D8 | 189 | 3394 | 413 | 1.34E-03 | 28181 | 2296 |
| P283FR9P1366_E11 | 190 | 4594 | 567 | 1.41E-03 | 14194 | 1469 |
| P283FR9P1366_F5 | 191 | 6880 | 720 | 1.04E-03 | 46414 | 4695 |
| P283FR9P1366_F8 | 192 | 3970 | 369 | 4.03E-03 | 26970 | 2269 |
| P283FR9P1366_F9 | 193 | 33559 | 6295 | 4.94E-04 | 84279 | 24622 |
| P283FR9P1366_G1 | 194 | 3605 | 650 | 8.72E-04 | 39796 | 4981 |
| P283FR9P1366_G5 | 195 | 8450 | 261 | 7.05E-04 | 36380 | 369 |
| P283FR9P1366_G8 | 196 | 6857 | 574 | 1.08E-03 | 37144 | 3126 |
| P283FR9P1366_H10 | 197 | 25020 | 2414 | 6.30E-04 | 75192 | 13854 |
| P283FR9P1366_H11 | 198 | 18896 | 2331 | 1.39E-03 | 37386 | 3659 |
| P283FR9P1366_H3 | 199 | 7671 | 632 | 1.21E-03 | 40770 | 3173 |
| P283FR9P1366_H5 | 200 | 3137 | 252 | 3.18E-03 | 5091 | 477 |
| P283FR9P1366_H6 | 201 | 43937 | 7129 | 2.05E-04 | 81542 | 18993 |
| P283FR9P1366_H7 | 202 | 13778 | 567 | 1.77E-03 | 24435 | 1238 |
| P283FR9P1366_H8 | 203 | 24942 | 4544 | 1.75E-04 | 61256 | 17144 |
| P283FR9P1366_H9 | 204 | 8570 | 693 | 1.98E-03 | 36501 | 2877 |
| P283GR7P1367_A11 | 205 | 11326 | 1029 | 6.35E-04 | 66691 | 5666 |
| P283GR7P1367_B4 | 206 | 8302 | 446 | 5.18E-03 | 396 | 367 |
| P283GR7P1367_B7 | 207 | 10865 | 739 | 1.27E-03 | 37518 | 3134 |
| P283GR7P1367_B9 | 208 | 11242 | 1092 | 1.16E-03 | 2924 | 442 |
| P283GR7P1367_C9 | 209 | 10989 | 896 | 2.21E-03 | 66977 | 5553 |
| P283GR7P1367_E5 | 210 | 10014 | 1333 | 1.24E-03 | 3189 | 533 |
| P283GR7P1367_F5 | 211 | 4565 | 601 | 1.08E-03 | 28950 | 2051 |
| P283GR7P1367_G8 | 212 | 1463 | 450 | 3.85E-03 | 21031 | 1421 |
| P283GR7P1367_H2 | 213 | 1621 | 390 | 2.35E-03 | 4207 | 864 |
| P283GR7P1367_H8 | 214 | 5269 | 303 | 9.74E-03 | 20918 | 930 |
| P283GR7P1367_H9 | 215 | 1714 | 434 | 1.47E-03 | 6121 | 918 |
| P283HR7P1368_A10 | 216 | 13632 | 3233 | 5.13E-04 | 42326 | 4772 |
| P283HR7P1368_B12 | 217 | 13399 | 1538 | 4.53E-05 | 18650 | 826 |
| P283HR7P1368_C3 | 218 | 12727 | 2215 | 3.49E-04 | 13326 | 1306 |
| P283HR7P1368_D1 | 219 | 14077 | 2312 | 1.66E-03 | 7850 | 1408 |
| P283HR7P1368_D2 | 220 | 15246 | 1907 | 1.30E-03 | 11132 | 950 |
| P283HR7P1368_D4 | 221 | 28979 | 6850 | 2.35E-04 | 52999 | 23549 |
| P283HR7P1368_F10 | 222 | 18836 | 2661 | 1.65E-03 | 16121 | 1019 |
| P283HR7P1368_F6 | 223 | 14325 | 3510 | 1.80E-04 | 20580 | 3541 |
| P283HR7P1368_G1 | 224 | 31276 | 4940 | 2.15E-03 | 69817 | 11559 |
| P283HR7P1368_G10 | 225 | 8122 | 753 | 1.45E-03 | 23790 | 2660 |
| P283HR7P1368_G11 | 226 | 19305 | 2647 | 3.73E-04 | 14857 | 1343 |
| P283HR7P1368_H1 | 227 | 15389 | 2460 | 5.52E-04 | 17285 | 1974 |

TABLE 4-continued

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P283HR7P1368_H8 | 228 | 22758 | 1612 | 7.63E−04 | 35932 | 4888 |
| Tencon25-His | 270 | 341 | 219 | | 337 | 336 |

Screen for Binding to T-Cells from Human and Cynomolgus Monkey Donors

Binding of the 190 ELISA hits to human and cynomologous monkey primary CD8 T cells was assessed by flow cytometry. The FN3 domain molecules were diluted to 2 µM and 0.2 µM in PBS and incubated with human or cynomologous monkey CD8+ T cells in 96-well format. After 1 hour at 4 C, the cells were washed once with PBS and then resuspended with an anti-FN3 domain antibody (PAB25) solution. Following this incubation, the cells were washed twice with PBS and a PE conjugated secondary antibody and a viability dye were added. Finally, cells were washed and resuspended in PBS for flow cytometric analysis using a BD Canto Instrument. Cells were gating on live cells and median fluorescence intensity of the bound Centyrins (PE channel) was calculated using Cytobank software. Results are summarized in Table 4.

Off-Rate Analysis of Anti-Human CD8 Alpha Centyrins

Purified anti-CD8A FN3 domains were subjected to off-rate analysis using a Proteon surface plasmon resonance instrument in order to pick clones with the slowest off-rates for further characterization. Measured off-rates ranged from 2.64E-5 to 1.07E-2 sec$^{-1}$ as shown in Table 4.

Goat anti-human Fc IgG (Jackson immunoresearch, Cat #109-005-098) was directly immobilized on a GLC sensor chip at 10 µg/ml, pH5.0 via amine coupling (pH 5.0) on all 6 ligand channels in vertical orientation on the chip with a flow rate of 30 µl/min in PBST (PBS, 0.005% Tween). The immobilized GAH-Fc IgG densities averaged about 6000 Response Units (Ru) with less than 1% variation among different channels. In house human CD8A-Fc was captured in vertical orientation at 3 different ligand densities, 10, 5, 2.5 µg/ml for 5 minutes at 30 ul/minute flowrate. All FN3 domains were normalized to a 3 µM concentration, and tested for binding in horizontal orientation. All 6 analyte channels were used for FN3 domains to maximize the screening throughput. The dissociation phase was monitored for 15 minutes at a flow rate of 100 µl/min using PBST as running buffer. Regeneration of the surface was achieved by a short pulse of 0.85% phosphoric acid (18 s contact time at 100 uL/min). Data analyses were performed using Bio-Rad ProteOn Manager software (version 3.1.0.6). Raw data were double referenced by subtraction of the interspot (empty chip surface, no protein immobilized or captured) signals to correct the non-specific binding of the FN3 domain to the pre-coated GAH-Fc IgG surface, followed by a double correction using empty channel L6 where no hCD8A-Fc was captured. The processed binding data were locally fit to a 1:1 simple Langmuir binding model to extract the koff for each FN3 domain binding to captured hCD8A-Fc.

Example 4: Engineering of Anti-CD8A FN3 Domains

A number of mutations were designed into top anti-CD8A candidates in order to eliminate post translational modification risks of oxidation (methionine, or tryptophan), deamidation (NS), isomerization (DG) and clipping (DP). Proline residues found in beta strands were also mutated as proline has a potential for destabilizing beta strands (Chiba T., et al. J Biol Chem. 2003; 278:47016-24). Only residues derived from FN3 domain library-designed positions were considered for mutation. Variant sequences were chosen to either mimic similar chemical properties of the parent molecule (example tryptophan to tyrosine) or to replace the PTM risk amino acid with an amino acid found in other CD8A FN3 domains at that position. A full list of engineered sequences is found in Table 5. The dissociation rate between each mutant and recombinant CD8 alpha was measured by surface plasmon resonance to estimate relative binding strengths.

TABLE 5

Dissociation rates of CD8A Centyrin mutants. Mutants are grouped according to the parent molecule.

| Sample | k$_d$ (1/s) | Mutations | SEQ ID NO: |
|---|---|---|---|
| P282DR9P1359_C5 | 1.47E−04 | Parent | 68 |
| CD8S402 | 4.84E−05 | D40P | 266 |
| CD8S396 | 1.52E−04 | W32Y | 260 |
| CD8S398 | 4.43E−04 | W32S | 262 |
| CD8S397 | 6.60E−04 | W32Q | 261 |
| CD8S399 | 1.34E−03 | W38Y | 263 |
| CD8S401 | 1.27E−02 | W38I | 265 |
| CD8S400 | 2.26E−02 | W38L | 264 |
| CD8S404 | 3.09E−02 | P36A | 268 |
| P282DR9P1359_F5 | 5.78E−05 | Parent | 79 |
| CD8S371 | 1.94E−04 | W48Y | 235 |
| CD8S377 | 4.00E−04 | W81E | 241 |
| CD8S374 | 4.03E−04 | W81Y | 238 |
| CD8S372 | 5.71E−04 | W48L | 236 |
| CD8S375 | 8.30E−04 | W81L | 239 |
| CD8S376 | 8.46E−04 | W81S | 240 |
| CD8S373 | 4.03E−03 | W48I | 237 |
| P282DR9P1359_G7 | 1.06E−05 | | 83 |
| CD8S379 | 4.97E−05 | D43S | 243 |
| CD8S378 | 5.80E−05 | D43E | 242 |
| CD8S388 | 7.54E−05 | N81Q | 252 |
| CD8S387 | 1.25E−04 | W83E | 251 |
| CD8S381 | 2.00E−04 | W70F | 245 |
| CD8S383 | 7.47E−04 | W74Y | 247 |
| CD8S380 | 1.21E−03 | W70Y | 244 |
| CD8S382 | 2.47E−01 | W70S | 246 |
| P282ER9P1360_C8 | 1.79E−04 | Parent | 89 |
| CD8S390 | 1.52E−04 | W68Y | 254 |
| CD8S389 | 1.84E−04 | W68F | 253 |
| CD8S391 | 3.20E−04 | W68H | 255 |
| CD8S405 | 1.14E−03 | P48T | 269 |
| P282DR9P1359_F7 | 3.39E−04 | Parent | 81 |
| CD8S403 | 1.33E−04 | P36A | 267 |
| CD8S392 | 1.55E−03 | W38Y | 256 |
| CD8S395 | 1.89E−03 | W38H | 259 |
| CD8S393 | 2.55E−03 | W38L | 257 |
| CD8S394 | 3.55E−03 | W38I | 258 |

From the data presented in Table 5, it is apparent that a number of mutations that reduce developability risks maintain dissociation rates similar to that of the parent molecule. Mutants CD8S402 (elimination of DP site), CD8S390 (elimination of Trp residue), and CD8S403 (removal of Pro from beta strand) resulted in slower dissociation rates than the parent appropriate molecule, indicative of tighter binding. A number of other mutations maintain binding similar to the parent molecule and thus might be preferred over the parent as these molecules pose less CMC related risks during development.

Example 5: Affinity Measurements of CD8A-Binding FN3 Domains

Nineteen anti-CD8A candidates were selected for full kinetic analysis of binding to recombinant human CD8 alpha. These candidates were selected from the above positive hits (Table 4) using the criteria of 1) strong relative binding to human T-cells, 2) strong relative binding to cyno T-cells, 3) minimal reduction in cell binding at 0.2 uM compared to 2 uM, 4) free of aggregates via SEC, 5) off-rates slower than 2.07E-3 sec-1, 6) sequence diversity with respect to sequence families, and 7) relative propensity for sequences with potential developability challenges (oxidation, deamidation, clipping and hydrophobicity).

Affinities of the top 19 candidates, later a repeat of the top 6 candidates, binding to hCD8A-Fc were measured on a ProteOn XPR36 instrument (Bio-Rad) using GLC sensor chips under similar conditions to those for koff screening. Goat anti-human Fc antibody was directly immobilized on the chip by standard amine coupling at 10 µg/ml, pH 5.0 on all 6 ligand channels in vertical orientation on the chip with a flow rate of 30 µl/min in PBST (PBS, 0.005% Tween), achieving an average of 6200 Rus on each ligand channel. Human CD8A-Fc was then captured at five surface densities ranging from 200 to 1200 response units, leaving the 6th channel as empty channel control for GAH-Fc IgG surface. Binding was measured by flowing five different concentrations of anti-CD8A FN3 domains (1 µM diluted in a 3-fold dilution series) as analytes simultaneously in the horizontal orientation over the captured hCD8A-Fc surfaces, with a sixth analyte channel containing only running buffer PBST. All interactions were measured at 100 uL/min flow rate with association and dissociation times being 4, 30 minutes respectively. Ligand surface regeneration was achieved by 1 short pulse of 0.85% phosphoric acid (18 s contact time at 100 uL/min). Data analyses were performed using Bio-Rad ProteOn Manager software (version 3.1.0.6). Raw data were double referenced by subtraction of the interspot (empty chip surface, no protein immobilized or captured) signals to correct the non-specific binding of the FN3 domain to the pre-coated GAH-Fc IgG surface, followed by a double referencing using the buffer blank response (to correct for any baseline drift resulting from ligand dissociation over time). It has been consistently observed in multiple analyses that the anti-CD8A FN3 domain binding data do not conform well to the 1:1 simple Langmuir binding model, implying either the reagents issues and/or the intrinsically complicated binding mechanisms that can't be accounted for using a simple 1:1 binding mode. Given that the GAH-Fc capture of hCD8A-Fc format is the least disruptive relative to other formats in introducing potential experimental artifacts (such as ligand activity loss and/or artificial eptiopes/heterogeneous ligand population due to amine coupling), it is considered that the results from the GAH-Fc capture experiments reported here represent the most reliable ProteOn SPR data, despite the non-conforming 1:1 Langmuir fits observed in many instances. A heterogeneous ligand model was chosen to fit the data assuming two different ligand species, either due to the heterogeneity in the ligand protein population or due to potential different mechanisms for each FN3 domain binding to the 2 hCD8A monomers in the Fc fusion protein. In this case, because each anti-CD8A FN3 domain would have separate affinities, the resultant sensorgram reflects the sum of two independent reactions with two sets of rate constants, which were reported for each FN3 domain binding.

TABLE 6

Summary of kinetic affinities for top six anti-CD8A FN3 domain candidates.

| Sample (SEQ ID NO:) | Lower Affinity Population | | | Higher Affinity Population | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| P282DR9P1359_F5 (79) | 3.48E+04 | 6.60E−05 | 6.6 | 3.80E+05 | 1.42E−05 | 0.04 |
| P282DR9P1359_F7 (81) | 4.03E+04 | 3.65E−04 | 12 | 4.04E+05 | 7.99E−05 | 0.5 |
| P282DR9P1359_G7 (83) | 6.84E+04 | 5.51E−05 | 2.1 | 2.76E+05 | 1.49E−05 | 0.05 |
| P282ER9P1360_C8 (89) | 3.09E+04 | 9.52E−05 | 4.1 | 2.18E+05 | 4.71E−05 | 0.2 |
| P283AR9P1362_D6 (122) | 5.62E+04 | 3.12E−05 | 0.98 | 1.55E+05 | 1.00E−06 | 0.03 |
| P282DR9P1359_C5 (68) | 1.92E+04 | 1.27E−04 | 6.5 | 3.00E+05 | 5.79E−06 | 0.02 |

Note:
Affinity, $K_D$ = kd/ka.

Example 6: Labeling of Anti-CD8A FN3 Domains with DFO and 89ZR

Anti-CD8A FN3 domains were modified to include a single cysteine residue for conjugation of maleimide containing chelators or PET labels. Synthetic plasmid DNA encoding clones P282DR9P1359_F5, P282DR9P1359_F7, P282DR9P1359_G7, P282ER9P1360_C8, P283AR9P1362_D6 and P282DR9P1359_C5 with a mutation of residue E54 to cysteine were synthesized at DNA2.0 (Table 7). E54 was chosen as the position for mutation based on earlier studies that demonstrated maintenance of binding affinity, stability, and expression levels for other FN3 domains mutated at this residue (Goldberg S. et al. Protein Engineering Design and Selection 2016 Epub ahead of print).

TABLE 7

Modified anti-CD8A FN3 domain molecules

| Original Clone | SEQID NO | Clone with E54C | SEQID No |
|---|---|---|---|
| P282DR9P1359_F5 | 79 | CD8S368 | 229 |
| P282DR9P1359_F7 | 81 | CD8S367 | 230 |
| P282DR9P1359_G7 | 83 | CD8S370 | 231 |
| P282ER9P1360_C8 | 89 | CD8S365 | 232 |
| P283AR9P1362_D6 | 122 | CD8S369 | 233 |
| P282DR9P1359_C5 | 68 | CD8S366 | 234 |

Anti-CD8A FN3 domains modified with a free cysteine were conjugated to Deferoxamine (DFO) in order to chelate radiometals. 0.5 mL of a 100-500 µM anti-CD8A FN3 domain solution was combined with 10 µL of 500 mM TCEP (Sigma, cat. #646547), gently flushed with nitrogen, and incubated for 1 hour at room temperature. 1.0 mL of saturated ammonium sulfate (4.02 M) was added to each tube to reach a final concentration of 3.2M before incubation on ice for 10 minutes and centrifugation at 16,000×g or higher to pellet the protein. The resulting pellet was resuspended and washed in 1.0 mL of 3.2 M ammonium sulfate supplemented with 100 mM sodium phosphate pH 7.2 and 1 mM EDTA before centrifuging again. After the second centrifugation step, the resulting pellet was dissolved in 100 mM sodium phosphate 7. 0, 1 mM EDTA and combined with 10 uL of 50 mM DFO solution to make a final molar ratio of 5:1 DFO to anti-CD8A. This reaction was allowed to proceed at room temperature for 30 minutes before quenching with 5.0 microliters of beta-mercaptoethanol. Excess DFO was finally removed by a variety of methods including a second round of ammonium sulfate precipitation as described above, passing through a desalting column such as Zeba 7 k column (Pierce Cat #89889), or by purification with nickle-NTA resin (Qiagen #30450). Anti-CD8A FN3domain-DFO conjugates were formulated in 1×PBS for further analysis.

Following conjugation to DFO, the binding of each anti-CD8A FN3 domain to recombinant human CD8 alpha was assessed by surface plasmon resonance as previously described. All samples retained tight binding to human CD8A following mutation of E54 to Cys and conjugation to DFO (Table 8).

TABLE 8

Binding affinity following DFO conjugation

| | Lower Affinity Population | | | Higher Affinity Population | | |
|---|---|---|---|---|---|---|
| Sample | $k_a$ (1/Ms) | $k_d$ (1/s) | $K_D$ (nM) | $k_a$ (1/Ms) | $k_d$ (1/s) | $K_D$ (nM) |
| CD8S365-DFO | 4.41E+03 | 4.29E−05 | 9.73 | 6.80E+04 | 4.18E−05 | 0.6 |
| CD8S366-DFO | 5.85E+03 | 1.06E−04 | 18.2 | 7.95E+04 | 7.01E−05 | 0.9 |
| CD8S367-DFO | 1.09E+04 | 9.75E−04 | 89.1 | 8.45E+04 | 1.31E−04 | 1.55 |
| CD8S368-DFO | 7.32E+03 | 9.98E−05 | 13.6 | 1.08E+05 | 2.53E−05 | 0.23 |
| CD8S369-DFO | 2.87E+03 | ≤1E−05 | ≤3.4 | 3.73E+04 | ≤1E−05 | ≤0.3 |
| CD8S370-DFO | 5.91E+03 | 7.65E−05 | 13 | 4.64E+04 | ≤2E−05 | ≤0.3 |

Example 7: Binding of Anti-CD8A FN3 Domains to Human and Cyno T-Cells

A full dose response binding curve was generated for the nineteen selected anti-CD8A FN3 domains. Each candidate was diluted to 20 µM in PBS followed by a 1:3 dilution series to generate either an 11-point or an 18-point dose response curve. Human or cyno CD8+ T cells were incubated with the diluted FN3 domain for 1 hour at 4° C. Cells were washed once with PBS and incubated with an anti-centyrin antibody (PAB25) for 1 hour at 4° C. The cells were washed twice with PBS, followed by incubation with a PE-secondary, anti-CD3-PacB, anti-CD4-APC, and a viability dye. Finally, cells were washed and resuspended in PBS for flow cytometric analysis using a BD Canto Instrument. CD8 T cells were defined as live CD3+CD4− cells. Median fluorescence intensity of the bound Centyrins (PE channel) and % of cells showing positive staining calculated using Cytobank software. Results were graphed using Prism and $EC_{50}$ values were calculated using the 4 parameter dose response variable slope equation.

A MesoScale Discovery-Cell Affinity Technology (MSD-CAT) based equilibrium cell-binding assay was performed to determine the affinity of the top six anti-CD8A candidates binding to primary human cytotoxic T cell surface CD8A receptors. Each anti-CD8A FN3 domain at a constant concentration of 50 µM was pre-incubated with 10 different concentrations of primary cytotoxic CD8 T cells (columns 2-11 in a row). Cell viability was checked prior to the binding measurements and a >85% viability was desired for valid analysis. Since these cells were from different donors, in case of donor-to-donor variations, only cells of the same donors were combined together. Each individual anti-CD8A FN3 domain binding was measured in replicates using cells from the same donors. Cells and FN3 domains were incubated overnight at 4° C. on a rotator to reach equilibrium. Following the incubation the cells were spun down along with cell bound anti-CD8A FN3 domains and the unbound (free) anti-CD8A FN3 domains in the supernatants is quantified using MSD assays where biotinylated recombinant hCD8A-Fc protein was captured at 0.6 ug/mL in assay buffer to streptavidin MSD plates overnight ~16 hours at 4° C. After blocking the plate, supernatant with free anti-CD8A FN3 domains was added to the plate and incubated for 1 hr, then followed by SulfoTag pAb139 (In-house) detection at 1.6 ug/ml. A buffer control without any FN3 domain and hCD8A (plate background binding control) in column 1 and FN3 domain alone control without hCD8A (100% free/unbound) in column 12 were included. Mouse Anti-hCD8A mAb (mIgG1k, BD Biosciences, cat #555364, clone RPA-T8) was included as a positive control. Tencon27 was included in the initial assay validation as a negative control and no significant binding was observed, and therefore, was not included in the later cell binding due to the cell availability. Plates were read immediately on the MSD Sector Imager 6000™ Reader for luminescence levels after adding MSD Read Buffer by diluting 1:4 of stock into H2O.

Raw MSD data were exported and analysed in Prism using a non-linear fit with variable slope function to derive the Bmax and Hillslope values. Only those with converged Bmax values and hillslope within the range of −1.5~−0.5 (ideal −1.0) will be considered for further analysis. Binding data were then normalized using the Bmax values to calculate the normalized % free FN3 domains. A surface CD8 density of 50,000 receptors per cell was used for the receptor concentration calculation. A saturation criterion of <20% free Centyrin at highest CD8 cell concentrations was required to determine the affinity using a "Solution Affinity Equation for normalized data" for a 1:1 binding model.

Anti-CD8A FN3 domains bound to primary cells with affinities ranging from 0.167 to 2.81 nM (Table 9).

TABLE 9

Summary of $EC_{50}$ values for top six anti-CD8A FN3 domain candidates.

| Clone ID (SEQ ID NO:) | EC50 Binding to Human T-cells by Flow Cytometry (nM) | EC50 Binding to cyno T-cells by Flow Cytometry (nM) | Affinity for Human T-cells by MSD-CAT (nM) |
|---|---|---|---|
| CD8S365 (232) | 556.0 | 123.6 | 0.167 |
| CD8S366 (234) | 162.7 | 69.5 | 0.123 |
| CD8S367 (230) | 194.5 | 50.8 | 0.225 |
| CD8S368 (229) | 154.7 | 70.0 | 0.459 |
| CD8S369 (233) | 124.2 | 72.3 | 2.81 |
| CD8S370 (231) | 208.7 | 67.6 | 0.869 |

Example 8: Activation of Human T-Cells

De Novo Activation

In order to determine if the anti-CD8A FN3 domains activate T cells, a flow cytometry assay was performed to monitor changes in T cell activation markers. Six anti-CD8A FN3 domains were evaluated for T-cell activation. De novo activation was assessed by incubating the FN3 domains at either 1 µM or 10 nM in duplicate with human pan-T cells in media for 4 days. Two independent donors were tested. Plate bound anti-CD3 was used a positive control at 2 doses, 0.1 ug/mL and 0.01 ug/mL. PBS was used as a negative control. Cells were then stained with a viability dye and the following panel of antibodies: CD4-FITC, CD3-PerCP-Cy5.5, CD69-PacB, CD45RA-BV605, CD25-BV650, CD127-PE, and CD137-PE-Cy7. CD8+ cells were defined as live CD3+CD4-cells and were profiled for each T-cell activation marker. Median fluorescence intensity values were calculated using FlowJo software and replicate values were averaged. Results are summarized in Table 10A (donor 022) and 10B (donor 146). For 365, 366, 367, 368, and 370, small changes in the T cell activation markers were observed in only 1 out of the 2 donors tested at the highest dose level of 1 µM. These changes were absent in both donors at the 10 nM dose, suggesting the molecules do not activate T cells de novo at relevant concentrations. The 369 molecule does appear to significantly activate CD137 expression in both donors at the highest dose level.

TABLE 10

Median Fluorescence Intensity (MFI) values for various T cells activation markers on CD8+ T cells for Donor 022 (A) and Donor 146 (B)

A

| Donor | Sample (SEQ ID NO:) | Anti-CD8A FN3 conc μM | Anti-CD3 ug/mL | CD45RA MFI | CD25 MFI | CD69 MFI | CD127 MFI | CD137 MFI |
|---|---|---|---|---|---|---|---|---|
| 022 | PBS control | 0 | 0 | 12856 | 571 | 223 | 651 | 296 |
| 022 | PBS control | 0 | 0.01 | 13133 | 707 | 403 | 517 | 343 |
| 022 | PBS control | 0 | 0.1 | 11394 | 1333 | 1694 | 158 | 529 |
| 022 | CD8S366 (234) | 1 | 0 | 15054 | 949 | 477 | 425 | 310 |
| 022 | CD8S366 (234) | 0.01 | 0 | 13336 | 814 | 230 | 586 | 301 |
| 022 | CD8S368 (229) | 1 | 0 | 12992 | 858 | 698 | 367 | 329 |
| 022 | CD8S368 (229) | 0.01 | 0 | 15262 | 677 | 276 | 489 | 306 |
| 022 | CD8S367 (230) | 1 | 0 | 15409 | 796 | 401 | 511 | 297 |
| 022 | CD8S367 (230) | 0.01 | 0 | 13666 | 723 | 261 | 502 | 312 |
| 022 | CD8S370 (231) | 1 | 0 | 12946 | 916 | 572 | 376 | 353 |
| 022 | CD8S370 (231) | 0.01 | 0 | 14973 | 776 | 353 | 435 | 331 |
| 022 | CD8S365 (232) | 1 | 0 | 13935 | 904 | 562 | 367 | 328 |
| 022 | CD8S365 (232) | 0.01 | 0 | 15156 | 697 | 243 | 504 | 323 |
| 022 | CD8S369 (233) | 1 | 0 | 13661 | 783 | 440 | 441 | 5122 |
| 022 | CD8S369 (233) | 0.01 | 0 | 16513 | 717 | 251 | 596 | 416 |
| 022 | TenCon | 1 | 0 | 14920 | 702 | 284 | 447 | 334 |

B

| Donor | Sample (SEQ ID NO:) | Anti-CD8A FN3 conc μM | Anti-CD3 μg/mL | CD45RA MFI | CD25 MFI | CD69 MFI | CD127 MFI | CD137 MFI |
|---|---|---|---|---|---|---|---|---|
| 146 | PBS | 0 | 0 | 7172 | 627 | 61 | 1313 | 500 |
| 146 | PBS | 0 | 0.01 | 8076 | 681 | 153 | 1296 | 617 |
| 146 | PBS | 0 | 0.1 | 5171 | 1462 | 1100 | 139 | 798 |
| 146 | CD8S366 (234) | 1 | 0 | 8531 | 673 | 95 | 1368 | 589 |
| 146 | CD8S366 (234) | 0.01 | 0 | 9414 | 623 | 74 | 1615 | 559 |
| 146 | CD8S368 (229) | 1 | 0 | 8386 | 691 | 96 | 1301 | 561 |
| 146 | CD8S368 (229) | 0.01 | 0 | 9147 | 628 | 82 | 1424 | 586 |
| 146 | CD8S367 (230) | 1 | 0 | 8167 | 660 | 95 | 1322 | 581 |
| 146 | CD8S367 (230) | 0.01 | 0 | 8734 | 586 | 77 | 1479 | 571 |
| 146 | CD8S370 (231) | 1 | 0 | 8590 | 737 | 86 | 1362 | 583 |
| 146 | CD8S370 (231) | 0.01 | 0 | 7934 | 635 | 71 | 1526 | 559 |
| 146 | CD8S365 (232) | 1 | 0 | 8344 | 813 | 85 | 1238 | 586 |
| 146 | CD8S365 (232) | 0.01 | 0 | 8460 | 628 | 80 | 1355 | 605 |
| 146 | CD8S369 (233) | 1 | 0 | 8778 | 681 | 92 | 1369 | 5690 |
| 146 | CD8S369 (233) | 0.01 | 0 | 7862 | 591 | 74 | 1498 | 784 |
| 146 | TenCon | 1 | 0 | 7325 | 609 | 78 | 1198 | 574 |
| 146 | TenCon | 0.01 | 0 | 7764 | 596 | 66 | 1281 | 530 |

Pan T-Cell Activation

In order to determine if the anti-CD8A FN3domains can affect markers of cell activation in pan-activated cells, the anti-CD8A FN3 domains were also evaluated in combination with a low dose of plate bound CD3. In this assay, a sub-optimal concentration (0.01 μg/mL) of plate bound anti-CD3 was used to activate the T cells in the presence of either 1 μM or 10 nM anti-CD8A. After 4 days, the cells were assessed using the same panel and gating strategy as described above. Two independent donors were tested. Median fluorescence intensity values were calculated using FowJo software and replicate values were averaged. Results are summarized in Tables 11A (donor 022) and 11B (donor 146).

TABLES 11A and 11B

Median Fluorescence Intensity (MFI) values for various T cells activation markers on CD8+ T cells for Donor 022 (A) and Donor 146 (B) in the presence of plate bound CD3.

A

| Donor | Sample (SEQ ID NO:) | Anti-CD8A FN3 conc μM | Anti-CD3 μg/mL | CD45RA MFI | CD25 MFI | CD69 MFI | CD127 MFI | CD137 MFI |
|---|---|---|---|---|---|---|---|---|
| 022 | PBS control | 0 | 0 | 12856 | 571 | 223 | 651 | 296 |
| 022 | PBS control | 0 | 0.01 | 13133 | 707 | 403 | 517 | 343 |
| 022 | PBS control | 0 | 0.1 | 11394 | 1333 | 1694 | 158 | 529 |
| 022 | CD8S366 (234) | 1 | 0.01 | 11918 | 892 | 1005 | 369 | 376 |
| 022 | CD8S366 (234) | 0.01 | 0.01 | 13417 | 1068 | 848 | 384 | 399 |
| 022 | CD8S368 (229) | 1 | 0.01 | 11311 | 1147 | 1279 | 260 | 428 |
| 022 | CD8S368 (229) | 0.01 | 0.01 | 13441 | 760 | 599 | 499 | 348 |
| 022 | CD8S367 (230) | 1 | 0.01 | 13271 | 1135 | 1127 | 367 | 385 |
| 022 | CD8S367 (230) | 0.01 | 0.01 | 14521 | 960 | 636 | 483 | 362 |
| 022 | CD8S370 (231) | 1 | 0.01 | 15138 | 1103 | 890 | 407 | 378 |
| 022 | CD8S370 (231) | 0.01 | 0.01 | 14230 | 875 | 612 | 431 | 355 |
| 022 | CD8S365 (232) | 1 | 0.01 | 14395 | 1112 | 907 | 380 | 407 |
| 022 | CD8S365 (232) | 0.01 | 0.01 | 14006 | 1175 | 1063 | 297 | 430 |
| 022 | CD8S369 (233) | 1 | 0.01 | 13735 | 877 | 759 | 464 | 5457 |
| 022 | CD8S369 (233) | 0.01 | 0.01 | 13864 | 842 | 617 | 450 | 498 |
| 022 | TenCon | 1 | 0.01 | 14687 | 791 | 553 | 408 | 358 |
| 022 | TenCon | 0.01 | 0.01 | 13090 | 759 | 630 | 464 | 368 |

B

| Donor | Sample (SEQ ID NO:) | Anti-CD8A FN3 conc μM | Anti-CD3, μg/mL | CD45RA MFI | CD25 MFI | CD69 MFI | CD127 MFI | CD137 MFI |
|---|---|---|---|---|---|---|---|---|
| 146 | PBS control | 0 | 0 | 12856 | 571 | 223 | 651 | 296 |
| 146 | PBS control | 0 | 0.01 | 13133 | 707 | 403 | 517 | 343 |
| 146 | PBS control | 0 | 0.1 | 11394 | 1333 | 1694 | 158 | 529 |
| 146 | CD8S366 (234) | 1 | 0.01 | 6798 | 876 | 163 | 1095 | 632 |
| 146 | CD8S366 (234) | 0.01 | 0.01 | 8589 | 775 | 158 | 1077 | 637 |
| 146 | CD8S368 (229) | 1 | 0.01 | 6576 | 945 | 175 | 1105 | 662 |
| 146 | CD8S368 (229) | 0.01 | 0.01 | 7608 | 843 | 200 | 950 | 678 |
| 146 | CD8S367 (230) | 1 | 0.01 | 6447 | 897 | 173 | 1088 | 672 |
| 146 | CD8S367 (230) | 0.01 | 0.01 | 7899 | 801 | 175 | 1031 | 655 |
| 146 | CD8S370 (231) | 1 | 0.01 | 7327 | 992 | 169 | 1055 | 687 |

TABLES 11A and 11B-continued

Median Fluorescence Intensity (MFI) values for various T cells activation markers on CD8+ T cells for Donor 022 (A) and Donor 146 (B) in the presence of plate bound CD3.

| 146 | CD8S370 (231) | 0.01 | 0.01 | 8676 | 790 | 183 | 946 | 675 |
|---|---|---|---|---|---|---|---|---|
| 146 | CD8S365 (232) | 1 | 0.01 | 6624 | 977 | 172 | 1059 | 670 |
| 146 | CD8S365 (232) | 0.01 | 0.01 | 7902 | 843 | 193 | 985 | 659 |
| 146 | CD8S369 (233) | 1 | 0.01 | 7660 | 933 | 165 | 1149 | 7114 |
| 146 | CD8S369 (233) | 0.01 | 0.01 | 7892 | 854 | 187 | 989 | 842 |
| 146 | TenCon | 1 | 0.01 | 8352 | 829 | 170 | 1026 | 658 |
| 146 | TenCon | 0.01 | 0.01 | 7627 | 761 | 185 | 1043 | 673 |

Cytokine Response

Figure 1B:
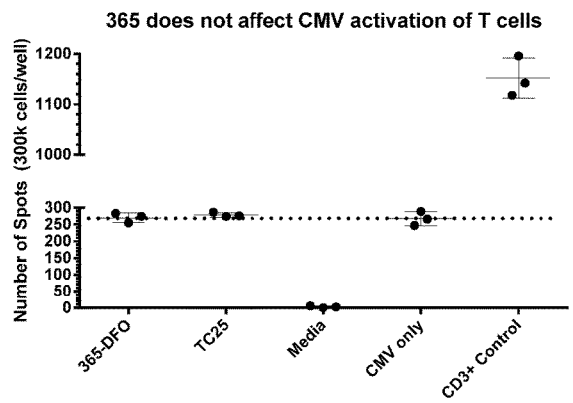
Figure 1C:
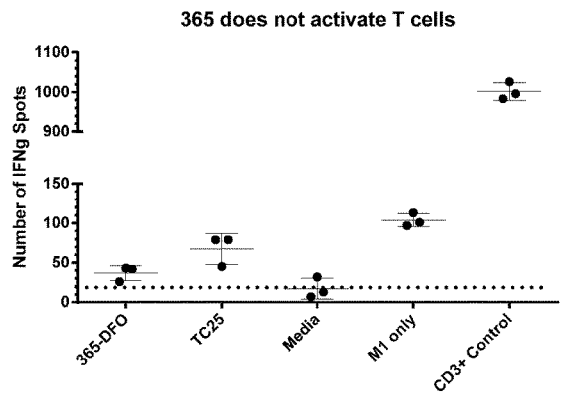
Figure 1D:
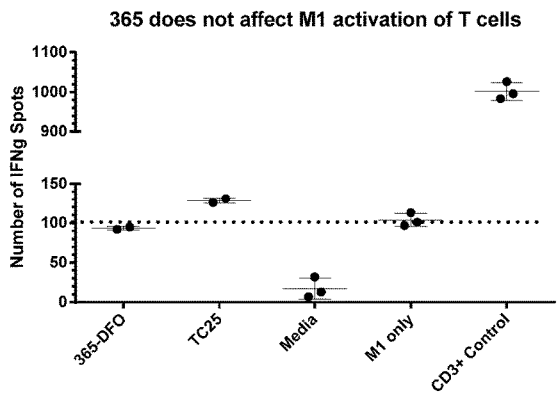

In order to determine if any of the changes observed in the activation markers resulting in changes in cytokine production, antigen-dependent T cell activation assays were also performed using two anti-CD8A FN3 domains. For one set of assays, either CMV reactive or M1 reactive human PBMCs were thawed and rested overnight at 37° C. in 6 well plates. The following day, the PBMCs were harvested by pipetting, counted, and plated onto IFNg Mabtech ELISpot plates in the presence or absence of 10 μg/mL peptide. 1 μM anti-CD8A FN3-DFO conjugate was added to the wells and plates were allowed to incubate at 37° C. for approximately 24 hours undisturbed. The cells were removed and the plates were washed 5 times with PBS. The supplied detection antibody was added and plates were incubated for 2 hours. The plates were again washed and the kit substrate was added to each well. Plates were developed for approximately 5 minutes before the reaction was stopped by running the plate under water. Plates were dried upside down overnight in the dark. Plates were read on the AID EliSpot Reader and spot counts were generated using the AID EliSpot Software. Results were graphed in Prism. Results are summarized in FIG. 1. In this assay, 365-DFO does not increase the number of IFNg spots compared to media alone or non-CD8A binding TenCon control in the absence of peptide (FIG. 1A, 1C). Peptide and CD3 are included as positive controls. In the presence of peptide, the 365-DFO does not change the number of IFNg spots compared to peptide alone or peptide with non-CD8A binding tencon (FIG. 1B, 1D). Media is included as a negative control and CD3 is included as a positive control. These results suggest that the centyrin does not affect T cell activation.

Figure 2A:
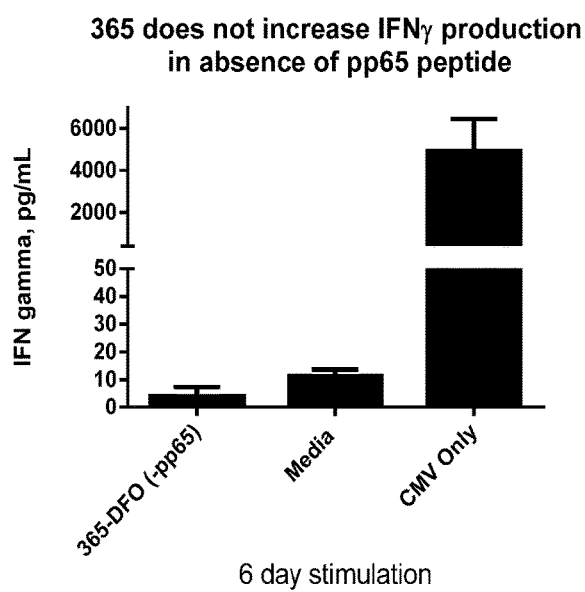
FIGS. 2A and 2B. The CD8S365-DFO conjugate does not activate T cells de novo and does not modulate the antigen dependent activation of T cells in a 6 day INF$^\gamma$ MSD assay. CMV reactive T cells were treated with 365-DFO in the absence (A) or presence (B) of CMV peptides.
Figure 2B:
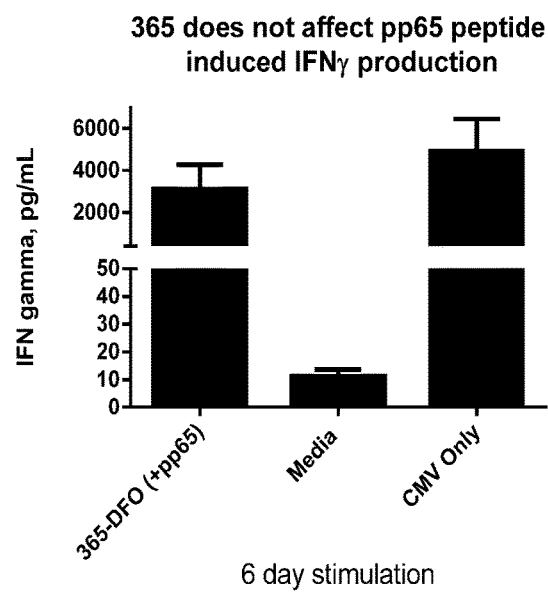

To confirm these results in a longer-term assay, IFN-gamma levels were also measured in a 6-Day activation assay. For this study, CMV reactive PBMCs were incubated in triplicate with anti-CD8A FN3 domains at 1 uM in the presence or absence of 0.25 μg/mL pp65 peptide. Cells were incubated for 6 days at 37 C. At each timepoint the cells were centrifuged and supernatant was harvested. Samples were stored at −80° C. until analyzed. Thawed samples were analyzed for IFN-gamma using a single-plex Meso Scale Discovery (MSD) based ELISA. For this assay, a standard curve was prepared as per manufacturer's instructions. Samples and standards were added to pre-coated 96 well MSD plates. After a 2 hour incubation, the kit detection antibody was added. After another 2 hour incubation, plates were washed three times followed by the addition of the supplied read buffer. Plates were read on MSD Sector Imager 6000 plate reader. Raw MSD data files were analyzed against the standard curves generated using the MSD Discovery Workbench software. The analyzed data graphed using the Tibco Spotfire program. Results are summarized in FIG. 2. In this assay, 365-DFO does not increase the secretion of IFNg into the media compared to media alone in the absence of peptide (FIG. 2A). CMV peptide is included as a positive control. In the presence of peptide, the 365-DFO also does not change the amount of IFNg secretion compared to peptide alone (FIG. 2B). Media is included as a negative control. These results suggest that the centyrin does not affect T cell activation.

Example 9: Labeling of Anti-CD8A FN3 Domains with I124/I125

The current method to radiolabel CD8S365 with iodine-124 to produce [$^{124}$I]-IPEM CD8S 365 (Scheme 1) was adapted from literature procedures (*Bioconjugate Chem.* 1991, 2, 435-440; *ChemistryOpen* 2015, 4, 174-182).

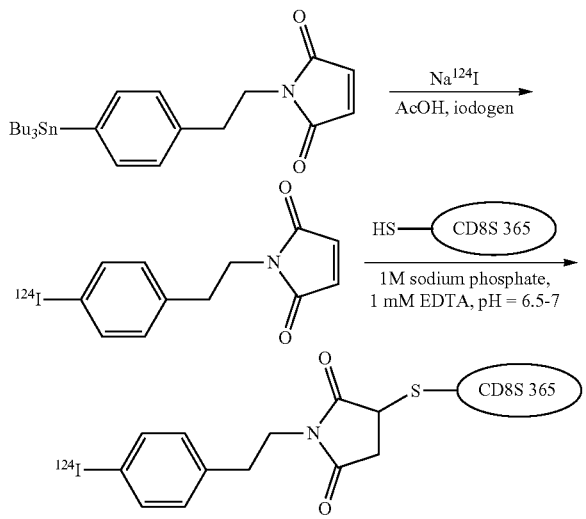

Scheme 1: Synthesis of [$^{124}$I]-IPEM CD8S 365

To a 1.5 mL Eppendorf vial was added, in order, Na$^{124}$I solution (≤13 μL, ≤2.5 mCi), AcOH (5 μL to acidify the solution), 1-(4-(tributylstannyl)phenethyl)-1H-pyrrole-2,5-dione (75 μL, 1.00 mg/mL in MCCN) and iodogen (5 μL, 1.00 mg/mL in MeCN) solution. The reaction was left for 5 min at room temperature.

Figure 3:
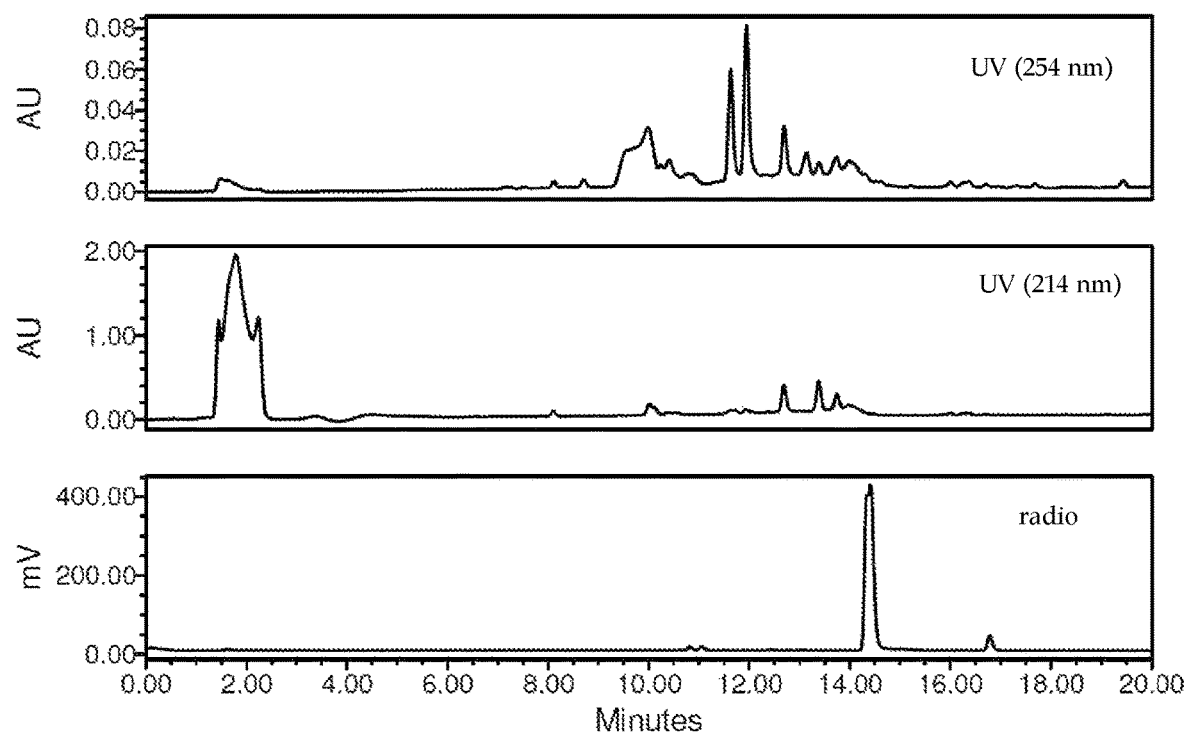
FIG. 3. Crude preparatory HPLC trace of [$^{124}$I]-IPEM. Preparatory HPLC was performed using a Waters 1525 Binary HPLC pump, a Waters 2489 dual wavelength UV/Visible Detector ($\lambda$=214 and 254 nm), a Bioscan Flow Count radiodetector (B-FC-2000) and a Atlantis T3, 100 Å, 5 µm, 150×4.6 mm HPLC column. The elution profile used was as follows: solvent A=H$_2$O (0.1% AcOH (v/v)), Solvent B=MeCN (0.1% AcOH (v/v)), flow rate=1.5 mLmin$^{-1}$; initial=80% A, 20 min=0% A (linear gradient). Multiple small molecule absorbance on UV-vis traces at 254 nm (top graph) and 214 nm (middle graph) indicate presence of impurities and by-products in the crude reaction mixture. Radiotrace (bottom graph) also shows expected baseline peaks due to radiolabeled impurities.

The crude reaction mixture was diluted with 0.5 mL of 20% EtOH/H$_2$O and was purified directly on preparatory HPLC, the retention time=14.4 min (FIG. 3). The [$^{124}$I]-IPEM was collected in a 1 dram vial that had been pre-treated with Sigma-Cote™ (then rinsed with 3 mL of 70% EtOH, followed by 3 mL of H$_2$O); total volume collected off preparatory HPLC <750 μL.

Figure 4:
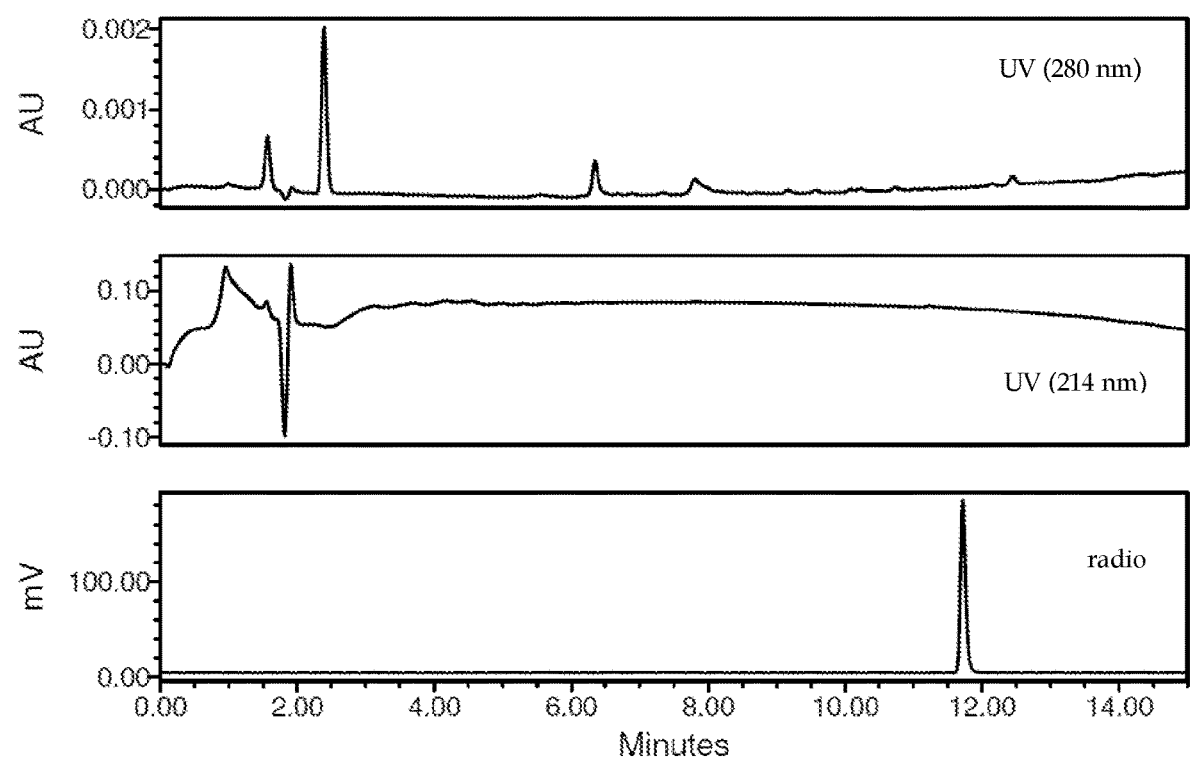
FIG. 4. Analytical HPLC trace of [$^{124}$I]-IPEM. Analytical HPLC was performed using a Waters 1525 Binary HPLC pump, a Waters 2707 autosampler, a Waters 2489 dual wavelength UV/Visible Detector ($\lambda$=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H$_2$O (0.1% TFA (v/v)), Solvent B=MCCN (0.1% TFA (v/v)), flow rate=1 mLmin$^{-1}$; initial=90% A, 15 min=0% A (linear gradient). Analytically pure [I-124] IPEM shows a single radiopeak (bottom graph) with a smooth baseline confirming successful purification. Please note that [I-124] IPEM is an organic small molecule; hence, lacking absorption at 280 nm (top graph) and 214 nm (middle graph).

An aliquot (~5-25 μCi) of the purified fraction was then injected on analytical HPLC (FIG. 4, retention time=11.7 min).

The purified [$^{124}$I]-IPEM was then concentrated under vacuum at ambient temperature to a volume of <100 μL.

Sodium phosphate buffer (1.0 M sodium phosphate, 1 mM EDTA, pH=6.86) was added (≥25 μL) to bring the pH to ~6.5-7 (checked by strip). Lastly freshly reduced CD8S 365 (c ~4.57 mg/mL in 100 mM sodium phosphate buffer, 1 mM EDTA, pH=6.86), was added in appropriate amount to achieve targeted specific activity (ie. if targeting specific activity of 25 mCi/mg and 2.0 mCi of [$^{124}$I]-IPEM was collected add 17.5 μL of centyrin at c ~4.57 mg/mL). The conjugation reaction was left for 60 min at ambient temperature and the reaction progress was checked to verify that the conversion exceeded 90% by iTLC.

Figure 5:
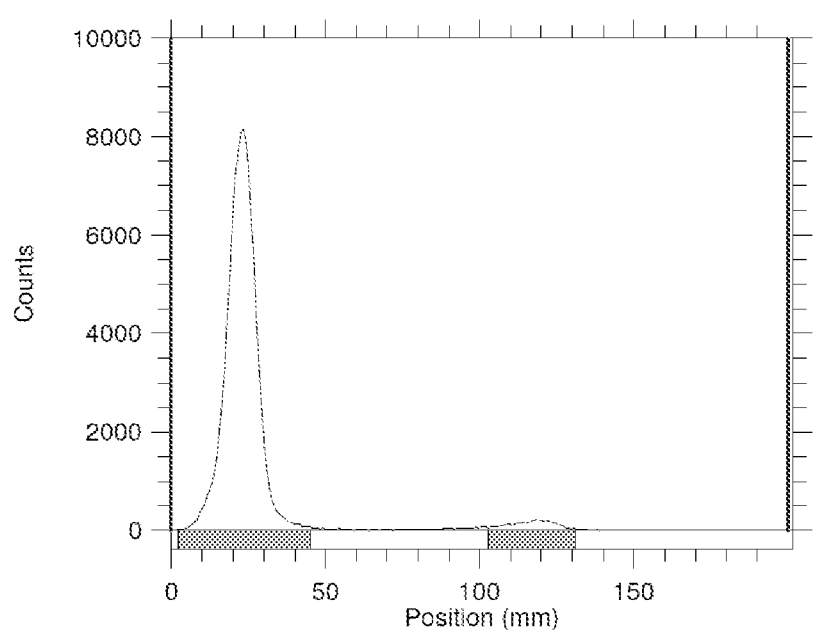
FIG. 5. Radio TLC of purified [$^{124}$I]-IPEM CD8S365. The iTLC-SG plate (Agilent, cat #SGI0001) was read on a Bioscan AR-2000 radio-TLC imaging scanner. The radio TLC plate (FIG. 3) was co-spotted with 1 µL of NaI (0.1 M) and developed using citric acid (0.5 mM, pH=5) as eluent. The origin=20 mm and the solvent front=100 mm. The radio TLC eluent was prepared by dissolving 96 mg of citric acid (Spectrum cat #CI131) in 25 mL of Trace Select H$_2$O and then Na$_2$CO$_3$ was added (245 µL, 2 M); the pH was checked by strip (pH=5).

Purification consisted of diluting the reaction solution with PBS/10% EtOH (1 mL, pH=7) transferring the reaction solution from the 1 dram vial into a Vivaspin 6 5 kDa MWCO centrifugal filter (see appendix for the pre-conditioning). After the transfer, the reaction Eppendorf was rinsed with PBS/10% EtOH (2×1 mL, pH=7) and the washings were added to the filter. The crude reaction mixture was centrifuged at 4000 rpm, at 20° C. for 30 min. Following centrifugation <500 μL of solution remained and was found to have a radiochemical purity (RCP) >95% by radio TLC (FIG. 5). The purified [$^{124}$I]-IPEM CD8S 365 was diluted to a volume of 500 μL with PBS/10% EtOH if the volume was <500 μL and then filtered through a Millex-GV 0.22 μm hydrophilic Duropore (PVDF) membrane.

Figure 6:
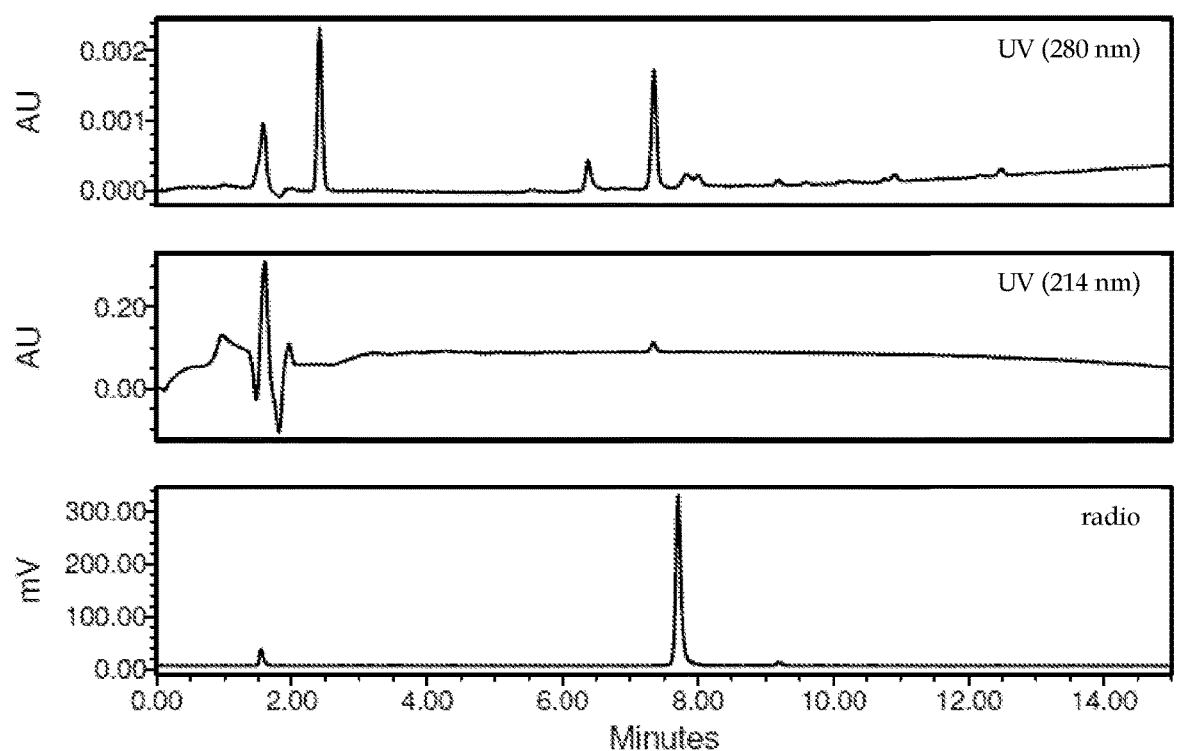
FIG. 6. Analytical HPLC trace of purified [$^{124}$I]-IPEM CD8S 365. Analytical HPLC was performed using a Waters 1525 Binary HPLC pump, a Waters 2707 autosampler, a Waters 2489 dual wavelength UV/Visible Detector ($\lambda$=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H$_2$O (0.1% TFA (v/v)), Solvent B=MCCN (0.1% TFA (v/v)), flow rate=1 mLmin$^{-1}$; initial=90% A, 15 min=0% A (linear gradient). Biomolecule (CD8S) absorbance at 280 nm (top graph) and small molecule (I124-IPEM) absorbance at 214 nm (middle graph) confirms successful conjugation reaction. UV and radio traces (bottom graph) indicate an analytically pure sample.
Figure 7:
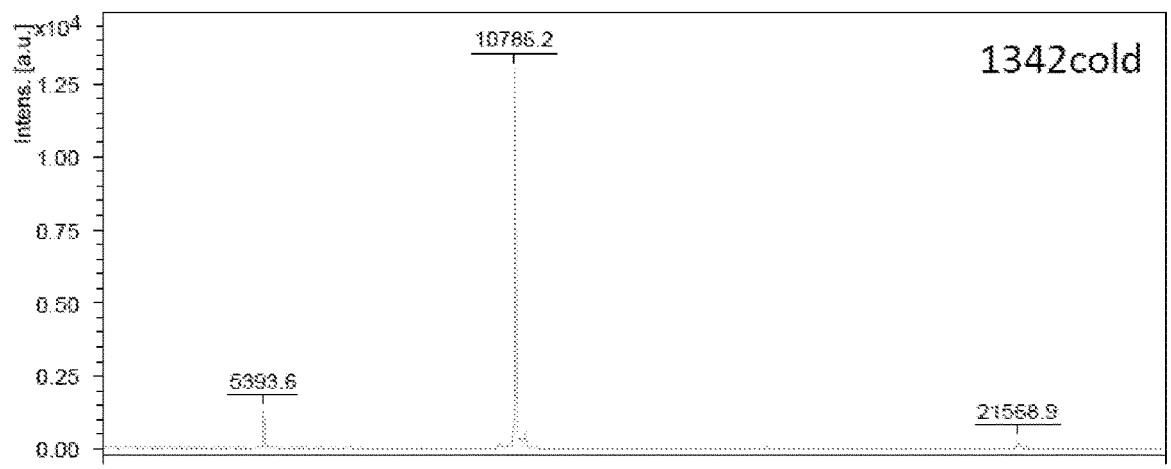
FIG. 7. MALDI-MS of IPEM CD8S365 (theoretical MW=10786.12). The MALDI-MS analysis was performed at the Biointerfaces Institute using a Bruker UltrafleXtreme MALDI TOF/TOF in positive ion mode (linear detector). A saturated solution of sinapinic acid was prepared in TA30 solvent (30:70 (v/v) MeCN:0.1% TFA in water). The sample (c=0.397 mgmL$^{-1}$) was mixed in a 1:1 ratio with the matrix solution and 1 L was spotted on the plate. A protein solution was used as an external standard.
Figure 8:
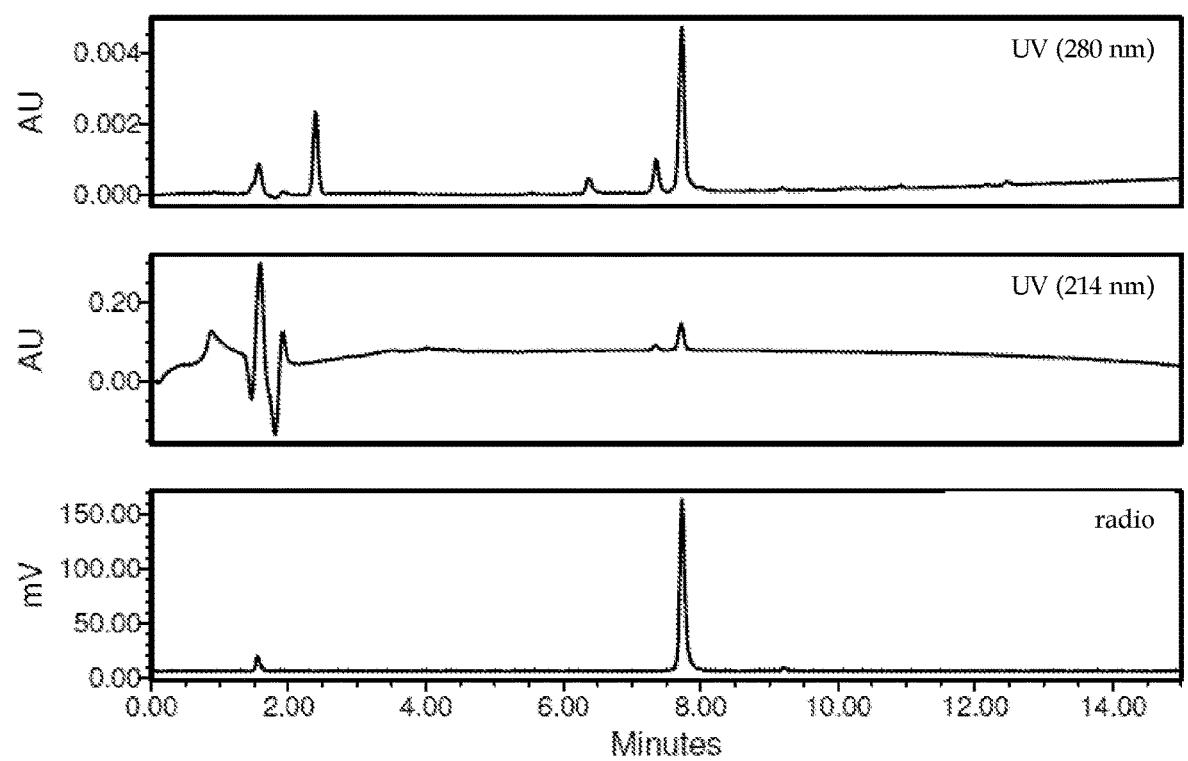
FIG. 8. Co-injection of [$^{124}$I]-IPEM CD8S365 with cold standard. Analytical HPLC was performed using a Waters 1525 Binary HPLC pump, a Waters 2707 autosampler, a Waters 2489 dual wavelength UV/Visible Detector ($\lambda$=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H$_2$O (0.1% TFA (v/v)), Solvent B=MCCN (0.1% TFA (v/v)), flow rate=1 mLmin$^{-1}$; initial=90% A, 15 min=0% A (linear gradient). Co-injection with cold sample leads to complete overlap of UV peaks (top and middle graphs), confirming the product's molecular identity (i.e. Cold and radiolabeled conjugates are identical except for the replacement of Iodine by Iodine-124)

The radiochemical yield from the protocol is ~50% with a radiochemical purity ≥95% RCP by radio TLC). Analytical reverse phase HPLC was used to determine the protein concentration and specific activity of the final product. The average integration of the peak at retention time=7.3 min in the UV at λ=280 nm was used to extrapolate the protein concentration from a calibration curve (FIG. 6 for a representative example). A co-injection with the non-radioactive cold standard IPEM CD8S 365 (MALDI analysis shown in FIG. 7) was also conducted (see FIG. 8). The bacterial endotoxin concentration was measured using the Endosafe® portable test system using a 10× dilution with LAL reagent water.

Example 10: Detection of CD8 Expression in Cynomolgus Monkeys

Two anti-CD8A FN3 molecules (CD8S365 and CD8S368) were selected for PET imaging in non-human primates (NHP). The anti-CD8A molecules were radiolabeled with either Zr-89 (Zevacor, Somerset, N.J.) or I-124 (CPDC, Hamilton, Canada, and Zevacor, Somerset, N.J.). Approximately 1-2 mCi of radiolabeled anti-CD8A molecules was(were) injected into the saphenous vein of a female NHP (cynomolgus macaque), while anesthetized with isoflurane in oxygen. Each animal was scanned in a large-bore microPET Focus 220 PET scanner (Siemens, Knoxville, Tenn.), with the bed moved to accommodate the entire body of the animal (head to lower abdomen). Each scan lasted approximately 1 h, and scans were acquired at 15 min, 2 h, and 24 h after injection. PET images were reconstructed using a 2D maximum likelihood expectation maximization (ML-EM) algorithm, into 3D images of voxel size 1.898×1.898×0.796 mm, dimensions 128×128×475. Blood samples were obtained at multiple time points from the saphenous vein in the opposite leg to the injection, and the blood radioactivity counted in a well counter.

Figure 9:
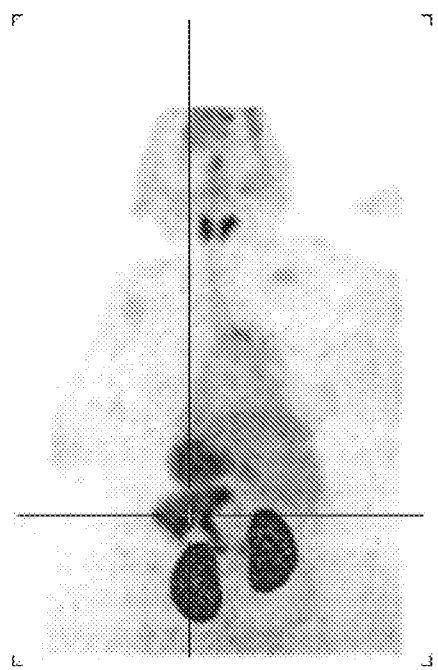
FIG. 9. Representative PET image showing CD8S365-IPEM5 radiolabeled with I-124, taken at 2 h post-injection. The image is a maximum intensity projection (anterior-posterior), with the spleen centered on the cross-hairs. The organs below the spleen are the kidneys, and the image is oriented to show the head at the top. The uptake in the thyroid is evidence of some de-iodination of the protein.

PET images were analyzed using PMOD v3.7 software (PMOD, Zurich, Switzerland). Regions-of-interest were drawn manually around organs such as spleen, kidneys and liver. Counts were converted to units of percent injected dose per gram of tissue (% ID/g), while blood radioactivity was presented as % ID. A representative PET image is shown in FIG. 9.

Figure 10:
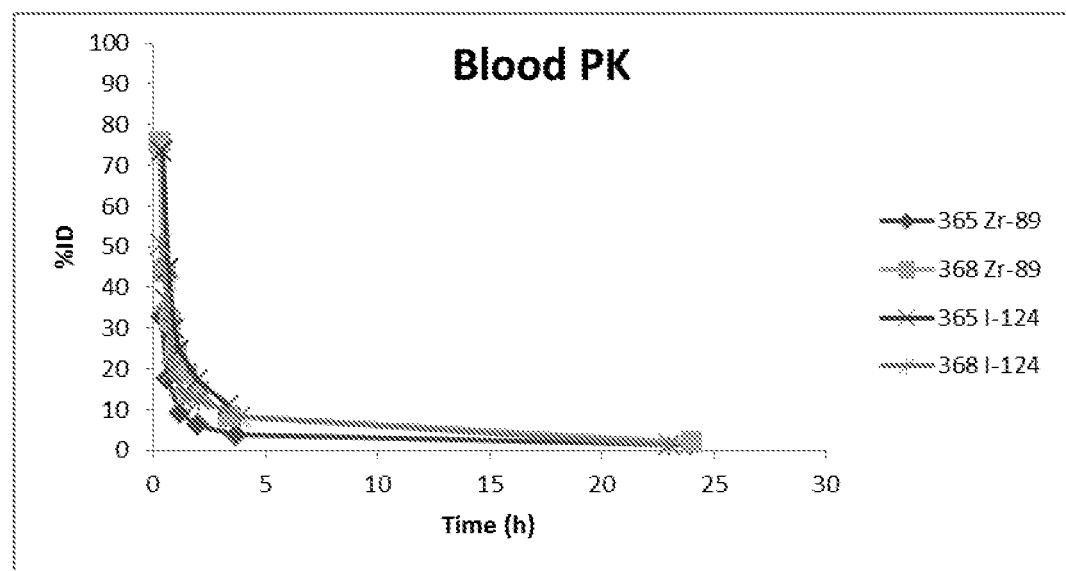
FIG. 10. Time-activity curves for blood radioactivity in non-human primate for each anti-CD8A FN3 domain labeled with either Zr-89 or I-124.

Blood kinetics for each NHP and each anti-CD8A FN3 domain molecule (labeled with either Zr-89 or I-124) are shown in Table 11, and summarized in FIG. 10. For the same animals and anti-CD8A molecules, the organ biodistributions are shown in Table 12 (units are % ID/g), and summarized in FIG. 11. The Zr-89 labeled molecules exhibited residualization of the radioisotope in the excretory organs, which caused a large background signal in the kidneys, potentially obscuring other nearby tissues. This was largely absent from the I-124 labeled molecules. The spleen uptake was very similar between the two different molecules and two different radioisotopes for all time points.

TABLE 11

Blood kinetics for each centyrin, radiolabeled with either Zr-89 or I-124 (entries are % ID).

| Time (h) | 365 Zr-89 | Time (h) | 368 Zr-89 | Time (h) | 365 I-124 | Time (h) | 368 I-124 |
|---|---|---|---|---|---|---|---|
| 0.38 | 32.49 | 0.25 | 75.64 | 0.40 | 73.53 | 0.33 | 50.56 |
| 0.62 | 17.62 | 0.50 | 44.01 | 0.65 | 44.59 | 0.57 | 37.07 |
| 1.18 | 9.03 | 0.75 | 32.06 | 0.92 | 29.79 | 0.87 | 19.33 |
| 2.00 | 6.12 | 1.00 | 24.20 | 1.13 | 24.51 | 1.17 | 16.01 |
| 3.70 | 3.77 | 1.50 | 18.82 | 2.00 | 17.14 | 1.37 | 12.84 |
| 24.00 | 1.36 | 2.00 | 14.22 | 3.33 | 10.92 | 2.07 | 12.18 |
| | | 3.33 | 8.40 | | | 3.88 | 8.20 |
| | | 24.00 | 1.94 | | | 23.03 | 1.24 |

Figure 11A:
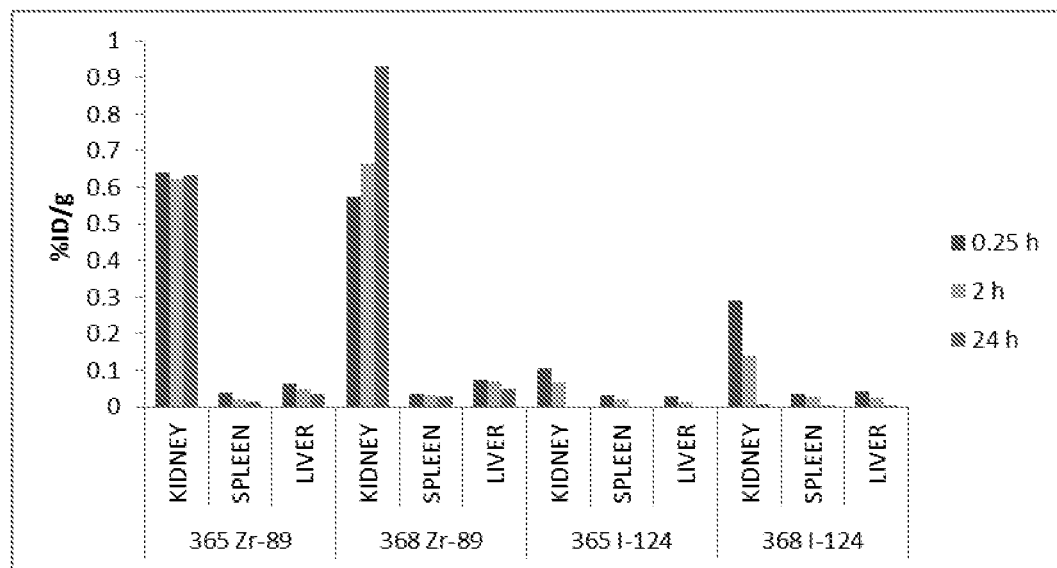
FIGS. 11A and 11B. Time-activity curves for organ radioactivity in NHP for each centyrin labeled with either Zr-89 or I-124.
Figure 11B:
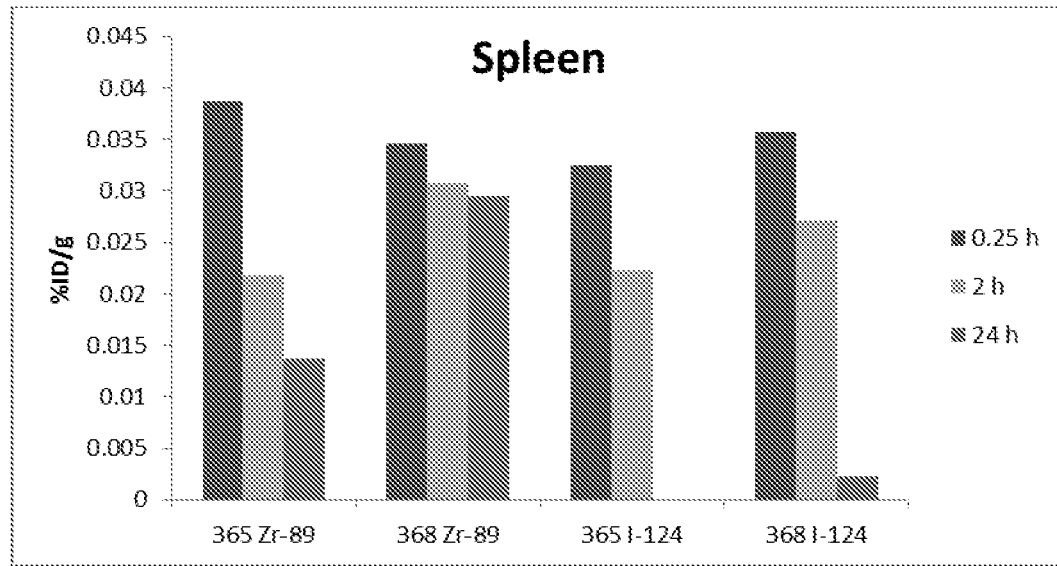

For the same animals and anti-CD8A molecules, the organ biodistributions are shown in Table 12 (units are % ID/g), and summarized in FIG. 11.

TABLE 12

Organ uptake for the different centyrins, labeled with either Zr-89 or I-124 (entries are % ID/g).

| Time (h) | Kidney | Spleen | Liver |
|---|---|---|---|
| 365 Zr-89 | | | |
| 0.25 h | 0.641 | 0.0386 | 0.0620 |
| 2 h | 0.624 | 0.0218 | 0.0513 |
| 24 h | 0.633 | 0.0136 | 0.0354 |
| 368 Zr-89 | | | |
| 0.25 h | 0.575 | 0.0345 | 0.0740 |
| 2 h | 0.664 | 0.0307 | 0.0688 |
| 24 h | 0.931 | 0.0294 | 0.0508 |
| 365 I-124 | | | |
| 0.25 h | 0.104 | 0.0324 | 0.0291 |
| 2 h | 0.065 | 0.0222 | 0.0142 |
| 24 h | Not collected due to technical issue | | |
| 368 I-124 | | | |
| 0.25 h | 0.292 | 0.0357 | 0.0439 |
| 2 h | 0.140 | 0.0271 | 0.0241 |
| 24 h | 0.0089 | 0.0022 | 0.0029 |

Example 11: Specificity of Anti-CD8A FN3 Domains in Cynomolgus Monkeys

Figure 12A:
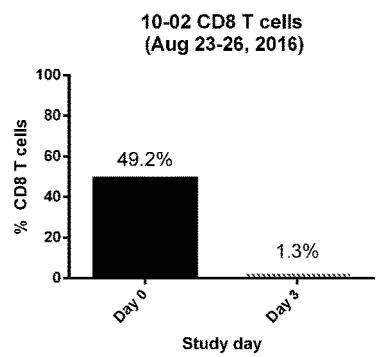
FIG. 12A-12C. Confirmation of CD8 T cell depletion by Day 3 in blood taken from a non-human primate (12A). Also shown are changes in CD4 (12B) and CD3 T cells (12C).
Figure 12B:
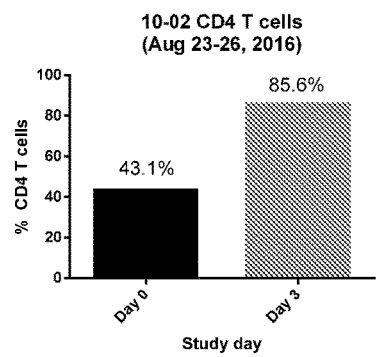
Figure 12C:
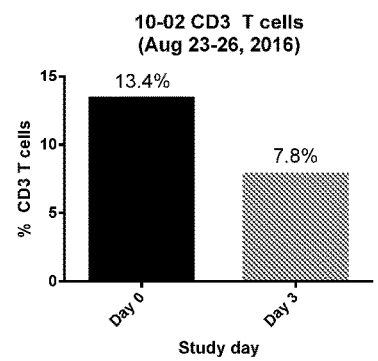

In order to test specificity of the anti-CD8A molecules, the same monkeys were treated with a chimeric CD8-depleting antibody (CM-T807 mouse V/human Fc anti-CD8 antibody) to reduce CD8+ T cells prior to imaging. Animals were administered s.c. with 10 mg/kg CD8 depleting antibody 3 days prior to imaging. CD8 depletion was confirmed by measuring the percentage of CD8 T cells in blood samples taken from each animal before and after depletion (FIG. 12).

Approximately 1-2 mCi of radiolabeled [I-124]CD8S365 anti-CD8 FN3 domain molecule was injected into the saphenous vein of a female NHP (cynomolgus macaque), while anesthetized with isoflurane in oxygen. Each animal was scanned in a large-bore microPET Focus 220 PET scanner (Siemens, Knoxville, Tenn.), with the bed moved to accommodate the entire body of the animal (head to lower abdomen). Each scan lasted approximately 1 h, and scans were acquired at 15 min, 2 h, and 24 h after injection. PET images were reconstructed using a 2D maximum likelihood expectation maximization (ML-EM) algorithm, into 3D images of voxel size 1.898×1.898×0.796 mm, dimensions 128×128×475. Blood samples were obtained at multiple time points from the saphenous vein in the opposite leg to the injection, and the blood radioactivity counted in a well counter.

Figure 13:
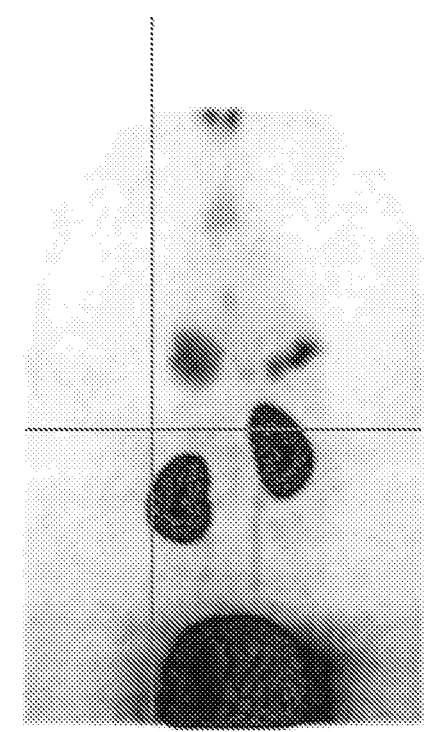
FIG. 13. Representative PET image showing the 365 anti-CD8A FN3 domain radiolabeled with I-124, taken at 2 h post-injection in a CD8-depleted animal. The image is a maximum intensity projection (anterior-posterior). This is to be compared against the non-depleted animal in FIG. 9, where the spleen is clearly visible above the kidney.

PET images were analyzed using PMOD v3.7 software (PMOD, Zurich, Switzerland). Regions-of-interest were drawn manually around organs such as spleen, kidneys and liver. Counts were converted to units of percent injected dose per gram of tissue (% ID/g), while blood radioactivity was presented as % ID. A representative PET image is shown in FIG. 13 for a depleted animal, showing a complete absence of the spleen signal seen in the non-depleted animal in FIG. 9.

Figure 14:
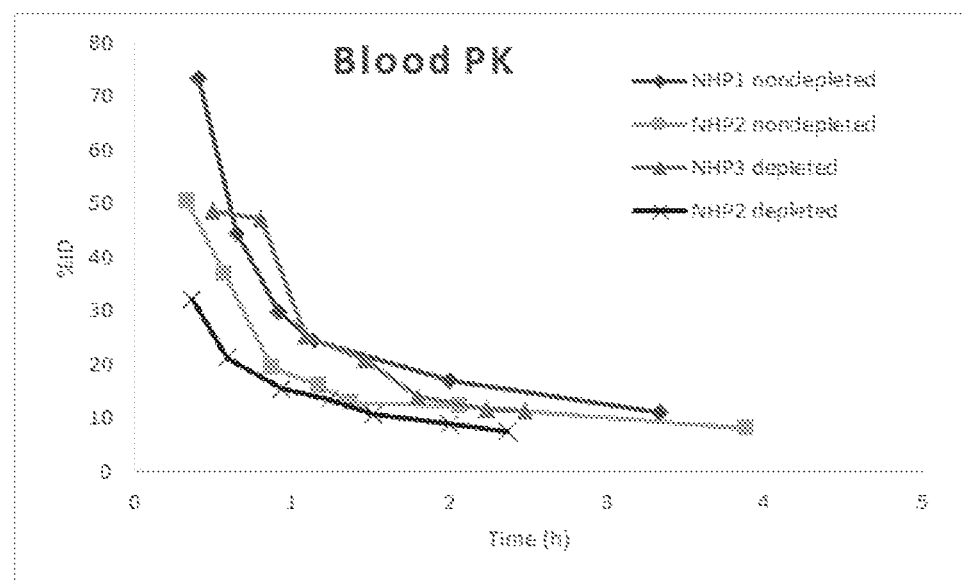
FIG. 14. Time-activity curves for blood radioactivity in cynomolgus monkeys for both depleted and non-depleted animals after administration of [$^{124}$I]-IPEM CD8S365.
Figure 15A:
FIGS. 15A and 15B. Time-activity curves for organ radioactivity in cynomolgus monkeys for both depleted and non-depleted animals. 15A includes kidneys, liver and spleen, while 15B is focused on the spleen.
Figure 15B:
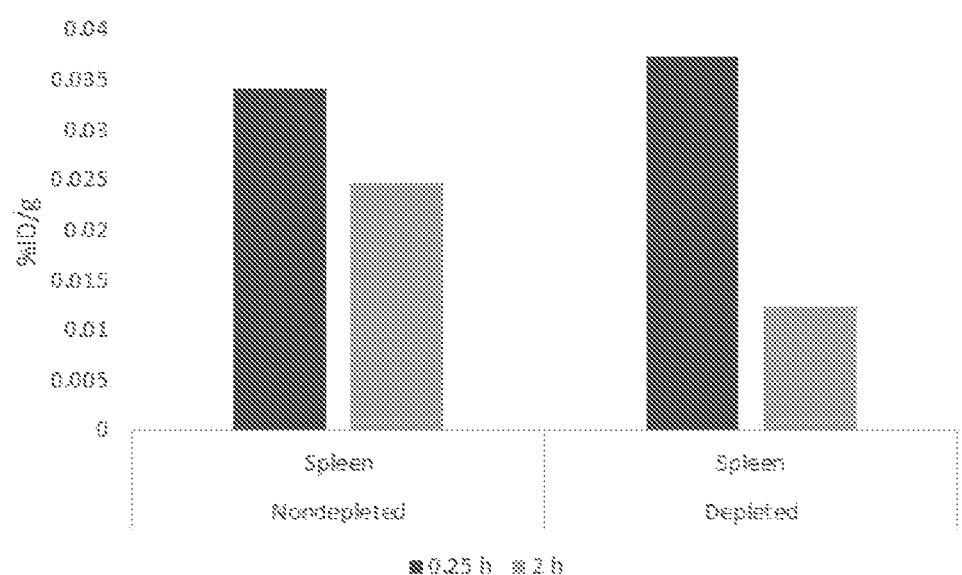

Blood kinetics for each NHP, both depleted and non-depleted, are shown in FIG. 14, while the organ uptakes are shown in FIG. 15. There is little difference in blood kinetics between the depleted and non-depleted animals. Spleen uptake at the earliest time point are similar between depleted and non-depleted, since this is dominated by blood flow. However, at later time points (2 h) the spleen uptake in the depleted animals is less than half that seen in the non-depleted animals, and is essentially at background levels, demonstrating CD8A specificity of the radiolabeled centyrin.

Example 12: Sensitivity and Specificity of Pet Imaging in CD8 Over-Expressing Tumors In order to determine the lowest number of cells that can be detected with the anti-CD8A FN3 domain molecules and PET, a study was performed in mice using different numbers of CD8 overexpressing cells. Forty 4-5 week old female NOD-scid IL2rγ$^{null}$ (NSG) mice (JAX Laboratory) were used, and acclimated for 7-10 days. Mice were group housed in IVC-cages under a 12-h light:dark cycle (lights on at 06:30 h) at a temperature of 19 to 22° C. Mice were fed a standard autoclaved laboratory chow and water ad libitum. Mice were ear-tagged and tails were tattooed 5-7 days prior to the start of the study to identify each animal.

HEK-293 parental and HEK-293-luc CD8+ over-expressing cell lines were maintained as 2D-cultures. Mice where implanted subcutaneously with a total of $10^6$ tumor cells in a 1:1 medium to cultrex mix containing varying ratios of HEK-293-Luc CD8+ expressing cells and HEK-293 parental cells. Once tumors were palpable, approximately $10^{-14}$ days and 200-300 mm$^3$ in size, the human CD8+ cells were visualized using [I-124]CD8-S365.

Luciferase expression of HEK-293-Luc CD8+ cells was quantified in vivo using bioluminescence imaging in an IVIS Spectrum optical imager (Perkin Elmer). Dynamic optical imaging was performed immediately after injection of 150 mg/kg D-luciferin to identify the peak light emission.

Approximately 0.2-0.5 mCi of radiolabeled anti-CD8A FN3 domain molecules was injected into the tail vein while anesthetized with isoflurane in oxygen. Each animal was scanned in an Inveon microPET-CT scanner (Siemens, Knoxville, Tenn.) for 20 min static scan. Scans were acquired at 2-3 h post tracer injection. PET images were reconstructed using a 2D maximum likelihood expectation maximization (ML-EM) algorithm, into 3D images of voxel size 0.776×0.776×0.796 mm, dimensions 128×128×159.

Figure 16:
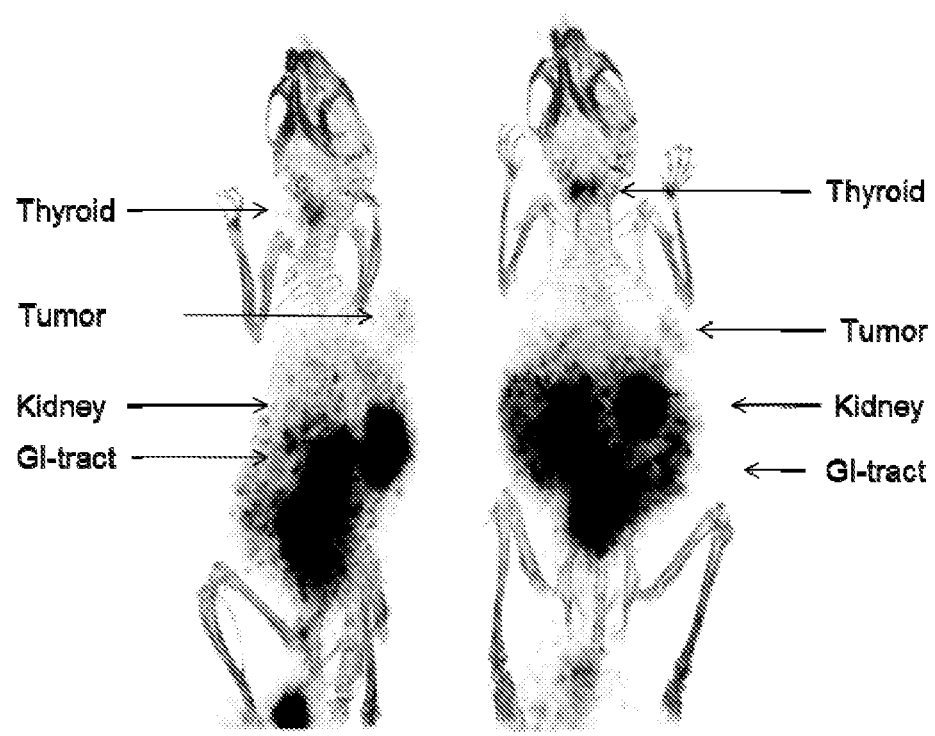
FIG. 16. Representative PET image of a two identically treated mice showing the CD8S365-IPEM radiolabeled with I-124, taken at 3 h post-injection. The image is a 3D maximum intensity projection, overlaid on a CT scan. Tumor (formed from HEK-293-luc transfected to over-express huCD8+) and other organs are indicated by arrows. The uptake in the thyroid is evidence of some de-iodination of the protein.

PET images were analyzed using PMOD v3.7 software (PMOD, Zurich, Switzerland). Regions-of-interest were drawn manually around the tumor and other organs such as spleen, kidneys and liver. Counts were converted to units of percent injected dose per gram of tissue (% ID/g). A representative PET image is shown in FIG. 16. Luciferase expression was quantified by drawing regions-of-interest in Living Image v4.4 software (Perkin Elmer). Light emission was measured in units of photons/sec/cm$^2$/steradian.

Figure 17:
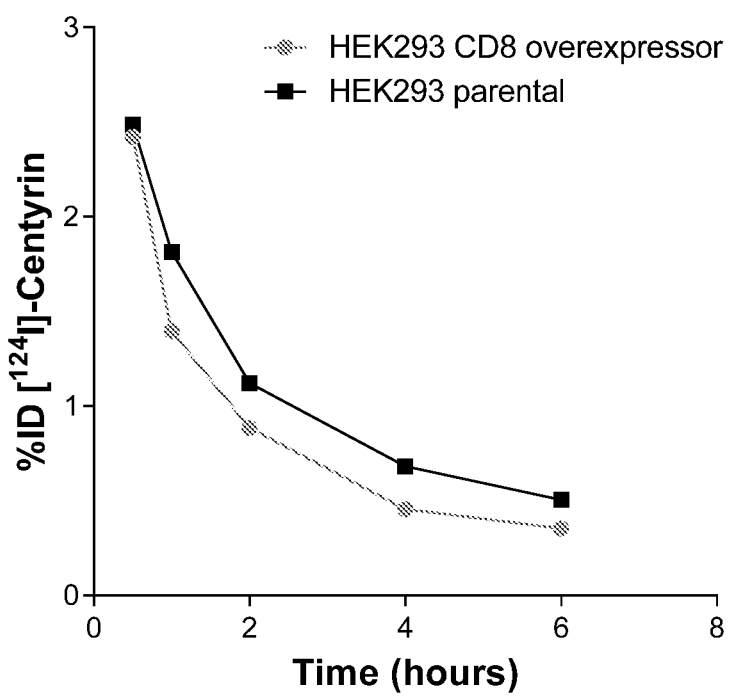
FIG. 17. Time-activity curve for blood radioactivity in mice bearing either HEK-293-luc CD8+ or HEK-293 parental tumors.
Figure 18:
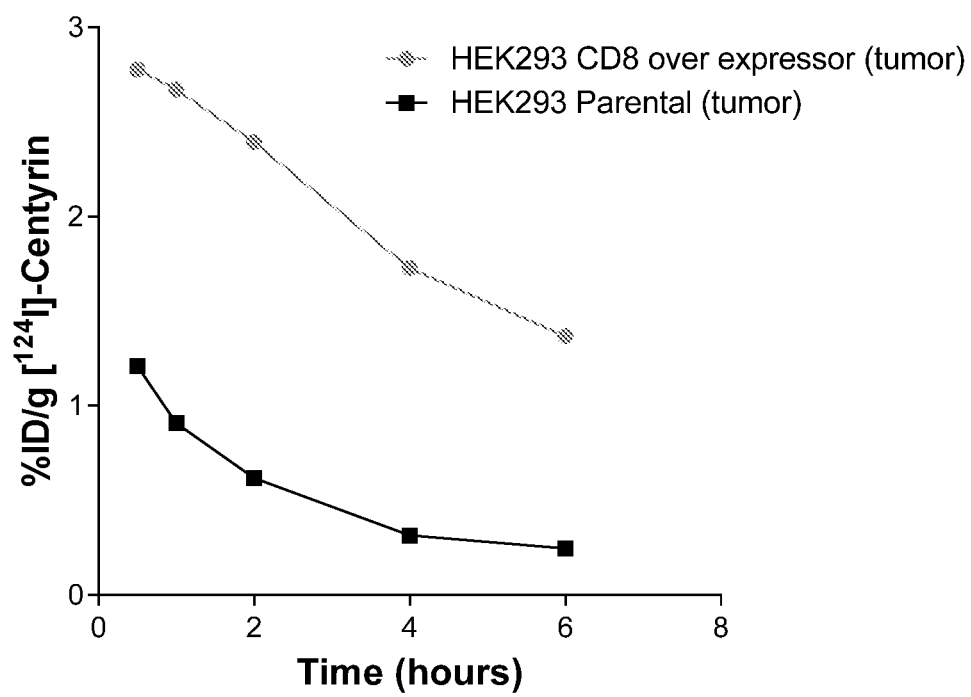
FIG. 18. Time-activity curve for tumor radioactivity in mice bearing either HEK-293-luc CD8+ or HEK-293 parental tumors.
Figure 19:
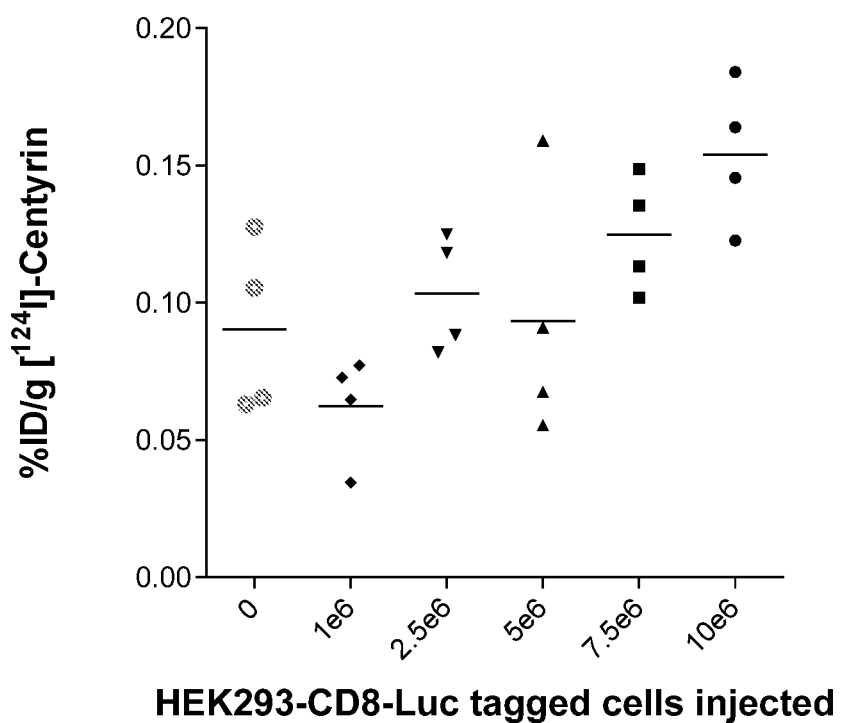
FIG. 19. Uptake of the I-124 labeled CD8S365 in the HEK293 CD8 overexpressing cells, as a function of the number of implanted cells.

Time-activity curves of radiolabeled anti-CD8A FN3 domain molecules in the blood and tumor for both CD8+ HEK293 cells and parental cells are shown in FIG. 17 and FIG. 18. There is a significant increase in anti-CD8A FN3-binding in the CD8-expressing cells compared to the parentals, while the blood activity is the same for both. Uptake of the anti-CD8A FN3 by the CD8+ HEK293 cells is shown in FIG. 19, as a function of number of implanted cells. Based on these data, it is estimated that the lowest level of detection is approximately 7.5×10$^6$ cells.

```
Sequence listing

SEQ ID No. 1 = Original Tencon Sequence
LPAPKNLVVSEVTEDSLRLSWTAPDAAFDSFLIQYQESEKVGEAINLTVPGSERSYDLTGLKPGTEYTVSIYGV
KGGHRSNPLSAEFTT SEQ ID No. 2 = TCL1 library
LPAPKNLVVSEVTEDSLRLSWTAPDAAFDSFLIQYQESEKVGEAINLTVPGSERSYDLTGLKPGTEYTVSIYGV
(X)_{7-12}PLSAEFTT;
wherein
X_1, X_2, X_3, X_4, X_5, X_6, X_7 is any amino acid; and
X_8, X_9, X_10, X_11 and X_12 are any amino acid or deleted SEQ ID No. 3 = TCL2 library
LPAPKNLVVSEVTEDSLRLSWX_1X_2X_3X_4X_5X_6X_7X_8SFLIQYQESEKVGEAINLTVPGSERSYDLTGLKPGTE
YTVSIYGVX_9X_10X_11X_12X_13SX_14X_15LSAEFTT;
```

Sequence listing wherein
X$_1$ is Ala, Arg, Asn, Asp, Glu, Gln, Gly, His, Ile, Leu, Lys, Phe, Pro, Ser, Thr, Trp, Tyr or Val;
X$_2$ is Ala, Arg, Asn, Asp, Glu, Gln, Gly, His, Ile, Leu, Lys, Phe, Pro, Ser, Thr, Trp, Tyr or Val;
X$_3$ Ala, Arg, Asn, Asp, Glu, Gln, Gly, His, Ile, Leu, Lys, Phe, Pro, Ser, Thr, Trp, Tyr or Val;
X$_4$ is Ala, Arg, Asn, Asp, Glu, Gln, Gly, His, Ile, Leu, Lys, Phe, Pro, Ser, Thr, Trp, Tyr or Val;
X$_5$ is Ala, Arg, Asn, Asp, Glu, Gln, Gly, His, Ile, Leu, Lys, Phe, Pro, Ser, Thr, Trp, Tyr or Val;
X$_6$ is Ala, Arg, Asn, Asp, Glu, Gln, Gly, His, Ile, Leu, Lys, Phe, Pro, Ser, Thr, Trp, Tyr or Val;
X$_7$ is Phe, Ile, Leu, Val or Tyr;
X$_8$ is Asp, Glu or Thr;
X$_9$ is Ala, Arg, Asn, Asp, Glu, Gln, Gly, His, Ile, Leu, Lys, Phe, Pro, Ser, Thr, Trp, Tyr or Val;
X$_{10}$ is Ala, Arg, Asn, Asp, Glu, Gln, Gly, His, Ile, Leu, Lys, Phe, Pro, Ser, Thr, Trp, Tyr or Val;
X$_{11}$ is Ala, Arg, Asn, Asp, Glu, Gln, Gly, His, Ile, Leu, Lys, Phe, Pro, Ser, Thr, Trp, Tyr or Val;
X$_{12}$ is Ala, Arg, Asn, Asp, Glu, Gln, Gly, His, Ile, Leu, Lys, Phe, Pro, Ser, Thr, Trp, Tyr or Val;
X$_{13}$ is Ala, Arg, Asn, Asp, Glu, Gln, Gly, His, Ile, Leu, Lys, Phe, Pro, Ser, Thr, Trp, Tyr or Val;
X$_{14}$ is Ala, Arg, Asn, Asp, Glu, Gln, Gly, His, Ile, Leu, Lys, Phe, Pro, Ser, Thr, Trp, Tyr or Val; and
X$_{15}$ is Ala, Arg, Asn, Asp, Glu, Gln, Gly, His, Ile, Leu, Lys, Phe, Pro, Ser, Thr, Trp, Tyr or Val.

SEQ ID No. 4 = Stabilized Tencon (Tencon 27)
LPAPKNLVVSRVTEDSARLSWTAPDAAFDSFLIQYQESEKVGEAIVLTVPGSERSYDLTGLKPGTEYTVSI
YGVKGGHRSNPLSAIFTT SEQ ID No. 5 = TCL7 (FG and BC loops)
LPAPKNLVVSRVTEDSARLSWX$_1$X$_2$X$_3$X$_4$X$_5$X$_6$X$_7$X$_8$X$_9$FDSFLIQYQESEKVGEAIVLTVPGSERSYDLTGLK
PGTEYTVSIYGVX$_{10}$X$_{11}$X$_{12}$X$_{13}$X$_{14}$X$_{15}$X$_{16}$X$_{17}$X$_{18}$X$_{19}$SNPLSAIFTT;
wherein
X$_1$, X$_2$, X$_3$, X$_4$, X$_5$, X$_6$, X$_{10}$, X$_{11}$, X$_{12}$, X$_{13}$, X$_{14}$, X$_{15}$ and X$_{16}$ are A, D, E, F, G, H, I, K, L, N, P, Q, R, S, T, V, W or Y; and
X$_7$, X$_8$, X$_9$, X$_{17}$, X$_{18}$ and X$_{19}$, are A, D, E, F, G, H, I, K, L, N, P, Q, R, S, T, V, W, Y or deleted SEQ ID No. 6 = TCL9 (FG loop)
LPAPKNLVVSRVTEDSARLSWTAPDAAFDSFLIQYQESEKVGEAIVLTVPGSERSYDLTGLKPGTEYTV
SIYGVX$_1$X$_2$X$_3$X$_4$X$_5$X$_6$X$_7$X$_8$X$_9$X$_{10}$X$_{11}$X$_{12}$SNPLSAIFTT;
wherein
X$_1$, X$_2$, X$_3$, X$_4$, X$_5$, X$_6$ and X$_7$, is A, D, E, F, G, H, I, K, L, N, P, Q, R, S, T, V, W or Y; and
X$_8$, X$_9$, X$_{10}$, X$_{11}$ and X$_{12}$ is A, D, E, F, G, H, I, K, L, N, P, Q, R, S, T, V, W, Y or deleted.

SEQ ID No. 7 = TCL14 library
LPAPKNLVVSRVTEDSARLSWTAPDAAFDSFX$_1$IX$_2$YX$_3$EX$_4$X$_5$X$_6$X$_7$GEAIVLTVPGSERSYDLTGLKPG
TEYX$_8$VX$_9$IX$_{10}$GVKGGX$_{11}$X$_{12}$SX$_{13}$PLSAIFTT;
wherein
X$_1$, X$_2$, X$_3$, X$_4$, X$_5$, X$_6$, X$_{10}$, X$_{11}$, X$_{12}$ and X$_{13}$ are A, D, E, F, G, H, I, K, L, N, P, Q, R, S, T, V, W, Y, or M.

SEQ ID No. 8 = TCL24 Library
TCL24 Library (SEQ ID NO: 8)
LPAPKNLVVSRVTEDSARLSWTAPDAAFDSFX$_1$IX$_2$YX$_3$EX$_4$X$_5$X$_6$X$_7$GEAIX$_8$LX$_9$VPGSERSYDLTGLKPG
TEYX$_{10}$NX$_{11}$IX$_{12}$GVKGGX$_{13}$X$_{14}$SX$_{15}$PLX$_{16}$AX$_{17}$FTT;
wherein
X$_1$, X$_2$, X$_3$, X$_4$, X$_5$, X$_6$, X$_{10}$, X$_{11}$, X$_{12}$ and X$_{13}$ are A, D, E, F, G, H, I, K, L, N, P, Q, R, S, T, V or W.

SEQ ID No. 9 = Sloning-FOR
GTGACACGGCGGTTAGAAC

SEQ ID No. 10 = Sloning-REV
GCCTTTGGGAAGCTTCTAAG

SEQ ID No. 11 = POP2250
CGGCGGTTAGAACGCGGCTACAATTAATAC

Sequence listing

SEQ ID No. 12 = DigLigRev
CATGATTACGCCAAGCTCAGAA

SEQ ID No. 13 = BC9
GTGACACGGCGGTTAGAACGCGGCTACAATTAATACATAACCCCATCCCCCTGTTGACAATTAATCACAATAT
CGGCTCGTATAATGTGTGGAATTGTGAGCGGATATTCACACAGGAAACAGGATCTACCATGCTGCCGGCGCCG
AAAAACCTGGTTGTTTCTGAAGTTACCGAAGACTCTCTGCGTCTGTCTTGGTTYGACTCTTTCCTGATCCAGT
ACCAGGAATCTGAAAAAGTTGGTGAAGCGATCAACCTGACCGTTCCGGGTTCTGAACGTTCTTACGACCTGAC
CGGTCTGAAACCGGGTACCGAATACACCGTTTCTATCTACGGTGTTCTTAGAAGCTTCCCAAAGGC

SEQ ID No. 14 = BC8
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAACCTGGTTGTTTCTGAAGTTACCGAAGACTCTCTGCGTCTGTCTTGGTTYGACTCTTTCCTGATCCAGT
ACCAGGAATCTGAAAAAGTTGGTGAAGCGATCAACCTGACCGTTCCGGGTTCTGAACGTTCTTACGACCTGAC
CGGTCTGAAACCGGGTACCGAATACACCGTTTCTATCTACGGTGTTCTTAGAAGCTTCCCAAAGGC

SEQ ID No. 15 = BC7
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAACCTGGTTGTTTCTGAAGTTACCGAAGACTCTCTGCGTCTGTCTTGGTTYGACTCTTTCCTGATCCAGT
ACCAGGAATCTGAAAAAGTTGGTGAAGCGATCAACCTGACCGTTCCGGGTTCTGAACGTTCTTACGACCTGAC
CGGTCTGAAACCGGGTACCGAATACACCGTTTCTATCTACGGTGTTCTTAGAAGCTTCCCAAAGGC

SEQ ID No. 16 = BC6
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAACCTGGTTGTTTCTGAAGTTACCGAAGACTCTCTGCGTCTGTCTTGGTTYGACTCTTTCCTGATCCAGT
ACCAGGAATCTGAAAAAGTTGGTGAAGCGATCAACCTGACCGTTCCGGGTTCTGAACGTTCTTACGACCTGAC
CGGTCTGAAACCGGGTACCGAATACACCGTTTCTATCTACGGTGTTCTTAGAAGCTTCCCAAAGGC

SEQ ID No. 17 = 130mer-L17A
CGGCGGTTAGAACGCGGCTACAATTAATACATAACCCCATCCCCCTGTTGACAATTAATCATCGGCTCGTATA
ATGTGTGGAATTGTGAGCGGATAACAATTTCACACAGGAAACAGGATCTACCATGCTG SEQ ID No. 18 = POP222ext
CGG CGG TTA GAA CGC GGC TAC AAT TAA TAC SEQ ID No. 19 = LS1114
CCA AGA CAG ACG GGC AGA GTC TTC GGT AAC GCG AGA AAC AAC CAG
GTT TTT CGG CGC CGG CAG CAT GGT AGA TCC TGT TTC SEQ ID No. 20 = LS1115
CCG AAG ACT CTG CCC GTC TGT CTT GG SEQ ID No. 21 = L51117
CAG TGG TCT CAC GGA TTC CTG GTA CTG GAT CAG GAA AGA GTC GAA SEQ ID No. 22 = SDG10
CATGCGGTCTCTTCCGAAAAAGTTGGTGAAGCGATCGTCCTGACCGTTCCGGGT SEQ ID No. 23 = 5DG24
GGTGGTGAAGATCGCAGACAGCGGGTTAG SEQ ID No. 24 = P0P2222
CGGCGGTTAGAACGCGGCTAC SEQ ID No. 25 = SDG28
AAGATCAGTTGCGGCCGCTAGACTAGAACCGCTGCCACCGCCGGTGGTGAAGATCGCAGAC SEQ ID No. 26 = FG12
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA
ACGTTCTTACGACCTGACCGGTCTGAAACCGGGTACCGAATACACCGTTTCTATCTACGGTGTTNNNNNNNNN
NNNNNNNNNNNNNNNNNNNNNNNNNNTCTAACCCGCTGTCTGCGATCTTCACCACCGGCGGTCACCATCACCATC
ACCATGGCAGCGGTTCTAGTCTAGCGGCCGCAACTGATCTTGGC SEQ ID No. 27 = FG11
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA

```
ACGTTCTTACGACCTGACCGGTCTGAAACCGGGTACCGAATACACCGTTTCTATCTACGGTGTTNNNNNNNNN
NNNNNNNNNNNNNNNNNNNNNNNNNNNTCTAACCCGCTGTCTGCGATCTTCACCACCGGCGGTCACCATCACC
ATCACCATGGCAGCGGTTCTAGTCTAGCGGCCGCAACTGATCTTGGC

SEQ ID No. 28 = FG10
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA
ACGTTCTTACGACCTGACCGGTCTGAAACCGGGTACCGAATACACCGTTTCTATCTACGGTGTTNNNNNNNNN
NNNNNNNNNNNNNNNNNNNNNTCTAACCCGCTGTCTGCGATCTTCACCACCGGCGGTCACCATCACCATCACC
ATGGCAGCGGTTCTAGTCTAGCGGCCGCAACTGATCTTGGC

SEQ ID No. 29 = FG9
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA
ACGTTCTTACGACCTGACCGGTCTGAAACCGGGTACCGAATACACCGTTTCTATCTACGGTGTTNNNNNNNNN
NNNNNNNNNNNNNNNNNNTCTAACCCGCTGTCTGCGATCTTCACCACCGGCGGTCACCATCACCATCACCATG
GCAGCGGTTCTAGTCTAGCGGCCGCAACTGATCTTGGC

SEQ ID No. 30 = FG8
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA
ACGTTCTTACGACCTGACCGGTCTGAAACCGGGTACCGAATACACCGTTTCTATCTACGGTGTTNNNNNNNNN
NNNNNNNNNNNNNNNTCTAACCCGCTGTCTGCGATCTTCACCACCGGCGGTCACCATCACCATCACCATGGCA
GCGGTTCTAGTCTAGCGGCCGCAACTGATCTTGGC

SEQ ID No. 31 = FG7
GTGACACGGCGGTTAGAACGCGGCTACAATTAATACATAACCCCATCCCCCTGTTGACAATTAATCATCGGCT
CGTATAATGTGTGGAATTGTGAGCGGATAACAATTTCACACAGGAAACAGGATCTACCATGCTGCCGGCGCCG
AAAAAACCTGGTTGTTTCTCGCGTTACCGAAGACTCTGCGCGTCTGTCTTGGACCGCGCCGGACGCGGCGTTCG
ACTCTTTCCTGATCCAGTACCAGGAATCTGAAAAAGTTGGTGAAGCGATCGTGCTGACCGTTCCGGGTTCTGA
ACGTTCTTACGACCTGACCGGTCTGAAACCGGGTACCGAATACACCGTTTCTATCTACGGTGTTNNNNNNNNN
NNNNNNNNNNNTCTAACCCGCTGTCTGCGATCTTCACCACGGTCACCATCACCATCACCATGGCAGCGGTTC
TAGTCTAGCGGCCGCAACTGATCTTGGC

SEQ ID NO: 32 FG loop of Tencon
KGGHRSN

SEQ ID No. 33 = Tcon 6
AAGAAGGAGAACCGGTATGCTGCCGGCGCCGAAAAAC

SEQ ID No. 34 = Tcon5E86Ishort
GAG CCG CCG CCA CCG GTT TAA TGG TGA TGG TGA
TGG TGA CCA CCG GIG GIG AAG ATC GCA GAC AG >SEQID No 35: CD8W7
SQFRVSPLDRTWNLGETVELKCQVLLSNPTSGCSWLFQPRGAAASPTFLLYLSQNKPKAAEGLDTQRFSGKRL
GDTFVLTLSDFRRENEGYYFCSALSNSIMYFSHFVPVFLPAKPTTTPAPRPPTPAPTIASQPLSLRPEACRPA
GSGSGSDYKDDDDKDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNVFSC
SVMHEALHNHYTQKSLSLSPGK >SEQID No 36: CD8W13
SQFRVSPLDRTWNLGETVELKCQVLLSNPTSGCSWLFQPRGAAASPTFLLYLSQNKPKAAEGLDTQRFSGKRL
GDTFVLTLSDFRRENEGYYFCSALSNSIMYFSHFVPVFLPAKPTTTPAPRPPTPAPTIASQPLSLRPEACRPA
AGGAVHTRGLDFACDGGGGSDYKDDDDKGGGGSHHHHHHDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK >SEQID No. 37: mIgGK
signal peptide
Metddllwvlllwvpgstg >SEQID No. 38. Human Fc
Dkthtcppcpapellggpsvflfppkpkddmisrtpevtcyvvdvshedpevkfnwyvdgvevhnaktkpreeqy
nstyrwsvltvlhqdwingkeykckvsnkalpapiektiskakgqprepqvytlppsrdeltknqvsltclvkgf
ypsdiavewesngqpennykttppvldsdgsfflyskltvdksrwqqgnvfscsvmhealhnhytqkslslspgk >SEQID No. 39: linker sequence
Ggggsdykddddkggggshhhhhh
```

-continued

| Clone ID | SEQ ID No | Amino Acid Sequence |
|---|---|---|
| P282AR9P1356_A10 | 40 | LPAPKNLVVSRVTEDSARLSWHTATNSFDSFLIQYQESEKVGEAIVL TVPGSERSYDLTGLKPGTEYTVSIYGVDVDYNPTGRPVSSNPLSAIF TT |
| P282AR9P1356_A4 | 41 | LPAPKNLVVSRVTEDSARLSWVKRPNSFDSFLIQYQESEKVGEAIVL TVPGSERSYDLTGLKPGTEYTVSIYGVDVVDYEGRPRWSNPLSAIFT T |
| P282AR9P1356_A6 | 42 | LPAPKNLVVSRVTEDSARLSWSKTDSSFDSFLIQYQESEKVGEAIVL TVPGSERSYDLTGLKPGTEYTVSIYGVDVVYIEGNPVFSNPLSAIFTT |
| P282AR9P1356_B9 | 43 | LPAPKNLVVSRVTEDSARLSWPEGDRPFFDSFLIQYQESEKVGEAIV LTVPGSERSYDLTGLKPGTEYTVSIYGVDVKWEGNRPVASNPLSAIF TT |
| P282AR9P1356_D3 | 44 | LPAPKNLVVSRVTEDSARLSWTRHETSFDSFLIQYRESEKVGEAIVL TVPGSERSYDLTGLKPGTEYTVSIYGVVVEYDAAGNPKYSNPLSAIF TT |
| P282AR9P1356_H1 | 45 | LPAPKNLVVSRVTEDSARLSWIPNPSSFDSFLIQYQESEKVGEAIVLT VPGSERSYDLTGLKPGTEYTVSIYGVDVVFDPVGFPSHSNPLSAIFT T |
| P282AR9P1356_H6 | 46 | LPAPKNLVVSRVTEDSARLSWRKRANSFDSFLIQYQESEKVGEAIVL TVPGSERSYDLTGLKPGTEYTVSIYGVHVEYDQHGRPRWSNPLSAI FU |
| P282BR9P1357_A9 | 47 | LPAPKNLVVSRVTEDSARLSWKANRTTDLHFDSFLIQYQESEKVGE AIVLTVPGSERSYDLTGLKPGTEYTVSIYGVDVQYDGQQPLYSNPLS AIFTT |
| P282BR9P1357_B2 | 48 | LPAPKNLVVSRVTEDSARLSWNPSEDPQRFDSFLIQYQESEKVGEA IVLIVPGSERSYDLTGLKPGTEYTVSIYGVDVKWEGNRPVASNPLS AIFTT |
| P282BR9P1357_C10 | 49 | LPAPKNLVVSRVTEDSARLSWWSNDNRPIFDSFLIQYQESEKVGEA IVLIVPGSERSYDLTGLKPGTEYTVSIYGVDVKWEGNRPVASNPLS AIFTT |
| P282BR9P1357_C4 | 50 | LPAPNNLVVSRVTEDSARLSWPFVSQNKPHFDSFLIQYQESEKVGE AIVLTVPGSERSYDLTGLKPGTEYTVSIYGVDVKWEGNRPVASNPL SAIFTT |
| P282BR9P1357_D12 | 51 | LPAPKNLVVSRVTEDSARLSWGQYITAFSFDSFLIQYQESEKVGEAI VLTVPGSERSYDLTGLKPGTEYTVSIYGVDVAWFQGKPTWSNPLS AIFTT |
| P282BR9P1357_D2 | 52 | LPAPKNLVVSRVTEDSARLSWIKDGHPRHFDSFLIQYQESEKVGEAI VLTVPGSERSYDLTGLKPGTEYTVSIYGVDVVYDRGQLISSNPLSAIF TT |
| P282BR9P1357_E5 | 53 | LPAPKNLVVSRVTEDSARLSWWPRKYQRPFDSFLIQYQESEKVGE AIVLTVPGSERSYDLTGLKPGTEYTVSIYGVDIEWIGNRPIASNPLSAI FU |
| P282BR9P1357_G9 | 54 | LPAPKNLVVSRVTEDSARLSWPIASQIHSPFDSFLIQYQESEKVGEAI VLTVPGSERSYDLTGLKPGTEYTVSIYGVDVKYDIDSRPISSNPLSAIF TT |
| P282BR9P1357_H3 | 55 | LPAPKNLVVSRVTEDSARLSWKKREYQDPGFDSFLIQYQESEKVGE AIVLTVPGSERSYDLTGLKPGTEYTVSIYGVDVKWEGNRPVASNPL SAIFTT |
| P282CR9P1358_C2 | 56 | LPAPKNLVVSRVTEDSARLSWTAPDAAFDSFKIAYPEWPSNGEAIV LTVPGSERSYDLTGLKPGTEYAVFIWGVKGGAFSNPLSAIFTT |
| P282CR9P1358_C5 | 57 | LPAPKNLVVSRVTEDSARLSWTAPDAAFDSFLIAYPEWPDSGEAIV LTVPGSERSYDLTGLKPGTEYAVFIWGVKGGPLSHPLSAIFTT |
| P282CR9P1358_D10 | 58 | LPAPKNLVVSRVTEDSARLSWTAPDAAFDSFLISYPEYPPPGEAIVL TVPGSERSYDLTGLKPGTEYFVIIFGVKGGDTSWPLSAIFTT |

| | | |
|---|---|---|
| Sequence listing | | |
| P282CR9P1358_F11 | 59 | LPAPKNLVVSRVTEDSARLSWTAPDAAFDSFLIAYPEWPIFEGEAIV LTVPGSERSYDLTGLKPGTEYFVVIYGVKGGEQSSPLSAIFTT |
| P282CR9P1358_F5 | 60 | LPAPKNLVVSRVTEDSARLSWTAPDAAFDSFWISYPEWPPDGEAI VLTVPGSERSYDLTGLKPGTEYFVIIWGVKGGETSAPLSAIFTT |
| P282DR9P1359_A12 | 61 | LPAPKNLVVSRVTEDSARLSWTAPEAAFDSFQIAYPEWPPPREAIV LTVPGSERSYDLTGLKPGTEYFVVIQGVKGGEISWPLSAIFTT |
| P282DR9P1359_A7 | 62 | LPAPKNLVVSRVTEDSARLSWTAPDAAFDSFRIGYPELEKLGYGEAI VLTVPGSERSYDLTGLKPGTEYWVIIWGVKGGENSWPLSAIFTT |
| P282DR9P1359_A8 | 63 | LPAPKNLVVSRVTEDSARLSWTAPDAAFDSFRIAYPEWPVQGEAIV LTVPGSERSYDLTGLKPGTEYFVIIYGVKGGELSPPLSAIFTT |
| P282DR9P1359_B2 | 64 | LPAPKNLVVSRVTEDSARLSWTAPDAAFDSFWIAYTEWPIPYEEAG QEGEAIVLTVPGSERSYDLTGLKPGTEYWVSIYGVKGGPNSQPLSAI FTT |
| P282DR9P1359_C10 | 65 | LPAPKNLVVSRVTEDSARLSWTAPDAAFDSFAIVYPEWPTDGEAIV LTVPGSERSYDLTGLKPGTEYAVFIWGVKGGNQSWPLSAIFTT |
| P282DR9P1359_C11 | 66 | LPAPKNLVVSRVTEDSARLSWTAPDAAFDSFKIAYPEFPPPGEAIVL TVPGSERSYDLTGLKPGTEYYVIIIGVKGGTDSWPLSAIFTT |
| P282DR9P1359_C12 | 67 | LPAPKNLVVSRVTEDSARLSWTAPDAAFDSFYISYPEWPVPGEAIV LTVPGSERSYDLTGLKPGTEYWVIYGVKGGALSVPLSAIFTT |
| P282DR9P1359_C5 | 68 | LPAPKNLVVSRVTEDSARLSWTAPDAAFDSFWITYPEWPDPGGEA IVLTVPGSERSYDLTGLKPGTEYFVVIYGVKGGEIYSPLSAIFTT |
| P282DR9P1359_D12 | 69 | LPAPKNLVVSRVTEDSARLSWTAPDAAFDSFRIAYPETATWGEAIV LTVPGSERSYDLTGLKPGTEYFVIIYGVKGGFESAPLSAIFTT |
| P282DR9P1359_E11 | 70 | LPAPKNLVVSRVTEDSARLSWTAPDAAFDSFYISYPEWPPVGEAIV LTVPGSERSYDLTGLKPGTEYWVIIYGVKGGAISTPLSAIFTT |
| P282DR9P1359_E2 | 71 | LPAPKNLVVSRVTEDSARLSWTAPDAAFDSFNIFYPEIVTWGEAIVL TVPGSERSYDLTGLKPGTEYWVNIVGVKGGDNSWPLSAIFTT |
| P282DR9P1359_E3 | 72 | LPAPKNLVVSRVTEDSARLSWTAPDAAFDSFAIAYPELPLGGEAIVL TVPGSERSYDLTGLKPGTEYFVIIYGVKGGVESFPLSAIFTT |
| P282DR9P1359_E5 | 73 | LPAPKNLVVSRVTEDSARLSWTAPDAAFDSFAISYPEWPVPGEAIV LTVPGSERSYDLTGLKPGTEYFVIIYGVKGGLYSAPLSAIFTT |
| P282DR9P1359_E6 | 74 | LPAPKNLVVSRVTEDSARLSWTAPDAAFDSFWIAYPEWPVQGEAI VLTVPGSERSYDLTGLKPGTEYFVVIQGVKGGTPSWPLSAIFTT |
| P282DR9P1359_E8 | 75 | LPAPKNLVVSRVTEDSARLSWTAPDAAFDSFQIAYPEWPVIGEAIV LTVPGSERSYDLTGLKPGTEYWVIIQGVKGGYTSWPLSAIFTT |
| P282DR9P1359_F11 | 76 | LPAPKNLVVSRVTEDSARLSWTAPDAAFDSFDIFYPELPIHGEAIVL TVPGSERSYDLTGLKPGTEYWVNITGVKGGDFSWPLSAIFTT |
| P282DR9P1359_F2 | 77 | LPAPKNLVVSRVTEDSARLSWTAPDAAFDSFNIAYPEALHPGYGEA IVLIVPGSERSYDLTGLKPGTEYWVIIGGVKGGQKSWPLSAIFTTGG HHHDHH |
| P282DR9P1359_F3 | 78 | LPAPKNLVVSRVTEDSARLSWTAPDAAFDSFYITYPEWPVQGEAIV LTVPGSERSYDLTGLKPGTEYWVIIYGVKGGTESEPLSAIFTT |
| P282DR9P1359_F5 | 79 | LPAPKNLVVSRVTEDSARLSWTAPDAAFDSFQIAYPEWPPPGEAIV LTVPGSERSYDLTGLKPGTEYFVIIQGVKGGVESWPLSAIFTT |
| P282DR9P1359_F6 | 80 | LPAPKNLVVSRVTEDSARLSWTAPDAAFDSFDIAYPEWPTTGEAIV LTVPGSERSYDLTGLKPGTEYFVVIWGVKGGDHSAPLSAIFTT |
| P282DR9P1359_F7 | 81 | LPAPKNLVVSRVTEDSARLSWTAPDAAFDSFAIAYPEWPPQGEAIV LTVPGSERSYDLTGLKPGTEYFVVIYGVKGGSYSAPLSAIFTT |
| P282DR9P1359_G4 | 82 | LPAPKNLVVSRVTEDSARLSWTAPDAAFDSFEIAYPEWPPPGEAIV LTVPGSERSYDLTGLKPGPEYFVVIQGVKGGDPSFPLSAIFTTGGNH HHHH |

-continued

| Sequence listing | | |
|---|---|---|
| P282DR9P1359_G7 | 83 | LPAPKNLVVSRVTEDSARLSWTAPDAAFDSFAITYIEKEHIEDGEA1VLTVPGSERSYDLTGLKPGTEYWVPIWGVKGGANSWPLSAIFTT |
| P282DR9P1359_H5 | 84 | LPAPKNLVVSRVTEDSARLSWTAPDAAFDSFNIAYPEALHPGYGEAIVLTVPGSERSYDLTGLKPGTEYFVVIYGVKGGTNSEPLSAIFTT |
| P282ER9P1360_A9 | 85 | LPAPKNLVVSRVTEDSARLSWTAPDAAFDSFGILYYEPVDSGEAITLPIPGSERSYDLTGLKPGTEYWVVITGVKGGAPSTPLGAIFTT |
| P282ER9P1360_C1 | 86 | LPAPKNLVVSRVTEDSARLSWTTPDAAFDSFGILYYEPVDSGEAITLPVPGSERSYDLTGLKPGTEYWVVITGVKGGAPSTPLGAIFTT |
| P282ER9P1360_C4 | 87 | LPAPKNLVVSRVTEDSARLSWTAPDAAFDSFGITYYEPNHGGEAISLSVPGSERSYDPTGLKPGTEYWVVITGVKGGAPSTPLGAIFTT |
| P282ER9P1360_C6 | 88 | LSAPKNLVVSRVTEDSARLSWTAPDAAFDSFGILYYEPVDSGEAITLPIPGSERSYDLTGLKPGTEYWVVITGVKGGAPSTPLGAIFTT |
| P282ER9P1360_C8 | 89 | LPAPKNLVVSRVTEDSARLSWTAPDAAFDSFGILYYEPVDSGEAITLPVPGSERSYDLTGLKPGTEYWVVITGVKGGAPSTPLGTIFTT |
| P282ER9P1360_D11 | 90 | LPAPKNLVVSRVTEDSARLSWTAPDAAFDSFGILYYEPVDSGEAITLPVPGSERSYDLTGLKPGTEYFVIIVGVKGGYPSIPLGAAFTT |
| P282ER9P1360_E4 | 91 | LPAPKNLVVSRVTEDSARLSWTAPDAAFDSFGILYYEPVDSGEAITLPVLGSERSYDLTGLKPGTEYWVVITGVKGGAPSTPLGAIFTT |
| P282ER9P1360_F11 | 92 | LPAPKNLVVSRVTEDSARLSWIAPDAAFDSFSIAYVEAELVGEAIQLVVPGSERSYDLTGLKPGTEYWVVILGVKGGNPSNPLGASFTT |
| P282ER9P1360_G10 | 93 | LPAPKNLVVSRVTEDSARLSWTAPDAAFDSFAIWYVEQHPFGEA1PLFVPGSERSYDLTGLKPGTEYTVGIRGVKGGNFSTPLIAHFTT |
| P282ER9P1360_G7 | 94 | LPAPKNLVVSRVTEDSARLSWTAPDAAFDSFGILYYEPVDSGEAITLPVPGSERSYDLTGLKPGTEYWVVITGVKGGAPSTPLGAILU |
| P282ER9P1360_H10 | 95 | LPAPKNLVVSRVTEDSARLSWTAPDAAFDSFEIYYPEWPFAGEAIGLPVPGSERSYDLTGLKPGTEYFVVIYGVKGGELSEPLTAQFTT |
| P282ER9P1360_H2 | 96 | LPAPKNLVVSRVTEDSARLSWTAPDAAFDSFSIAYVEAELVGEAIQLVVPGSERSYDLTGLKPGTEYWVVILGVKGGNPSNPLGASFTTT |
| P282ER9P1360_H3 | 97 | LPAPKNLVVSRVTEDSARLSWTAPDAAFDSFSIAYVEAELVGEAIQLVVPGSERSYDLTGLKPGTEYWVVILGVKGGNPSNPLGASFTT |
| P282FR9P1361_A3 | 98 | LPAPKNLVVSRVTEDSARLSWTAPDAAFDSFDIWYAEYGYPGEAIVLTVPGSERSYDLTGLKPGTEYDVAIVGVKGGNRSYPLSAIFTT |
| P282FR9P1361_A5 | 99 | LPAPKNLVVSRVTEDSARLSWTAPDAAFDSFGILYYEPVDSGEAITLPVPGSERSYDLTGLKPGTEYWVVITGVKGGAPSTPLGAIFTT |
| P282FR9P1361_C7 | 100 | LPAPKNLVVSRVTEDSARLSWTAPDAAFDSFGIWYHEYGGDEA1VLTVPGSERSYDLTGLKPGTEYDVAIWGVKGGDVSYPLSAIFTT |
| P282FR9P1361_D3 | 101 | LPAPKNLVVSRVTEDSARLSWTAPDAAFDSFDIWYAEYGYPGEAIVLTVPGSERSYDLTGLNPGTEYDVAISGVKGGPRSYPLSAIFTT |
| P282FR9P1361_E12 | 102 | LPAPKNLVVSRVTEDSARLSWTAPDAAFDSLGITYWESPYAGEAIVLTVPGSERSYDLTGLKPGTEYGVFILGVKGGYPSAPLSAIFTT |
| P282FR9P1361_F1 | 103 | LPAPKNLVVSRVTEDSARLSWTAPDAAFDSFGIWYAEYGYSGEAIVLTVPGSERSYDLTGLKPGTEYDVAIWGVKGGVRSYPLSAIFTT |
| P282FR9P1361_F11 | 104 | LPAPKNLVVSRVTEDSARLSWTAPDAAFDSFGIWYREYGGSGEAIVLTVPGSERSYDLTGLKPGTEYDVAIWGVKGGVRSYPLSAIFTT |
| P282FR9P1361_F2 | 105 | LPAPKNLVVSRVTEDSARLSWTAPDAAFDSFDIWYAEYGYPGEAIVLTVPGSERSYDLTGLKPGTEYDVAISGIKGGPRSYPLSAIFTT |
| P282FR9P1361_F3 | 106 | LPAPKNLVVSRVTEDSARLSWTAPDAAFDSFDIWYAEYGYPGEAIVLTVPGSERSYDLTGLKPGTEYDVAISGAKGGPRSYPLSAIFTT |
| P282FR9P1361_F7 | 107 | LPAPKNLVVSRVTEDSARLSWTAPDAAFDSFPIWYREYATGEAIVLTVPGSERSYDLTGLKPGTEYDVVITGVKGGYPSYPLSAIFTT |

| | | |
|---|---|---|
| P282FR9P1361_G9 | 108 | LPAPKNLVVSRVTEDSARLSWTAPDAAFDSFGITYWESPYAGEAIV LTVPGSERSYDLTGLKPGTEYGVFILGVKGGYPSAPLSAIFTT |
| P282FR9P1361_H4 | 109 | LPAPKNLVVSRVTEDSARLSWTAPDAAFDSFGIWYAEYGYSGEAIV LTVPGSERSYDLTGLKPGTEYDVAIYGVKGGSPSYPLSAIFTT |
| P282FR9P1361_H5 | 110 | LPAPKNLVVSRVTEDSARLSWTAPDAAFDSFDIWYAEYGYPGEAIV LTVPGSERSYDLTGLKPGTEYDVAISGVKGGPRSYPLSAIFTT |
| P283AR9P1362_A3 | 111 | LPAPKNLVVSRVTEDSARLSWKRIDSPFDSFLIQYQESEKVGEAIVLT VPGSERSYDLTGLKPGTEYTVSIYGVDVKYDIDSRPISSNPLSAIFTT |
| P283AR9P1362_A4 | 112 | LPAPKNLVVSRVTEDSARLSWIGHDSGFDSFLIQYQESEKVGEAIVL TVPGSERSYDLTGLKPGTEYTVSIYGVDVKYDIDSRPISSNPLSAIFTT |
| P283AR9P1362_B10 | 113 | LPAPKNLVVSRVTEDSARLSWKRRWDSFDSFLIQYQESEKVGEAIV LTVPGSERSYDLTGLKPGTEYTVSIYGVDVEWFNGLPHHSNPLSAIF TT |
| P283AR9P1362_B2 | 114 | LPAPKNLVVSRVTEDSARLSWAKHPNSFDSFLIQYQESEKVGEAIVL TVPGSERSYDLTGLKPGTEYTVSIYGVDVVVNELNNPLFSNPLSAIFT T |
| P283AR9P1362_B8 | 115 | LPAPKNLVVSRVTEDSARLSWWTSPLPFDSFLIQYQESEKVGEAIVL TVPGSERSYDLTGLKPGTEYTVSIYGVDVKYDIDSRPISSNPLSAIFTT |
| P283AR9P1362_C12 | 116 | LPAPKNLVVSRVTEDSARLSWAKNLHSFDSFLIQYQESEKVGEAIVL TVPGSERSYDLTGLKPGTEYTVSIYGVDVKYDIDSRPISSNPLSAIFTT |
| P283AR9P1362_C6 | 117 | LPAPKNLVVSRVTEDSARLSWYPSDPPFDSFLIQYQESEKVGEAIVL TVPGSERSYDLTGLKPGTEYTVSIYGVPNYHSRRSYYYSNPLSAIFTT |
| P283AR9P1362_C7 | 118 | LPAPKNLVVSRVTEDSARLSWVKRATSFDSFLIQYQESEKVGEAIVL TVPGSERSYDLTGLKPGTEYTVSIYGVDVRYNEGQPIWSNPLSAIFT T |
| P283AR9P1362_D2 | 119 | LPAPKNLVVSRVTEDSARLSWQRPKSGFFDSFLIQYQESEKVGEAIV LTVPGSERSYDLTGLKPGTEYTVSIYGVDVKYDIDSRPISSNPLSAIFT T |
| P283AR9P1362_D3 | 120 | LPAPKNLVVSRVTEDSARLSWPVESNAFDSFLIQYQESEKVGEAIVL TVPGSERSYDLTGLKPGTEYTVSIYGVDVEYDQHGRPRWSNPLSAI FTT |
| P283AR9P1362_D4 | 121 | LPAPKNLVVSRVTEDSARLSWREHDSFDSFLIQYQESEKVGEAIVL TVPGSERSYDLTGLKPGTEYTVSIYGVDVKYDIDSRPISSNPLSAIFTT |
| P283AR9P1362_D6 | 122 | LPAPKNLVVSRVTEDSARLSWAKRPGAFDSFLIQYQESEKVGEAIVL TVPGSERSYDLTGLKPGTEYTVSIYGVDVKYDIDSRPISSNPLSAIFTT |
| P283AR9P1362_D7 | 123 | LPAPKNLVVSRVTEDSARLSWVKRATSFDSFLIQYQESEKVGEAIVL TVPGSERSYDLTGLKPGTEYTVSIYGVDVKYDIDSRPISSNPLSAIFTT |
| P283AR9P1362_E9 | 124 | LPAPKNLVVSRVTEDSARLSWVPSPWGFDSFLIQYQESEKVGEAIV LTVPGSERSYDLTGLKPGTEYTVSIYGVDVKYDIDSRPISSNPLSAIFT T |
| P283AR9P1362_F12 | 125 | LPAPKNLVVSRVTEDSARLSWARNITSFDSFLIQYQESEKVGEAIVL TVPGSERSYDLTGLKPGTEYTVSIYGVDVKYDIDSRPISSNPLSAIFTT |
| P283AR9P1362_F2 | 126 | LPAPKNLVVSRVTEDSARLSWRKKDHPFDSFLIQYQESEKVGEAIVL TVPGSERSYDLTGLKPGTEYTVSIYGVDVKYDIDSRPISSNPLSAIFTT |
| P283AR9P1362_F8 | 127 | LPAPKNLVVSRVTEDSARLSWGYYHGHFDSFLIQYQESEKVGEAIV LTVPGSERSYDLTGLKPGTEYTVSIYGVDVKWEGNRPVASNPLSAIF TT |
| P283AR9P1362_G11 | 128 | LPAPKNLVVSRVTEDSARLSWRKEATSFDSFLIQYQESEKVGEAIVL TVPGSERSYDLTGLKPGTEYTVSIYGVDVKYDIDSRPISSNPLSAIFTT |
| P283AR9P1362_G3 | 129 | LPAPKNLVVSRVTEDSARLSWVKRATSFDSFLIQYQESEKVGEAIVL TVPGSERSYDLTGLKPGTEYTVSIYGVDVKWEGNRPVASNPLSAIFT T |

| | | Sequence listing |
|---|---|---|
| P283AR9P1362_H11 | 130 | LPAPKNLVVSRVTEDSARLSWPKIQGQHFDSFLIQYQESEKVGEAI VLTVPGSERSYDLTGLKPGTEYTVSIYGVDVKYDIDSRPISSNPLSAIF TT |
| P283BR9P1363_A10 | 131 | LPAPKNLVVSRVTEDSARLSWQRADDILPYFDSFLIQYQESEKVGE AIVLTVPGSERSYDLTGLKPGTEYTVSIYGVDVKYDIDSRPISSNPLSA IFTT |
| P283BR9P1363_A8 | 132 | LPAPKNLVVSRVTEDSARLSWVRSDTARFFDSFLIQYQESEKVGEAI VLTVPGSERSYDLTGLKPGTEYTVSIYGVDVKYDIDSRPISSNPLSAIF TT |
| P283BR9P1363_B2 | 133 | LPAPKNLVVSRVTEDSARLSWASTVDPHPRFDSFLIQYQESEKVGE AIVLTVPGSERSYDLTGLKPGTEYTVSIYGVDVKYDIDSRPISSNPLSA IFTT |
| P283BR9P1363_B6 | 134 | LPAPKNLVVSRVTEDSARLSWQRHSDAHPLFDSFLIQYQESEKVGE AIVLTVPGSERSYDLTGLKPGTEYTVSIYGVDVKWEGNRPVASNPL SAIFTT |
| P283BR9P1363_C4 | 135 | LPAPKNLVVSRVTEDSARLSWPIVNTPLHFDSFLIQYQESEKVGEAI VLTVPGSERSYDLTGLKPGTEYTVSIYGVDVQYTATGQPERSNPLSA IFTT |
| P283BR9P1363_C8 | 136 | LPAPKNLVVSRVTEDSARLSWAKTSDLHPLFDSFLIQYQESEKVGEA IVLIVPGSERSYDLTGLKPGTEYIVSIYGVDVKWEGNRPVASNPLS AIFTT |
| P283BR9P1363_D11 | 137 | LPAPKNLVVSRVTEDSARLSWNKKHDGQPTFDSFLIQYQESEKVGE AIVLTVPGSERSYDLTGLKPGTEYTVSIYGVDVVYEGSYPASSNPLSA IFTT |
| P283BR9P1363_E4 | 138 | LPAPKNLVVSRVTEDSARLSWIKSETSQPAFDSFLIQYQESEKVGEA IVLIVPGSERSYDLTGLKPGTEYTVSIYGVDVKWEGNRPVASNPLS AIFTT |
| P283BR9P1363_E6 | 139 | LPAPKNLVVSRVTEDSARLSWYARKFISPFDSFLIQYQESEKVGEAIV LTVPGSERSYDLTGLKPGTEYTVSIYGVDVKWEGNRPVASNPLSAIF TT |
| P283BR9P1363_F2 | 140 | LPAPKNLVVSRVTEDSARLSWYRPDNRAGAFDSFLIQYQESEKVGE AIVLTVPGSERSYDLTGLKPGTEYTVSIYGVDVKYDIDSRPISSNPLSA IFTT |
| P283BR9P1363_F4 | 141 | LPAPKNLVVSRVTEDSARLSWERIVQTPHFDSFLIQYQESEKVGEAI VLTVPGSERSYDLTGLKPGTEYTVSIYGVDVKWEGNRPVASNPLSA IFTT |
| P283BR9P1363_F6 | 142 | LPAPKNLVVSRVTEDSARLSWPEEAVTATSFDSFLIQYQESEKVGEA IVLIVPGSERSYDLTGLKPGTEYTVSIYGVDVKWEGNRPVASNPLS AIFTT |
| P283BR9P1363_G2 | 143 | LPAPKNLVVSRVTEDSARLSWPKNQTNRHFDSFLIQYQESEKVGEA IVLTVPGSERSYDLTGLKPGTEYTVSIYGVDVKWEGNRPVASNPLS AIFTT |
| P283BR9P1363_G5 | 144 | LPAPKNLVVSRVTEDSARLSWYRATTPAPHFDSFLIQYQESEKVGE AIVLTVPGSERSYDLTGLKPGTEYTVSIYGVDVKWEGNRPVASNPL SAIFTT |
| P283BR9P1363_G7 | 145 | LPAPKNLVVSRVTEDSARLSWSAKKFPRHFDSFLIQYQESEKVGEAI VLTVPGSERSYDLTGLKPGTEYTVSIYGVDVKWEGNRPVASNPLSA IFTT |
| P283DR9P1364_A4 | 146 | LPAPKNLVVSRVTEDSARLSWTAPDAAFDSFYIAYPEWPVQGEAIV LTVPGSERSYDLTGLKPGTEYFVIIYGVKGGDWSEPLSAIFTT |
| P283DR9P1364_A7 | 147 | LPAPKNLVVSRVTEDSARLSWTAPDAAFDSFRIAYPEWPVRGDAIV LTVPGSERSYDLTGLKPGTEYWVIIQGVKGGTDSFPLSAIFTT |
| P283DR9P1364_B1 | 148 | LPAPKNLVVSRVTEDSARLSWTAPDAAFDSFYITYPEIPLGGEAIVLT VPGSERSYDLTGLKPGTEYFVVIYGVKGGLLSSPLSAIFTT |
| P283DR9P1364_B11 | 149 | LPAPKNLVVSRVTEDSARLSWTAPDAAFDSFYISYPEWEQLGEAIV LTVPGSERSYDLTGLKPGTEYFVVIYGVKGGALSAPLSAIFTT |

-continued

| | | |
|---|---|---|
| P283DR9P1364_B4 | 150 | LPAPKNLVVSRVTEDSARLSWTAPDAAFDSFAISYPEWPPPGEAIV<br>LTVPGSERSYDLTGLKPGTEYWVIILGVKGGDQSWPLSAIFTT |
| P283DR9P1364_C10 | 151 | LPAPKNLVVSRVTEDSARLSWTAPDAAFDSFQIAYPEWPKDGEAI<br>VLTVPGSERSYDLTGLKPGTEYAVFIWGVKGGVYSNPLSAIFTT |
| P283DR9P1364_D11 | 152 | LPAPKNLVVSRVTEDSARLSWTAPDAAFDSFDIAYPEWPPKGEAIV<br>LTVPGSERSYDLTGLKPGTEYFVVIYGVKGGIHSAPLSAIFTT |
| P283DR9P1364_D8 | 153 | LPAPKNLVVSRVTEDSARLSWTAPDAAFDSFQIAYPETPIQGEAIVL<br>TVPGSERSYDLTGLKPGTEYFVIIHGVKGGITSFPLSAIFTT |
| P283DR9P1364_D9 | 154 | LPAPKNLVVSRVTEDSARLSWTAPDAAFDSFGISYPEWPPLGEAIV<br>LTVPGSERSYDLTGLKPGTEYWVIIFGVKGGERSWPLSAIFTT |
| P283DR9P1364_E3 | 155 | LPAPKNLVVSRVTEDSARLSWTAPDAAFDSFGIAYPELPIGGEAIVL<br>TVPGSERSYDLTGLKPGTEYFVIIRGVKGGTLSPPLSAIFTT |
| P283DR9P1364_E5 | 156 | LPAPKNLVVSRVTEDSARLSWTAPDAAFDSFWISYPEWPVPGEAI<br>VLTVPGSERSYDLTGLKPGTEYWVIIQGVKGGKLSWPLSAIFTT |
| P283DR9P1364_E7 | 157 | LPAPKNLVVSRVTEDSARLSWTAPDAAFDSFNIAYPEWPVRGEAIV<br>LTVPGSERSYDLTGLKPGTEYWVIIYGVKGGDRSNPLSAIFTT |
| P283DR9P1364_E8 | 158 | LPAPKNLVVSRVTEDSARLSWTAPDAAFDSFSIAYPEWPVHGEAIV<br>LTVPGSERSYDLTGLKPGTEYFVIIYGVKGGVLSEPLSAIFTT |
| P283DR9P1364_E9 | 159 | LPAPKNLVVSRVTEDSARLSWTAPDAAFDSFDIAYPEWPTKGEAIV<br>LTVPGSERSYDLTGLKPGTEYFVVINGVKGGWRSFPLSAIFTT |
| P283DR9P1364_F2 | 160 | LPAPKNLVVSRVTEDSARLSWTAPDAAFDSFWIAYPEWPVPGEAI<br>VLTVPGSERSYDLTGLKPGTEYFVIIQGVKGGFGSFPLSAIFTT |
| P283DR9P1364_F6 | 161 | LPAPKNLVVSRVTEDSARLSWTAPDAAFDSFTIAYPEREQDKWGE<br>AIVLTVPGSERSYDLTGLKPGTEYWVIIQGVKGGRPSTPLSAILTT |
| P283DR9P1364_F8 | 162 | LPAPKNLVVSRVTEDSARLSWTAPDAAFDSFAIAYPEWPPGEAIVL<br>TVPGSERSYDLTGLKPGTEYFVIIYGVKGGWTSPPLSAIFTT |
| P283DR9P1364_G10 | 163 | LPAPKNLVVSRVTEDSARLSWTAPDAAFDSFSIAYPEWPGSGEAIV<br>LTVPGSERSYDLTGLKPGTEYFVVIFGVKGGSQSWPLSAIFTT |
| P283DR9P1364_G9 | 164 | LPAPKNLVVSRVTEDSARLSWTAPDAAFDSFGIWYPEWPVGGEAI<br>VLTVPGSERSYDLTGLKPGTEYWVNISGVKGGEYSFPLSAIFTT |
| P283DR9P1364_H1 | 165 | LPAPKNLVVSRVTEDSARLSWTAPDAAFDSFQISYPEWPVHGEAIV<br>LTVPGSERSYDLTGLKPGTEYWVIIWGVKGGRQSWPLSAIFTT |
| P283DR9P1364_H11 | 166 | LPAPKNLVVSRVTEDSARLSWTAPDAAFDSFDIAYPELPLGGEAIVL<br>TVPGSERSYDLTGLKPGTEYFVIIWGVKGGDRSEPLSAIFTT |
| P283DR9P1364_H6 | 167 | LPAPKNLVVSRVTEDSARLSWTAPDAAFDSFIIAYPETPVRGEAIVL<br>TVPGSERSYDLTGLKPGTEYFVIIIGVKGGQESFPLSAIFTT |
| P283DR9P1364_H9 | 168 | LPAPKNLVVSRVTEDSARLSWTAPDAAFDSFSISYIEYPEIPGGEAIV<br>LTVPGSERSYDLTGLKPGTEYWVPIWGVKGGIQSWPLSAIFTT |
| P283ER9P1365_A1 | 169 | LPAPKNLVVSRVTEDSARLSWTAPDAAFDSFGIAYVEWWHRGEAI<br>SLPVPGSERSYDLTGLKPGTEYNVIITGVKGGIPSHPLGAIFTT |
| P283ER9P1365_A7 | 170 | LPAPKNLVVSRVTEDSARLSWTAPDAAFDSFYIPYWESEVYGEAIA<br>LPVPGSERSYDLTGLKPGTEYQVSIIGVKGGVYSQPLAAIFTT |
| P283ER9P1365_B6 | 171 | LPAPKNLVVSRVTEDSARLSWTAPDAAFDSFGIGYAEPVVTGEAIS<br>LSVPGSERSYDLTGLKPGTEYWVVIIGVKGGINSYPLGAIFTT |
| P283ER9P1365_C1 | 172 | LPAPKNLVVSRVTEDSARLSWTAPDAAFDSFYIPYWESEVYGEAIA<br>LPVTGSERSYDLTGLKPGTEYQVSIIGVKGGVYSQPLAAIFTT |
| P283ER9P1365_E2 | 173 | LPAPKNLVVSRVTEDSARLSWTAPDAAFDSFYIPYRESEFRGEAIAL<br>PVPGSERSYDLTGLKPGTKYRVIIIGVKGGEFSQPLAAIFTT |
| P283ER9P1365_F4 | 174 | LPAPKNLVVSRVTEDSARLSWTAPDAAFDSFYIPYRESEFRGEAIAL<br>PVPGSERSYDLTGLKPGTKYSVIIIGVKGGEFSQPLGAIFTT |
| P283ER9P1365_G1 | 175 | LPAPKNLVVSRVTEDSARLSWTAPDAAFDSFYIPYRESEFRGEAIAL<br>SVPGSERSYDLTGLKPGTKYRVIIIGVKGGEFSQPLGAIFTT |

| | | |
|---|---|---|
| P283ER9P1365_G3 | 176 | LPAPKNLVVSRVTEDSARLSWTAPDAAFDSFGISYYEWAPNGEA1<br>QLSVPGSERSYDLTGLKPGTEYHVVIIGVKGGEPSHPLGAIFTT |
| P283ER9P1365_H3 | 177 | LPAPKNLVVSRVTEDSARLSWTAPDAAFDSFYIPYRESEFRGEAIAL<br>PVPGSERSYDLTGLKPGTKYRVIIIGVKGGEFSQPLSAIFTT |
| P283FR9P1366_A1 | 178 | LPAPKNLVVSRVTEDSARLSWTAPDAAFDSFWITYPEWPVPGEA1<br>VLTVPGSERSYDLTGLKPGTEYAVFIWGVKGGDASEPLSAIFTT |
| P283FR9P1366_A5 | 179 | LPAPKNLVVSRVTEDSARLSWTAPDAAFDSFWIAYPEWPTRGEA1<br>VLTVPGSERSYDLTGLKPGTEYFVVIYGVKGGSPSPPLSAIFTT |
| P283FR9P1366_A9 | 180 | LPAPKNLVVSRVTEDSARLSWTAPDAAFDSFNIAYGEYPGPGEAIV<br>LTVPGSERSYDLTGLKPGTEYWVPIWGVKGGELSEPLSAIFTT |
| P283FR9P1366_B7 | 181 | LPAPKNLVVSRVTEDSARLSWTAPDAAFDSFWITYPEWPVNGEA1<br>VLTVPGSERSYDLTGLKPGTEYWVVIWGVKGGVESPPLSAIFTT |
| P283FR9P1366_C2 | 182 | LPAPKNLVVSRVTEDSARLSWTAPDAAFDSFKISYPEWPPEGEAIV<br>LTVPGSERSYDLTGLKPGTEYAVFIWCVKGGEHSWPLSAIFTT |
| P283FR9P1366_C3 | 183 | LPAPKNLVVSRVTEDSARLSWTAPDAAFDSFKIAYPEWPDGGEAIV<br>LTVPGSERSYDLTGLKPGTEYFVIIYGVKGGILSPPLSAIFTT |
| P283FR9P1366_C4 | 187 | LPAPKNLVVSRVTEDSARLSWTAPDAAFDSFNIAYPEWPVRGEAIV<br>LTVPGSERSYDLTGLKPGTEYWVIIIGVKGGEDSWPLSAIFTT |
| P283FR9P1366_C6 | 185 | LPAPKNLVVSRVTEDSARLSWTAPDAAFDSFSIAYPEWPVYGEAIV<br>LTVPGSERSYDLTGLKPGTEYFVVIYGVKGGNYSDPLSAIFTT |
| P283FR9P1366_D12 | 186 | LPAPKNLVVSRVTEDSARLSWTAPDAAFDSFDIAYPEWPLGGEAIV<br>LTVPGSERSYDLTGLKPGTEYWVIILGVKGGDQSWPLSAIFTT |
| P283FR9P1366_D6 | 187 | LPAPKNLVVSRVTEDSARLSWTAPDAAFDSFNIFYPELVFPGEAIVL<br>TVPGSERSYDLTGLKPGTEYWVNISGVKGGEHSWPLSAIFTT |
| P283FR9P1366_D7 | 188 | LPAPKNLVVSRVTEDSARLSWTAPDAAFDSFSIAYPELPVKGEAIVL<br>TVPGSERSYDLTGLKPGTEYFVVIWGVKGGTYSGPLSAIFTT |
| P283FR9P1366_D8 | 189 | LPAPKNLVVSRVTEDSARLSWTAPDAAFDSFEIAYPE1PIAGEAIVLT<br>VPGSERSYDLTGLKPGTEYFVIIYGVKGGDWSDPLSAIFTT |
| P283FR9P1366_E11 | 190 | LPAPKNLVVSRVTEDSARLSWTAPDAAFDSFDIAYPEWPVPGEAIV<br>LTVPGSERSYDLTGLKPGTEYWVIIKGVKGGNISWPLSAIFTT |
| P283FR9P1366_F5 | 191 | LPAPKNLVVSRVTEDSARLSWTAPDAAFDSFDIGYPEWPIKGEAIV<br>LTVPGSERSYDLTGLKPGTEYWVIIWGVKGGDRSEPLSAIFTT |
| P283FR9P1366_F8 | 192 | LPAPKNLVVSRVTEDSARLSWTAPDAAFDSFAIAYPEIAKWGEAIV<br>LTVPGSERSYDLTGLKPGTEYFVIIYGVKGGVHSFPLSAIFTT |
| P283FR9P1366_F9 | 193 | LPAPKNLVVSRVTEDSARLSWTAPDAAFDSFH1FYPELPIAGEAIVLT<br>VPGSERSYDLTGLKPGTEYWVNISGVKGGYESWPLSAIFTT |
| P283FR9P1366_G1 | 194 | LPAPKNLVVSRVTEDSARLSWTAPDAAFDSFYISYPELPVEGEAIVL<br>TVPGSERSYDLTGLKPGTEYWVIIWGVKGGATSEPLSAIFTT |
| P283FR9P1366_G5 | 195 | LPAPKNLVVSRVTEDSARLSWTAPDAAFDSFQIAYPEYPALGEAIVL<br>TVPGSERSYDLTGLKPGTEYFVIIIGVKGGDESFPLSAIFTT |
| P283FR9P1366_G8 | 196 | LPAPKNLVVSRVTEDSARLSWTAPDAAFDSFDIAYPELPIGGEAIVL<br>TVPGSERSYDLTGLKPGTEYFVVIYGVKGGIHSAPLSAIFTT |
| P283FR9P1366_H10 | 197 | LPAPKNLVVSRVTEDSARLSWTAPDAAFDSFNIAYPEWPPEGEAIV<br>LTVPGSERSYDLTGLKPGTEYFVVIYGVKGGHLSDPLSAIFTT |
| P283FR9P1366_H11 | 198 | LPAPKNLVVSRVTEDSARLSWTAPDAAFDSFQIQYLETAPDGEAIV<br>LTVPGSERSYDLTGLKPGTEYYVWIPGVKGGAFSPLSAIFTT |
| P283FR9P1366_H3 | 199 | LPAPKNLVVSRVTEDSARLSWTAPDAAFDSFAIAYPEWPIKGEAIVL<br>TVPGSERSYDLTGLKPGTEYWVVIYGVKGGVFSEPLSAIFTT |
| P283FR9P1366_H5 | 200 | LPAPKNLVVSRVTEDSARLSWTAPDAAFDSFIYIENKVNGEAIVLTV<br>PGSERSYDLTGLKPGTEYHVTIGGVKGGTESNTLSAIFTT |

| | | |
|---|---|---|
| P283FR9P1366_H6 | 201 | LPAPKNLVVSRVTEDSARLSWTAPDAAFDSFDIAYPEWPVTGEAIV<br>LTVPGSERSYDLTGLKPGTEYWVIIFGVKGGERSWPLSAIFTT |
| P283FR9P1366_H7 | 202 | LPAPKNLVVSRVTEDSARLSWTAPDAAFDSFQIAYPEYPALGEAIVL<br>TVPGSERSYDLTGLKPGTEYFVIIAGVKGGIQSWPLSAIFTT |
| P283FR9P1366_H8 | 203 | LPAPKNLVVSRVTEDSARLSWTAPDAAFDSFYISYPEWPGSGEAIV<br>LTVPGSERSYDLTGLKPGTEYAVFIWCVKGGWLSDPLSAIFTT |
| P283FR9P1366_H9 | 204 | LPAPKNLVVSRVTEDSARLSWTAPDAAFDSFEIAYPEWPVNGEAIV<br>LTVPGSERSYDLTGLKPGTEYWVVIWGVKGGVNSYPLSAIFTT |
| P283GR7P1367_A11 | 205 | LPAPKNLVVSRVTEDSARLSWTAPDAAFDSFDIAYPEWPTDGEAIV<br>LTVPGSERSYDLTGLKPGTEYFVIIYGVKGGSYSEPLSAIFTT |
| P283GR7P1367_B4 | 206 | LPAPKNLVVSRVTEDSARLSWTAPDAAFDSFSILYYELPPSGEAIVLT<br>VPGSERSYDLTGLKPGTEYTVSIFGVKGGDNSFPLSAIFTT |
| P283GR7P1367_B7 | 207 | LPAPKNLVVSRVTEDSARLSWTAPDAAFDSFDIAYPEWPTDGEAIV<br>LTVPGSERSYDLTGLKPGTEYFVVIYGVKGGHWSYPLSAIFTT |
| P283GR7P1367_B9 | 208 | LPAPKNLVVSRVTEDSARLSWTAPDAAFDSFEIWYHEYHPRGEAIV<br>LTVPSSERSYDLTGLKPGTEYDVVISGVKGGHWSYPLSAIFTT |
| P283GR7P1367_C9 | 209 | LPAPKNLVVSRVTEDSARLSWTAPDAAFDSFLIGYPEWPLGGEAIV<br>LTVPGSERSYDLTGLKPGTEYWVIIYGVKGGEYSDPLSAIFTT |
| P283GR7P1367_E5 | 210 | LPAPKNLVVSRVTEDSARLSWTAPDAAFDSFEIWYHEYHPRGEAIV<br>LTVPGSERSYDLTGLKPGTEYDVVISGVKGGHWSYPLSAIFTT |
| P283GR7P1367_F5 | 211 | LPAPKNLVVSRVTEDSARLSWTAPDAAFDSFDIAYPEWPTDGEAIV<br>LTVPGSERSYDLTGLKPGTEYFVIIYGVKGGALSRPLSAIFTT |
| P283GR7P1367_G8 | 212 | LPAPKNLVVSRVTEDSARLSWTAPDAAFDSFYIAYPEYVWGGEATS<br>LGEAIVLTVPGSERSYDLTGLKPGTEYFVVITGVKGGLGSYPLSAIFT<br>T |
| P283GR7P1367_H2 | 213 | LPAPKNLVVSRVTEDSARLSWTAPDAAFDSFDIAYPEWPTDGEAIV<br>LTVPGSERSYDLTGLKPGTEYFVVIYGVKGGGRSYPLSAIFTT |
| P283GR7P1367_H8 | 214 | LPAPKNLVVSRVTEDSARLSWTAPDAAFDSFSINYWEEDPAGEAIV<br>LTVPGSERSYDLTGLKPGTEYRVLIGGVKGGHGSLPLSAIFTT |
| P283GR7P1367_H9 | 215 | LPAPKNLVVSRVTEDSARLSWTAPDAAFDSFDIAYPEWPTDGEAIV<br>LTVPGSERSYDLTGLKPGTEYFVVIYGVKGGGRSAPLSAIFTT |
| P283HR7P1368_A10 | 216 | LPAPKNLVVSRVTEDSARLSWTAPDAAFDSFWIFYLEPFPRGEAIPL<br>EVPGSERSYDLTGLKPGTEYSVDIRGVKGGDHSDPLWAYFTT |
| P283HR7P1368_B12 | 217 | LPAPKNLVVSRVTEDSARLSWTAPDAAFDSFGIGYVEFTRAGEAISL<br>SVPGSERSYDLTGLKPGTEYHVVIIGVKGGEPSHPLGAPFTT |
| P283HR7P1368_C3 | 218 | LPAPKNLVVSRVTEDSARLSWTAPDAAFDSFGIGYAEPAVTGEAIS<br>LSVPGSKRSYDLTGLKPGTEYWVIIGVKGGINSYPLGASFTT |
| P283HR7P1368_D1 | 219 | LPAPKNLVVSRVTEDSARLSWTAPDAAFDSFGISYYEWAPNGEAI<br>QLSVPGSERSYDLTGLKPGTEYHVVIIGVKGGEPSHPLGAPFTT |
| P283HR7P1368_D2 | 220 | LPAPKNLVVSRVTEDSARLSWTAPDAAFNSFGIGYAEPAVTGEAIS<br>LSVPGSERSYDLTGLKPGTEYWVIIGVKGGINSYPLGASFTT |
| P283HR7P1368_D4 | 221 | LPAPKNLVVSRVTEDSARLSWTAPDAAFDSFAIWCVEPIPEGEAIPL<br>FVPGSERSYDLTGLKPGTEYRVGIRGVKGGTFSSPLAAPFTT |
| P283HR7P1368_F10 | 222 | LPAPKNLVVSRVTEDSARLSWTAPDAAFDSFYIPYRESEFRGEAIAL<br>PVPGSERSYDLTGLKPGTKYRVIIIGVKGGEFSQPLGAIFTT |
| P283HR7P1368_F6 | 223 | LPAPKNLVVSRVTEDSARLSWTAPDAAFDSFGIGYIEWVHRGEAIS<br>LHVPGSERSYDLTGLKPGTEYVVAIVGVKGGEPSTPLGAPFTT |
| P283HR7P1368_G1 | 224 | LPAPKNLVVSRVTEDSARLSWTAPDAAFDSFLITYWEIEPEGEAIFL<br>GVPGSERSYDLTGLKPGTEYRVQINGVKGGTISYPLFAGFTT |
| P283HR7P1368_G10 | 225 | LPAPKNLVVSRVTEDSARLSWTAPDAAFDSFGIAYVEWWHRGEAI<br>SLPVPGSERSYDLTGLKPGTEYWVTILGVKGGIISTPLGASFTT |

-continued

Sequence listing

| | | |
|---|---|---|
| P283HR7P1368_G11 | 226 | LPAPKNLVVSRVTEDSARLSWTAPDAAFDSFGIGYAEPAVTGEAIS LSVPGSERSYDLTGLKPGTEYWVVIIGVKGGINSYPLGASFTT |
| P283HR7P1368_H1 | 227 | LPAPKNLVVSRVTEDSARLSWTAPDAAFDSFGIAYIETARWGEAISL TVPGSERSYDLTGLKPGTEYNVVIIGVKGGTPSHPLGAPFTT |
| P283HR7P1368_H8 | 228 | LPAPKNLVVSRVTEDSARLSWTAPDAAFDSFGITYLDPRNGEAISL NVPGSERSYDLTGLKPGTEYWVVIIGVKGGINSYPLGASFTT |
| CD8S368 | 229 | LPAPKNLVVSRVTEDSARLSWTAPDAAFDSFQIAYPEWPPP GEATVLTVPGSCRSYDLTGLKPGTEYEVIIQGVKGGVESWP LSATFTT |
| CD8S367 | 230 | LPAPKNLVVSRVTEDSARLSWTAPDAAFDSFAIAYPEWPPQ GEAIVLTVPGSCRSYDLTGLKPGTEYFVVIYGVKGGSYSAP LSATFTT |
| CD8S370 | 231 | LPAPKNLVVSRVTEDSARLSWTAPDAAFDSFAITYIEKEHI EDGEAIVLTVPGSCRSYDLTGLKPGTEYWVPIWGVKGGANS WPLSAIFTT |
| CD8S365 | 232 | LPAPKNLVVSRVTEDSARLSWTAPDAAFDSFGILYYEPVDS GEAITLPVPGSCRSYDLTGLKPGTEYWVVITGVKGGAPSTP LGTIFTT |
| CD8S369 | 233 | LPAPKNLVVSRVTEDSARLSWAKRPGAFDSFLIQYQESEKV GEATVLTVPGSCRSYDLTGLKPGTEYTVSIYGVDVKYDIDS RPISSNPLSAIFTT |
| CD8S366 | 234 | LPAPKNLVVSRVTEDSARLSWTAPDAAFDSFWITYPEWPDP GGEATVLTVPGSCRSYDLTGLKPGTEYFVVIYGVKGGETYS PLSAIFTT |

| Clone | SEQID No | Parent | Sequence |
|---|---|---|---|
| CD8S371 | 235 | P282DR9P1359_F5 | LPAPKNLVVSRVTEDSARLSWT APDAAFDSFQIAYPEYPPPGEAI VLTVPGSERSYDLTGLKPGTEYF VIIQGVKGGVESWPLSAIFTT |
| CD8S372 | 236 | P282DR9P1359_F5 | LPAPKNLVVSRVTEDSARLSWT APDAAFDSFQIAYPELPPPGEAIV LTVPGSERSYDLTGLKPGTEYFV IIQGVKGGVESWPLSAIFTT |
| CD8S373 | 237 | P282DR9P1359_F5 | LPAPKNLVVSRVTEDSARLSWT APDAAFDSFQIAYPEIPPPGEAIV LTVPGSERSYDLTGLKPGTEYFV IIQGVKGGVESWPLSAIFTT |
| CD8S374 | 238 | P282DR9P1359_F5 | LPAPKNLVVSRVTEDSARLSWT APDAAFDSFQIAYPEWPPPGEAI VLTVPGSERSYDLTGLKPGTEYF VIIQGVKGGVESYPLSAIFTT |
| CD8S375 | 239 | P282DR9P1359_F5 | LPAPKNLVVSRVTEDSARLSWT APDAAFDSFQIAYPEWPPPGEAI VLTVPGSERSYDLTGLKPGTEYF VIIQGVKGGVESLPLSAIFTT |
| CD8S376 | 240 | P282DR9P1359_F5 | LPAPKNLVVSRVTEDSARLSWT APDAAFDSFQIAYPEWPPPGEAI VLTVPGSERSYDLTGLKPGTEYF VIIQGVKGGVESSPLSAIFTT |
| CD8S377 | 241 | P282DR9P1359_F5 | LPAPKNLVVSRVTEDSARLSWT APDAAFDSFQIAYPEWPPPGEAI VLTVPGSERSYDLTGLKPGTEYF VIIQGVKGGVESEPLSAIFTT |
| CD8S378 | 242 | P282DR9P1359_G7 | LPAPKNLVVSRVTEDSARLSWT APDAAFDSFAITYIEKEHIEEGEA IVLTVPGSERSYDLTGLKPGTEY WVPIWGVKGGANSWPLSAIFTT |
| CD8S379 | 243 | P282DR9P1359_G7 | LPAPKNLVVSRVTEDSARLSWT APDAAFDSFAITYIEKEHIESGEA |

| | | | |
|---|---|---|---|
| | | | IVLTVPGSERSYDLTGLKPGTEY
WVPIWGVKGGANSWPLSAIFTT |
| CD8S380 | 244 | P282DR9P1359_G7 | LPAPKNLVVSRVTEDSARLSWT
APDAAFDSFAITYIEKEHIEDGEA
IVLTVPGSERSYDLTGLKPGTEY
YVPIWGVKGGANSWPLSAIFTT |
| CD8S381 | 245 | P282DR9P1359_G7 | LPAPKNLVVSRVTEDSARLSWT
APDAAFDSFAITYIEKEHIEDGEA
IVLTVPGSERSYDLTGLKPGTEY
FVPIWGVKGGANSWPLSAIFTT |
| CD8S382 | 246 | P282DR9P1359_G7 | LPAPKNLVVSRVTEDSARLSWT
APDAAFDSFAITYIEKEHIEDGEA
IVLTVPGSERSYDLTGLKPGTEY
SVPIWGVKGGANSWPLSAIFTT |
| CD8S383 | 247 | P282DR9P1359_G7 | LPAPKNLVVSRVTEDSARLSWT
APDAAFDSFAITYIEKEHIEDGEA
IVLTVPGSERSYDLTGLKPGTEY
WVPIYGVKGGANSWPLSAIFTT |
| CD8S384 | 248 | P282DR9P1359_G7 | LPAPKNLVVSRVTEDSARLSWT
APDAAFDSFAITYIEKEHIEDGEA
IVLTVPGSERSYDLTGLKPGTEY
WVPIFGVKGGANSWPLSAIFTT |
| CD8S385 | 249 | P282DR9P1359_G7 | LPAPKNLVVSRVTEDSARLSWT
APDAAFDSFAITYIEKEHIEDGEA
IVLTVPGSERSYDLTGLKPGTEY
WVPISGVKGGANSWPLSAIFTT |
| CD8S386 | 250 | P282DR9P1359_G7 | LPAPKNLVVSRVTEDSARLSWT
APDAAFDSFAITYIEKEHIEDGEA
IVLTVPGSERSYDLTGLKPGTEY
WVPIWGVKGGANSYPLSAIFTT |
| CD8S387 | 251 | P282DR9P1359_G7 | LPAPKNLVVSRVTEDSARLSWT
APDAAFDSFAITYIEKEHIEDGEA
IVLTVPGSERSYDLTGLKPGTEY
WVPIWGVKGGANSEPLSAIFTT |
| CD8S388 | 252 | P282DR9P1359_G7 | LPAPKNLVVSRVTEDSARLSWT
APDAAFDSFAITYIEKEHIEDGEA
IVLTVPGSERSYDLTGLKPGTEY
WVPIWGVKGGAQSWPLSAIFTT |
| CD8S389 | 253 | P282ER9P1360_C8 | LPAPKNLVVSRVTEDSARLSWT
APDAAFDSFGILYYEPVDSGEAI
TLPVPGSERSYDLTGLKPGTEYF
VVITGVKGGAPSTPLGTIFTT |
| CD8S390 | 254 | P282ER9P1360_C8 | LPAPKNLVVSRVTEDSARLSWT
APDAAFDSFGILYYEPVDSGEAI
TLPVPGSERSYDLTGLKPGTEYY
VVITGVKGGAPSTPLGTIFTT |
| CD8S391 | 255 | P282ER9P1360_C8 | LPAPKNLVVSRVTEDSARLSWT
APDAAFDSFGILYYEPVDSGEAI
TLPVPGSERSYDLTGLKPGTEYH
VVITGVKGGAPSTPLGTIFTT |
| CD8S392 | 256 | P282DR9P1359_F7 | LPAPKNLVVSRVTEDSARLSWT
APDAAFDSFAIAYPEYPPQGEAI
VLTVPGSERSYDLTGLKPGTEYF
VVIYGVKGGSYSAPLSAIFTT |
| CD8S393 | 257 | P282DR9P1359_F7 | LPAPKNLVVSRVTEDSARLSWT
APDAAFDSFAIAYPELPPQGEAI
VLTVPGSERSYDLTGLKPGTEYF
VVIYGVKGGSYSAPLSAIFTT |
| CD8S394 | 258 | P282DR9P1359_F7 | LPAPKNLVVSRVTEDSARLSWT
APDAAFDSFAIAYPEIPPQGEAIV
LTVPGSERSYDLTGLKPGTEYFV
VIYGVKGGSYSAPLSAIFTT |

| | | | |
|---|---|---|---|
| CD8S395 | 259 | P282DR9P1359_F7 | LPAPKNLVVSRVTEDSARLSWT APDAAFDSFAIAYPEHPPQGEAI VLTVPGSERSYDLTGLKPGTEYF VVIYGVKGGSYSAPLSAIFTT |
| CD8S396 | 260 | P282DR9P1359S5 | LPAPKNLVVSRVTEDSARLSWT APDAAFDSFYITYPEWPDGGEA IVLTVPGSERSYDLTGLKPGTEY FVVIYGVKGGEIYSPLSAIFTT |
| CD8S397 | 261 | P282DR9P1359S5 | LPAPKNLVVSRVTEDSARLSWT APDAAFDSFQITYPEWPDGGEA IVLTVPGSERSYDLTGLKPGTEY FVVIYGVKGGEIYSPLSAIFTT |
| CD8S398 | 262 | P282DR9P1359_C5 | LPAPKNLVVSRVTEDSARLSWT APDAAFDSFSITYPEWPDGGEA IVLTVPGSERSYDLTGLKPGTEY FVVIYGVKGGEIYSPLSAIFTT |
| CD8S399 | 263 | P282DR9P1359S5 | LPAPKNLVVSRVTEDSARLSWT APDAAFDSFWITYPEYPDGGEA IVLTVPGSERSYDLTGLKPGTEY FVVIYGVKGGEIYSPLSAIFTT |
| CD8S400 | 264 | P282DR9P1359S5 | LPAPKNLVVSRVTEDSARLSWT APDAAFDSFWITYPELPDGGEA IVLTVPGSERSYDLTGLKPGTEY FVVIYGVKGGEIYSPLSAIFTT |
| CD8S401 | 265 | P282DR9P1359S5 | LPAPKNLVVSRVTEDSARLSWT APDAAFDSFWITYPEIPDGGEAI VLTVPGSERSYDLTGLKPGTEYF VVIYGVKGGEIYSPLSAIFTT |
| CD8S402 | 266 | P282DR9P1359S5 | LPAPKNLVVSRVTEDSARLSWT APDAAFDSFWITYPEWPPPGGE AIVLTVPGSERSYDLTGLKPGTE YFVVIYGVKGGEIYSPLSAIFTT |
| CD8S403 | 267 | P282DR9P1359J7 | LPAPKNLVVSRVTEDSARLSWT APDAAFDSFAIAYAEWPPQGEAI VLTVPGSERSYDLTGLKPGTEYF VVIYGVKGGSYSAPLSAIFTT |
| CD8S404 | 268 | P282DR9P1359S5 | LPAPKNLVVSRVTEDSARLSWT APDAAFDSFWITYAEWPDGGE AIVLTVPGSERSYDLTGLKPGTE YFVVIYGVKGGEIYSPLSAIFTT |
| CD8S405 | 269 | P282ER9P1360_C8 | LPAPKNLVVSRVTEDSARLSWT APDAAFDSFGILYYEPVDSGEAI TLTVPGSERSYDLTGLKPGTEY WVVITGVKGGAPSTPLGTIFTT |

SEQ ID. No. 270 Tencon25
LPAPKNLVVSEVTEDSARLSWTAPDAAFDSFLIQYQESEKVGEAIVLTVPGSERSYDLTGLKPGTEYTVSI
YGVKGGHRSNPLSAIFTT SEQ ID. NO: 271 Cyno CD8alpha
MRNQAPGRPKGATSPPPLPTGSRAPPVAPELRAEPRPGERVMAPPVTALLLPLVLLLHAARPNQFRVSPLG
RTWNLGETVELKCQVLLSNPTSGCSWLFQPRGTAARPTFLLYLSQNKPKAAEGLDTQRFSGKRLGDTFVLT
LRDFRQENEGYYFCSALSNSIMYFSHFVPVFLPAKPTTTPAPRPPTPAPTTASQPLSLRPEACRPAAGGSV
NTRGLDFACDIYIWAPLAGACGVLLLSLVITLYCNHRNRRRVCKCPRPVVKSGGKPSLSDRYV

What is claimed:

1. A protein comprising the amino acid sequence of SEQ ID NO 229, SEQ ID NO: 230, SEQ ID NO: 231, SEQ ID NO: 232, or SEQ ID NO: 234.

2. The protein of claim 1, wherein the protein comprises the amino acid of SEQ ID NO: 229.

3. The protein of claim 1, wherein the protein comprises the amino acid of SEQ ID NO: 230.

4. The protein of claim 1, wherein the protein is conjugated to a second molecule.

5. The protein of claim 1, wherein the protein comprises the amino acid of SEQ ID NO: 231.

6. The protein of claim 1, further comprising a methionine at the N-terminus of the protein.

7. The protein of claim 1, wherein the protein is coupled to a half-life extending moiety.

8. The protein of claim 7, wherein the half-life extending moiety is albumin, an albumin binding molecule, a polyethylene glycol (PEG), or an Fe region of an immunoglobulin.

9. A capture agent comprising the protein of claim 1.

10. The protein of claim 4, wherein the second molecule is a detectable label.

11. The protein of claim 10, wherein the detectable label is selected from a group consisting of radioactive isotope, magnetic beads, metallic beads, colloidal particles, a fluorescent dye, an electron-dense reagent, an enzyme, biotin, digoxigenin, and hapten.

12. The protein of claim 4, wherein the second molecule is a cytotoxic agent.

13. The protein of claim 4, wherein the second molecule is a chelator.

14. The protein of claim 4, wherein the second molecule is a nucleic acid molecule.

15. The protein of claim 1, wherein the protein comprises the amino acid of SEQ ID NO: 232.

16. The protein of claim 1, wherein the protein comprises the amino acid of SEQ ID NO: 234.

17. A composition comprising the protein of claim 1.

18. A composition comprising the protein of claim 12.

19. A composition comprising the protein of claim 13.

20. A composition comprising the protein of claim 14.

* * * * *